US006653445B1

(12) United States Patent
Ni et al.

(10) Patent No.: US 6,653,445 B1
(45) **Date of Patent: *Nov. 25, 2003**

(54) HUMAN CCV POLYPEPTIDES

(75) Inventors: Jian Ni, Rockville, MD (US); Craig A. Rosen, Laytonsville, MD (US); Reiner Gentz, Silver Spring, MD (US); Jeffrey Y. Su, Gaithersburg, MD (US); Geoffrey W. Krissansen, Auckland (NZ); Ping Feng, Gaithersburg, MD (US)

(73) Assignees: Human Genome Sciences, Inc., Rockville, MD (US); Auckland Uniservices, Limited, Auckland (NZ)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 71 days.

(21) Appl. No.: 09/010,147

(22) Filed: Jan. 21, 1998

Related U.S. Application Data

(60) Provisional application No. 60/034,204, filed on Jan. 21, 1997, and provisional application No. 60/034,205, filed on Jan. 21, 1997.

(51) Int. Cl.[7] .......... C07K 14/00

(52) U.S. Cl. .......... 530/350; 530/324; 530/325; 530/326; 530/327; 530/328; 435/69.1; 435/69.7; 435/7.1; 435/320.1; 536/23.1; 536/23.5

(58) Field of Search .......... 530/350, 324, 530/328, 327, 326, 325; 435/69.1, 7.1, 320.1, 69.7; 536/23.1, 23.5

(56) References Cited

U.S. PATENT DOCUMENTS

| | | | | |
|---|---|---|---|---|
| 5,536,637 A | | 7/1996 | Jacobs | 435/6 |
| 5,849,528 A | * | 12/1998 | Hillman et al. | 435/69.1 |
| 6,103,497 A | | 8/2000 | Hillman et al. | |

FOREIGN PATENT DOCUMENTS

| | | |
|---|---|---|
| EP | 0263072 | 4/1988 |
| WO | WO90/03394 | 4/1990 |
| WO | WO90/14432 | 11/1990 |
| WO | WO92/04376 | 3/1992 |
| WO | WO95/03328 | 2/1995 |
| WO | WO95/17506 | 6/1995 |
| WO | WO96/17925 | 6/1996 |

OTHER PUBLICATIONS

Examination of Patent Applications Containing Nucleotide Sequences. 1192 OG 68, 1996.*

Database GenBank on STN (1998) Bandman et al. Accession No. W82408, 1998.*

Database GenBank on STN (1998) Brundell et al., Accession No. W46607, 1998.*

Database GenBank on STN (1993) Sager, Accession No. R27058, 1993.*

GenSeq Accesion No: V73498 (Feb. 23, 1999).

GenSeq Accesion No: W82408 (Feb. 23, 1999).

GenBank Accesion No: C17482 Oct. 4, 1996.

GenBank Accesion No: U46281 May 20, 1996.

GeneSeq Accesion No: Q24508 (1992).

GeneSeq Accesion No: N90091 (1989).

GeneSeq Accesion No: T05627 (1996).

GeneSeq Accesion No: T01476 (1996).

* cited by examiner

*Primary Examiner*—Christopher S. F. Low
*Assistant Examiner*—Rita Mitra
(74) *Attorney, Agent, or Firm*—Human Genome Sciences, Inc.

(57) ABSTRACT

The present invention relates to novel human proteins and isolated nucleic acids containing the coding regions of the genes encoding such proteins. Also provided are vectors, host cells and recombinant methods for producing the proteins of the invention. The invention further relates to diagnostic and therapeutic methods useful for diagnosing and treating disorders related to these novel human secreted proteins.

24 Claims, 44 Drawing Sheets

FIG. 1A

HEMFI85 (SEQ ID NOS:1 and 2)

```
                                        10        20        30        40
                                         .         .         .         .
                                     1 AGCCCGGCTGGGCTGAGCGCAGGGAGCTGCTTGGCAGTGCCAG 43

        50        60        70        80        90       100       110       120
         .         .         .         .         .         .         .         .
44 AGCCCAGGCCCCAGAGCCCTGCTGGAGAGGAGGCAGACTGAGGCAGCAGGCCCCGCCAGCAGGCGAAGCAGGGAG ATG 121
                                                                               M   1

            130         140         150         160         170         180
              .           .           .           .           .           .
122 TCA GAC TGC TAC ACG GAG CTG GAG AAG GCA GTC ATT GTC CTG GTG GAA AAC TTC TAC AAA 181
  2  S   D   C   Y   T   E   L   E   K   A   V   I   V   L   V   E   N   F   Y   K  21

            190         200         210         220         230         240
              .           .           .           .           .           .
182 TAT GTG TCT AAG TAC AGC CTG GTC AAG AAC AAG ATC AGC AAG AGC AGC TTC CGC GAG ATG 241
 22  Y   V   S   K   Y   S   L   V   K   N   K   I   S   K   S   S   F   R   E   M  41

            250         260         270         280         290         300
              .           .           .           .           .           .
242 CTC CAG AAA GAG CTG AAC CAC ATG CTG TCG GAC ACA GGG AAC CGG AAG GCT GCG GAT AAG 301
 42  L   Q   K   E   L   N   H   M   L   S   D   T   G   N   R   K   A   A   D   K  61
```

FIG. 1B

```
                310        320        330        340        350        360
302 CTC ATC CAG AAC CTG GAT GCC AAT CAT GAT GGG CGC ATC AGC TTC GAT GAG TAC TGG ACC 361
 62  L   I   Q   N   L   D   A   N   H   D   G   R   I   S   F   D   E   Y   W   T  81

                370        380        390        400        410        420
362 TTG ATA GGC GGC ATC ACC GGC CCC ATC GCC AAA CTC ATC CAT GAG CAG GAG CAG CAG AGC 421
 82  L   I   G   G   I   T   G   P   I   A   K   L   I   H   E   Q   E   Q   Q   S 101

                430        440        450        460        470        480
422 AGC AGC TAG AGA CCC CTT TGG CCA CAC CTT CCA GGC ACT GGC CTG ATG CCC CGC CCT GGT 481
102  S   S   *                                                                      103

                490        500        510        520        530        540
482 GCT CTC CCC AGG CTC CCT CCT CAG CCT CCT GCC CAC CCA GGG CCC TTT ACT CTC TTC TCC 541

                550        560        570        580        590        600
542 CTC CAG ACC TTC CTC TGA CCC TTG CTG AAC TGG GGT CCC TTT GTG AGT GTC TCA GTC TAG 601

                610        620        630        640        650        660
602 AGG TAC CTC CCT CCC TGG GGG GTC TCA GCT CCT GGA GTC GCA GGC CCT TGG GGC CCC TCT 661

                670        680        690        700        710        720
662 GTG AGA TCT CAA TGC TGT CTG GGG ACC CTA AGA GTT TTC TCA CCT GTT CAG TCT CAT CTA 721
```

FIG. 1C

```
              730               740               750               760               770               780
               .                 .                 .                 .                 .                 .
722 ACC TTC CAA TGT CTG ATG TTC CTG CCA AAT TCC TGC CTG ATT CTG GGT CCG TCC TGA CCT 781

              790               800               810               820               830               840
               .                 .                 .                 .                 .                 .
782 CCA AAG GTC AGC TTG GTG CTT GAG GTC TCC CTG CTC TTG GTG GCA GTG GTA GCA GCA ACA 841

              850               860               870               880               890               900
               .                 .                 .                 .                 .                 .
842 GCA GCA GCA GCA GCA GCA GCA GCA GCA GAG ACC TCT CCA CTT TCC CTT AGC CCC TCT GCT 901

              910               920               930               940               950               960
               .                 .                 .                 .                 .                 .
902 GGG TAG AGA GGC ACT TTC AGG GAC TTC CCT CCA GCT GCC TCT TCA TCT GGG AAT GAG CTA 961

              970               980               990              1000              1010              1020
               .                 .                 .                 .                 .                 .
962 AGC AAG GCT GAG CCT CCT CCT GTT GCT TGA AAT AAT GAT GAT ATA AAG GCT GGA TTT GGA 1021

             1030              1040              1050              1060              1070              1080
               .                 .                 .                 .                 .                 .
1022 GTT TGT ATC CCC TGG TCC CTC TGG GAT GCT CAT TAA AAC CTT CCC ACT CCT TGA AAA AAA 1081

             1090
               .
1082 AAA AAA AAA AAA 1093
```

HTXET53 (SEQ ID NOS:3 and 4)

```
        10                              30                              50
GCACGAGGCAGGCTCCCTGCCCATAAAACAGGGTGTGAAAGGCATCTCAGCGGCTGCCCC
        70                              90                             110
ACCATGGCTACCTGGGCCCTCCTGCTCCTTGCAGCCATGCTCCTGGGCAACCCAGGCCTT
   M  A  T  W  A  L  L  L  L  A  A  M  L  L  G  N  P  G  L
       130                             150                             170
GAGGTCAGTGTGAGCCCCAAGGGCAAGAACACTTCTGGAAGGGAGAGTGGATTTGGCTGG
E  V  S  V  S  P  K  G  K  N  T  S  G  R  E  S  G  F  G  W
       190                             210                             230
GCCATCTGGATGGAAGGTCTGGTCTTCTCTCGTCTGAGCCCTGAGTACTACGACCTGGCA
A  I  W  M  E  G  L  V  F  S  R  L  S  P  E  Y  Y  D  L  A
       250                             270                             290
AGAGCCCACCTGCGTGATGAGGAGAAATCCTGCCCGTGCCTGGCCCAGGAGGGCCCCCAG
R  A  H  L  R  D  E  E  K  S  C  P  C  L  A  Q  E  G  P  Q
       310                             330                             350
GGTGACCTGTTGACCAAAACACAGGAGCTGGGCCGTGACTACAGGACCTGTCTGACGATA
G  D  L  L  T  K  T  Q  E  L  G  R  D  Y  R  T  C  L  T  I
```

FIG. 2A

```
        370                 390                 410
GTCCAAAAACTGAAGAAGATGGTGGATAAGCCCACCCAGAGAAGTGTTTCCAATGCTGCG
V  Q  K  L  K  K  M  V  D  K  P  T  Q  R  S  V  S  N  A  A
        430                 450                 470
ACCCGGGTGTGTAGGACGGGGAGGTCACGATGGCGCGACGTCTGCAGAAATTTCATGAGG
T  R  V  C  R  T  G  R  S  R  W  R  D  V  C  R  N  F  M  R
        490                 510                 530
AGGTATCAGTCTAGAGTTACCCAGGGCCTCGTGGCCGGAGAAACTGCCCAGCAGATCTGT
R  Y  Q  S  R  V  T  Q  G  L  V  A  G  E  T  A  Q  Q  I  C
        550                 570                 590
GAGGACCTCAGGTTGTGTATACCTTCTACAGGTCCCCTCTGAGCCCTCTCACCTTGTCCT
E  D  L  R  L  C  I  P  S  T  G  P  L  *
        610                 630                 650
GTGGAAGAAGCACAGGCTCCTGTCCTCAGATCCCGGGAACCTCAGCAACCTCTGCCGGCT
        670                 690                 710
CCTCGCTTCCTCGATCCAGAATCCACTCTCCAGTCTCCCTCCCCTGACTCCCTCTGCTGT
        730                 750                 770
CCTCCCCTCTCACGAGAATAAAGTGTCAAGCAAGATTTTAGCCGCAGCTGCTTCTTCTTT
        790                 810                 830
GGTGGATTTGAGGGGTGGGTGTCAGTGGCATGCTGGGGTGAGCTGTGTAGTCCTTCAATA
        850                 870
AATGTCTGTCGTGTGTCCCATAAAAAAAAAAAAAAAAAAAAAAAAAA
```

FIG. 2B

HT3SG28 (SEQ ID NOS:5 and 6)

```
         10                            30                            50
CTCAGCGGCTGCCCCACCATGGCTACCTGGGCCCTCCTGCTCCTTGCAGCCATGCTCCTG
                  M  A  T  W  A  L  L  L  L  A  A  M  L  L
         70                            90                           110
GGCAACCCAGGTCTGGTCTTCTCTCGTCTGAGCCCTGAGTACTACGACCTGGCAAGAGCC
G  N  P  G  L  V  F  S  R  L  S  P  E  Y  Y  D  L  A  R  A
        130                           150                           170
CACCTGCGTGATGAGGAGAAATCCTGCCCGTGCCTGGCCCAGGAGGGCCCCCAGGGTGAC
H  L  R  D  E  E  K  S  C  P  C  L  A  Q  E  G  P  Q  G  D
        190                           210                           230
CTGTTGACCAAAACACAGGAGCTGGGCCGTGACTACAGGACCTGTCTGACGATAGTCCAA
L  L  T  K  T  Q  E  L  G  R  D  Y  R  T  C  L  T  I  V  Q
        250                           270                           290
AAACTGAAGAAGATGGTGGATAAGCCCACCCCAGGTCCCCTCTGAGCCCTCTCACCTTGT
K  L  K  K  M  V  D  K  P  T  P  G  P  L  *
```

FIG.3A

```
        310                 330                 350
CCTGTGGAAGAAGCACAGGCTCCTGTCCTCAGATCCCGGGAACCTCAGCAACCTCTGCCG
        370                 390                 410
GCTCCTCGCTTCCTCGATCCAGAATCCACTCTCCAGTCTCCCTCCCCTGACTCCCTCTGC
        430                 450                 470
TGTCCTCCCCTCTCACGAGAATAAAGTGTCAAGCCAGAAAAAAAAAAAAAAAAAAAAAAA
        490                 510                 530
AAAAAAAAAAAAAAAAAAAAAAAAAAAAAAAAAAAAAAAAAAAAAAAAAAAAAAAAAAAA
        550
AAAAAAAAAA
```

FIG. 3B

HBZAK03 (SEQ ID NOS:7 and 8)

```
        10                            30                            50
CGACCCACGCGTCCGGTTCGCTCTCTGGTAAGGGCGTGCAGGTGTTGGCCGCGGCCTCTG
        70                            90                           110
AGCTGGGATGAGCCGTGCTCCCGGTGGAAGCAAGGGAGCCCAGCCGGAGCCATGGCCAGT
                                                             M  A  S
       130                           150                           170
ACAGTGGTAGCAGTTGGACTGACCATTGCTGCTGCAGGATTTGCAGGCCGTTACGTTTTG
T  V  V  A  V  G  L  T  I  A  A  A  G  F  A  G  R  Y  V  L
       190                           210                           230
CAAGCCATGAAGCATATGGAGCCTCAAGTAAAACAAGTTTTTCAAAGCCTACCAAAATCT
Q  A  M  K  H  M  E  P  Q  V  K  Q  V  F  Q  S  L  P  K  S
       250                           270                           290
GCCTTCAGTGGTGGCTATTATAGAGCCCTACTGCCAATAAAGGGAAAATAAGAGATGCTC
A  F  S  G  G  Y  Y  R  A  L  L  P  I  K  G  K  *
       310                           330                           350
ATCGACGAATTATGCTTTTAAATCATCCTGACAAAGGAGGATCTCCTTATATAGCAGCCA
       370                           390                           410
AAATCAATGAAGCTAAAGATTTACTAGAAGGTCAAGCTAAAAAATGAAGTAAATGTATGA
       430                           450                           470
TGAATTTTAAGTTCGTATTAGTTTATGTATATGAGTACTAAGTTTTTATAATAAAATGCT
       490                           510
CCAGAGCTACAATTTTAACAAACAATTAAAAAAAAAAAAA
```

FIG. 4

HLFBD44 (SEQ ID NOS:9 and 10)

```
          10                            30                            50
CTGAGCTGGGATGAGCCGTGCTCCCGGTGGAAGCAAGGGAGCCCAGCCGGAGCCATGGCC
                                                          M  A
          70                            90                           110
AGTACAGTGGTAGCAGTTGGACTGACCATTGCTGCTGCAGGATTTGCAGGCCGTTACGTT
S  T  V  V  A  V  G  L  T  I  A  A  A  G  F  A  G  R  Y  V
         130                           150                           170
TTGCAAGCCATGAAGCATATGGAGCCTCAAGTAAAACAAGTTTTTCAAAGCCTACCAAAA
L  Q  A  M  K  H  M  E  P  Q  V  K  Q  V  F  Q  S  L  P  K
         190                           210                           230
TCTGCCTTCAGTGGTGGCTATTATAGAGGTGGGTTTGAACCCAAAATGACAAAACGGGAA
S  A  F  S  G  G  Y  Y  R  G  G  F  E  P  K  M  T  K  R  E
         250                           270                           290
GCAGCATTAATACTAGGTGTAAGCCCTACTGCCAATAAAGGGAAAATAAGAGATGCTCAT
A  A  L  I  L  G  V  S  P  T  A  N  K  G  K  I  R  D  A  H
         310                           330                           350
CGACGAATTATGCTTTTAAATCATCCTGACAAAGGAGGATCTCCTTATATAGCAGCCAAA
R  R  I  M  L  L  N  H  P  D  K  G  G  S  P  Y  I  A  A  K
         370                           390                           410
ATCAATGAAGCTAAAGATTTACTAGAAGGTCAAGCTAAAAAATGAAGTAAATGTATGATG
I  N  E  A  K  D  L  L  E  G  Q  A  K  K  *
```

FIG. 5A

```
        430                     450                     470
AATTTTAAGTTCGTATTAGTTTATGTATATGAGTACTAAGTTTTTATAATAAAATGCCTC
        490                     510                     530
AGAGCTACAATTTTAAAAAATGATTTAGCACAAGCTAAATCTCAAAGCCTTGGTATAATT
        550                     570                     590
TTCTTGTTTAAATTTGGGGATTTTAAATCAGATTATAGTTTAGAATATTTGCGTATTAAT
        610                     630                     650
TATGGGCAAGCACACACCTTCTGAATAGAAATATTGTTCATTACTCATTTAGCAGATAAT
        670                     690                     710
TTGGGACCTATGTCTACTTTTCAAGGCAAAGTGAAGATGACAGTCCTTGCTCTCAGGGAG
        730                     750                     770
CCCCCACTTTAATGGGAGACTGATAAACTGGTAATTAGACTGTGATAAATAGTATGATGG
        790                     810                     830
AAATTAGCTTAAGCTGTTTAAGTAGGGACTCTTCTTATTCGGTGGAAAGGCTGTTCCAGG
        850                     870                     890
TACAGGCAACTGGCCTGGCAACTTGGATACTTGGAACCTTGTATTTAAAAGTGAATTTAA
        910                     930                     950
CCACAACTGAGACCTAAGAAATTGACCTAGGGGTGTGTGTGTGTGTATTCTATGTACA
        970                     990                    1010
TATAAACCCATTTTTATTTCATGCATTAAAAATAGTATGATAAAGATTTCAGAGTACAGG
       1030                    1050                    1070
TCTGGTACAATCACAGTTCATTGCAGCCTCAACCTCCTGGGTTTAAGCAGTCCTCCCGCC
       1090                    1110                    1130
TCAGCCTCCCAAAGTACTGGGATTACAGGCATGAGTATTTACATTGTATTCAGCTAGCCC
```

FIG.5B

```
          1150                1170                1190
CTTAAAGGTAATGACCATTTATAAATTATTCCTTCAGTTGGCTATTTCTTGACATAATCA
          1210                1230                1250
AACTTCTGCAATTGTTATGATTAAGCTTAAACCCTGTTAGCAAAACTGAAAACTGAAATG
          1270                1290                1310
TTCTCAATATCAACATATTTAATTTGGACTCTTTAGAATTTATACACTAATAAATTTAAA
          1330                1350
TGATGTTTAAAGGCAAAAAAAAAAAAAAAAAA
```

FIG. 5C

HEBGM49 (SEQ ID NOS:11 and 12)

```
       10                            30                            50
CACGAGGCCCGGACCAGGCGCCTGTGCCTCCTCGTCCCTCGCCGCGTCCGCGAACCT
       70                            90                           110
GGAGCCGGCGGGAGCCCCGCGCTCGCCATGTCGGGCGAGCTCAGCAACAGGTTCCAAGGA
                                   M  S  G  E  L  S  N  R  F  Q  G
      130                           150                           170
GGGAAGGCGTTCGGCTTGCTCAAAGCCCGGCAGGAGAGGAGGCTGGCCGAGATCAACCGG
G  K  A  F  G  L  L  K  A  R  Q  E  R  R  L  A  E  I  N  R
      190                           210                           230
GAGTTTCTGTGTGACCAGAAGTACAGTGATGAAGAGAACCTTCCAGAAAAGCTCACAGCC
E  F  L  C  D  Q  K  Y  S  D  E  E  N  L  P  E  K  L  T  A
      250                           270                           290
TTCAAAGAGAAGTACATGGAGTTTGACCTGAACAATGAAGGCGAGATTGACCTGATGTCT
F  K  E  K  Y  M  E  F  D  L  N  N  E  G  E  I  D  L  M  S
      310                           330                           350
TTAAAGAGGATGATGGAGAAGCTTGGTGTCCCCAAGACCCACCTGGAGATGAAGAAGATG
L  K  R  M  M  E  K  L  G  V  P  K  T  H  L  E  M  K  K  M
      370                           390                           410
ATCTCAGAGGTGACAGGAGGGGTCAGTGACACTATATCCTACCGAGACTTTGTGAACATG
I  S  E  V  T  G  G  V  S  D  T  I  S  Y  R  D  F  V  N  M
```

FIG.6A

```
        430                           450                           470
ATGCTGGGGAAACGGTCGGCTGTCCTCAAGTTAGTCATGATGTTTGAAGGAAAAGCCAAC
M  L  G  K  R  S  A  V  L  K  L  V  M  M  F  E  G  K  A  N
        490                           510                           530
GAGAGCAGCCCCAAGCCAGTTGGCCCCCCTCCAGAGAGAGACATTGCTAGCCTGCCCTGA
E  S  S  P  K  P  V  G  P  P  P  E  R  D  I  A  S  L  P  *
        550                           570                           590
GGACCCCGCCTGGACTCCCCAGCCTTCCCACCCCATACCTCCCTCCCGATCTTGCTGCCC
        610                           630
TTCTTGACACACTGTGATCCGGCACGAGCGGC
```

FIG. 6B

HNGBH54 (SEQ ID NOS:13 and 14)

```
                    10         20         30          40         50         60
                     .          .          .           .          .          .
  1 ATG GGC AGC GCG GAC TGC GAG CTG AGC GCC AAG CTG CTG CGG CGC GCA GAC CTC AAC CAG  60
  1  M   G   S   A   D   C   E   L   S   A   K   L   L   R   R   A   D   L   N   Q   20

                    70         80         90         100        110        120
                     .          .          .           .          .          .
 61 GGC ATC GGC GAG CCC CAG TCG CCC AGC CGC CGC GTC TTC AAC CCC TAC ACC GAG TTC AAG 120
 21  G   I   G   E   P   Q   S   P   S   R   R   V   F   N   P   Y   T   E   F   K   40

                   130        140        150         160        170        180
                     .          .          .           .          .          .
121 GAG TTC TCC AGG AAG CAG ATC AAG GAC ATG GAG AAG ATG TTC AAG CAG TAT GAT GCC GGG 180
 41  E   F   S   R   K   Q   I   K   D   M   E   K   M   F   K   Q   Y   D   A   G   60

                   190        200        210         220        230        240
                     .          .          .           .          .          .
181 CGG GAC GGC TTC ATC GAC CTG ATG GAG CTA AAA CTC ATG ATG GAG AAA CTT GGG GCC CCT 240
 61  R   D   G   F   I   D   L   M   E   L   K   L   M   M   E   K   L   G   A   P   80

                   250        260        270         280        290        300
                     .          .          .           .          .          .
241 CAG ACC CAC CTG GGC CTG AAA AAC ATG ATC AAG GAG GTG GAT GAG GAC TTT GAC AGC AAG 300
 81  Q   T   H   L   G   L   K   N   M   I   K   E   V   D   E   D   F   D   S   K  100
```

FIG. 7A

```
                310         320         330         340         350         360
301 CTG AGC TTC CGG GAG TTC CTC CTG ATC TTC CGC AAG GCG GCG GCC GGG GAG CTT CAG GAG 360
101  L   S   F   R   E   F   L   L   I   F   R   K   A   A   A   G   E   L   Q   E  120

                370         380         390         400         410         420
361 GAC AGC GGG CTG TGC GTG CTG GCC CGC CTC TCT GAG ATC GAC GTC TCC AGT GAG GGT GTC 420
121  D   S   G   L   C   V   L   A   R   L   S   E   I   D   V   S   S   E   G   V  140

                430         440         450         460         470         480
421 AAG GGG GCC AAG AGC TTC TTT GAG GCC AAG GTC CAG GCC ATC AAC GTG TCC AGC CGC TTC 480
141  K   G   A   K   S   F   F   E   A   K   V   Q   A   I   N   V   S   S   R   F  160

                490         500         510         520         530         540
481 GAG GAG GAG ATC AAG GCA GAG CAG GAG GAA AGG AAG AAG CAG GCG GAG GAG ATG AAG CAG 540
161  E   E   E   I   K   A   E   Q   E   E   R   K   K   Q   A   E   E   M   K   Q  180

                550         560         570         580
541 CGG AAA GCG GCC TTC AAG GAG CTG CAG TCC ACC TTT AAG TAG 582
181  R   K   A   A   F   K   E   L   Q   S   T   F   K   *  193
```

FIG.7B

HSAAL25 (SEQ ID NOS:15 and 16)

```
          10                  30                  50
ACATATTTACATTTGATTTAACAGTGAACCTTAATTCTTTCTGGCTTCACAGTGAAACAA
          70                  90                 110
GTTTATGCAATCGATCAAATATTTTCATCCCTGAGGTTAACAATTACCATCAAAATGTTT
                                                       M  F
         130                 150                 170
TGTGGAGACTATGTGCAAGGAACCATCTTCCCAGCTCCCAATTTCAATCCCATAATGGAT
C  G  D  Y  V  Q  G  T  I  F  P  A  P  N  F  N  P  I  M  D
         190                 210                 230
GCCCAAATGCTAGGAGGAGCACTCCAAGGATTTGACTGTGACAAAGACATGCTGATCAAC
A  Q  M  L  G  G  A  L  Q  G  F  D  C  D  K  D  M  L  I  N
         250                 270                 290
ATTCTGACTCAGCGCTGCAATGCACAAAGGATGATGATTGCAGAGGCATACCAGAGCATG
I  L  T  Q  R  C  N  A  Q  R  M  M  I  A  E  A  Y  Q  S  M
         310                 330                 350
TATGGCCGGGACCTGATTGGGGATCTGAGGGAGCAGCTTTCGGATCACTTCAAAGATGTG
Y  G  R  D  L  I  G  D  L  R  E  Q  L  S  D  H  F  K  D  V
         370                 390                 410
ATGGCTGGCCTCATGTACCCACCACCACTGTATGATGCTCATGAGCTCTGGCATGCCATG
M  A  G  L  M  Y  P  P  P  L  Y  D  A  H  E  L  W  H  A  M
```

FIG. 8A

```
     430                           450                           470
AAGGGAGTAGGCACTGATGAGAATTGCCTCATTGAAATACTAGCTTCAAGAACAAATGGA
K  G  V  G  T  D  E  N  C  L  I  E  I  L  A  S  R  T  N  G
     490                           510                           530
GAAATTTTCCAGATGCGAGAAGCCTACTGCTTGCAATACAGCAATAACCTCCAAGAGGAC
E  I  F  Q  M  R  E  A  Y  C  L  Q  Y  S  N  N  L  Q  E  D
     550                           570                           590
ATTTATTCAGAGACCTCGGGACACTTCAGAGATACTCTCATGAACTTGGTCCAGGGGACC
I  Y  S  E  T  S  G  H  F  R  D  T  L  M  N  L  V  Q  G  T
     610                           630                           650
AGAGAGGAAGGATATACAGACCCTGCGATGGCTGCTCAGGATGCAATGGTCCTATGGGAA
R  E  E  G  Y  T  D  P  A  M  A  A  Q  D  A  M  V  L  W  E
     670                           690                           710
GCCTGTCAGCAGAAGACGGGGGAGCACAAAACCATGCTGCAAATGATCCTGTGCAACAAG
A  C  Q  Q  K  T  G  E  H  K  T  M  L  Q  M  I  L  C  N  K
     730                           750                           770
AGCTACCAGCAGCTGCGGCTGGTTTTCCAGGAATTTCAAAATATTTCTGGGCAAGATATG
S  Y  Q  Q  L  R  L  V  F  Q  E  F  Q  N  I  S  G  Q  D  M
     790                           810                           830
GTAGATGCCATTAATGAATGTTATGATGGATACTTTCAGGAGCTGCTGGTTGCAATTGTT
V  D  A  I  N  E  C  Y  D  G  Y  F  Q  E  L  L  V  A  I  V
     850                           870                           890
CTCTGTGTTCGAGACAAACCAGCCTATTTTGCTTATAGATTATATAGTGCAATTCATGAC
L  C  V  R  D  K  P  A  Y  F  A  Y  R  L  Y  S  A  I  H  D
```

FIG.8B

```
     910                           930                           950
TTTGGTTTCCATAATAAAACTGTAATCAGGATTCTCATTGCCAGAAGTGAAATAGACCTG
F  G  F  H  N  K  T  V  I  R  I  L  I  A  R  S  E  I  D  L
     970                           990                          1010
CTGACCATAAGGAAACGATACAAAGAGCGATATGGAAAATCCCTATTTCATGATATCAGA
L  T  I  R  K  R  Y  K  E  R  Y  G  K  S  L  F  H  D  I  R
    1030                          1050                          1070
AATTTTGCTTCAGGGCATTATAAGAAAGCACTGCTTGCCATCTGTGCTGGTGATGCTGAG
N  F  A  S  G  H  Y  K  K  A  L  L  A  I  C  A  G  D  A  E
    1090                          1110                          1130
GACTACTAAAATGAAGAGGACTTGGAGTACTGTGCACTCCTCTTTCTAGACACTTCCAAA
D  Y  *

    1150                          1170                          1190
TAGAGATTTTCTCACAAATTTGTACTGTTCATGGCACTATTAACAAAACTATACAATCAT
    1210                          1230                          1250
ATTTTCTCTTCTATCTTTGAAATTATTCTAAGCCAAAGAAAACTATGAATGAAAGTATAT
    1270                          1290                          1310
GATACTGAATTTGCCTACTATCCTGAATTTGCCTACTATCTAATCAGCAATTAAATAAAT
    1330                          1350
TGTGCATGATGGAATAATAAAAAAAAAAAAAAAAAA
```

FIG. 8C

HUSAX55 (SEQ ID NOS:17 and 18)

```
                10        20        30        40        50        60
                 .         .         .         .         .         .
  1 ATGGATATTTACGACACTCAAACCTTGGGGGTTGTGGTCTTTGGAGGATTCATGGTTGTT 60
  1  M  D  I  Y  D  T  Q  T  L  G  V  V  V  F  G  G  F  M  V  V  20

                70        80        90       100       110       120
                 .         .         .         .         .         .
 61 TCTGCCATTGGCATCTTCCTGGTGTCGACTTTCTCCATGAAGGAAACGTCATATGAAGAA 120
 21  S  A  I  G  I  F  L  V  S  T  F  S  M  K  E  T  S  Y  E  E  40

               130       140       150       160       170       180
                 .         .         .         .         .         .
121 GCCCTAGCCAACCAGCGCAAGGAGATGGCGAAAACTCACCACCAGAAAGTCGAGAAGAAA 180
 41  A  L  A  N  Q  R  K  E  M  A  K  T  H  H  Q  K  V  E  K  K  60

               190       200       210       220       230       240
                 .         .         .         .         .         .
181 AAGAAGGAGAAAACAGTGGAGAAGAAAGGAAAGACCAAGAAAAAGGAAGAGAAACCTAAT 240
 61  K  K  E  K  T  V  E  K  K  G  K  T  K  K  K  E  E  K  P  N  80
```

FIG.9A

```
                 250        260        270        280        290        300
                   .          .          .          .          .          .
241  GGGAAGATACCTGATCATGATCCAGCCCCCAATGTGACTGTCCTCCTTCGAGAACCAGTG  300
 81   G  K  I  P  D  H  D  P  A  P  N  V  T  V  L  L  R  E  P  V   100

                 310        320        330        340        350        360
                   .          .          .          .          .          .
301  CGGGCTCCTGCTGTGGCTGTGGCTCCAACCCCAGTGCAGCCCCCATTATCGTTGCTCCT  360
101   R  A  P  A  V  A  V  A  P  T  P  V  Q  P  P  I  I  V  A  P   120

                 370        380        390        400        410        420
                   .          .          .          .          .          .
361  GTCGCCACAGTTCCAGCCATGCCCCAGGAGAAGCTGGCCTCCTCCCCCAAGGACAAAAAG  420
121   V  A  T  V  P  A  M  P  Q  E  K  L  A  S  S  P  K  D  K  K   140

                 430        440        450        460        470        480
                   .          .          .          .          .          .
421  AAGAAGGAGAAAAAAGTGGCAAAAGTGGAACCAGCTGTCAGCTCTGTAGTGAATTCCATC  480
141   K  K  E  K  K  V  A  K  V  E  P  A  V  S  S  V  V  N  S  I   160
```

FIG.9B

```
          490       500       510       520       530       540
            .         .         .         .         .         .
481  CAGGTTCTCACTTCGAAGGCTGCCATCTTGGAAACTGCTCCCAAGGAGGGCAGAAATACA  540
161   Q  V  L  T  S  K  A  A  I  L  E  T  A  P  K  E  G  R  N  T   180

          550       560       570       580       590       600
            .         .         .         .         .         .
541  GATGTGGCCCAGAGCCCAGAGGCACCAAAGCAAGAGGCTCCTGCCAAGAAGAAGTCTGGT  600
181   D  V  A  Q  S  P  E  A  P  K  Q  E  A  P  A  K  K  K  S  G   200

          610       620       630       640       650       660
            .         .         .         .         .         .
601  TCAAAGAAAAAAGGGCCCCCAGATGCCGACGGCCCTCTCTACCTCCCCTACAAGACGCTG  660
201   S  K  K  K  G  P  P  D  A  D  G  P  L  Y  L  P  Y  K  T  L   220

          670       680       690       700       710       720
            .         .         .         .         .         .
661  GTCTCCACGGTTGGGAGCATGGTGTTCAACGAGGGCGAGGCCCAGCGGCTCATCGAGATC  720
221   V  S  T  V  G  S  M  V  F  N  E  G  E  A  Q  R  L  I  E  I   240
```

FIG. 9C

```
                 730       740       750       760       770       780
                   .         .         .         .         .         .
721  CTGTCTGAGAAGGCTGGCATCATTCAGGACACCTGGCACAAGGCCACTCAGAAGGGTGAC  780
241   L  S  E  K  A  G  I  I  Q  D  T  W  H  K  A  T  Q  K  G  D   260

                 790       800       810       820       830       840
                   .         .         .         .         .         .
781  CCTGTGGCGATTCTGAAACGCCAGCTGGAAGAGAAGGAAAAACTGCTGGCCACAGAACAG  840
261   P  V  A  I  L  K  R  Q  L  E  E  K  E  K  L  L  A  T  E  Q   280

                 850       860       870       880       890       900
                   .         .         .         .         .         .
841  GAAGATGCGGCTGTCGCCAAGAGCAAACTGAGGGAGCTCAACAAGGAGATGGCAGCAGAA  900
281   E  D  A  A  V  A  K  S  K  L  R  E  L  N  K  E  M  A  A  E   300

                 910       920       930       940       950       960
                   .         .         .         .         .         .
901  AAGGCCAAAGCAGCAGCCGGGGAGGCCAAAGTGAAAAAGCAGCTGGTGGCCCGGGAGCAG  960
301   K  A  K  A  A  A  G  E  A  K  V  K  K  Q  L  V  A  R  E  Q   320
```

FIG. 9D

```
                970       980       990      1000      1010      1020
                  .         .         .         .         .         .
 961 GAGATCACGGCTGTGCAGGCACGCATGCAGGCCAGCTACCGGGAGCACGTGAAGGAGGTG 1020
 321  E  I  T  A  V  Q  A  R  M  Q  A  S  Y  R  E  H  V  K  E  V  340

               1030      1040      1050      1060      1070      1080
                  .         .         .         .         .         .
1021 CAGCAGCTGCAGGGCAAGATCCGGACTCTTCAGGAGCAGCTGGAGAATGGCCCCAACACG 1080
 341  Q  Q  L  Q  G  K  I  R  T  L  Q  E  Q  L  E  N  G  P  N  T  360

               1090      1100      1110      1120      1130      1140
                  .         .         .         .         .         .
1081 CAGCTGGCCCGCCTGCAGCAGGAGAACTCCATCCTGCGGGATGCCTTGAACCAGGCCACG 1140
 361  Q  L  A  R  L  Q  Q  E  N  S  I  L  R  D  A  L  N  Q  A  T  380

               1150      1160      1170      1180      1190      1200
                  .         .         .         .         .         .
1141 AGCCAGGTGGAGAGCAAGCAGAACGCAGAGCTGGCCAAGCTTCGGCAGGAGCTCAGCAAG 1200
 381  S  Q  V  E  S  K  Q  N  A  E  L  A  K  L  R  Q  E  L  S  K  400

               1210      1220      1230      1240      1250      1260
                  .         .         .         .         .         .
1201 GTCAGCAAAGAGCTGGTGGAGAAGTCAGAGGCTGTGCGGCAAGATGAGCAGCAGCGGAAA 1260
 401  V  S  K  E  L  V  E  K  S  E  A  V  R  Q  D  E  Q  Q  R  K  420
```

FIG. 9E

```
                1270      1280      1290      1300      1310      1320
                   .         .         .         .         .         .
1261 GCTCTGGAAGCCAAGGCAGCTGCCTTCGAGAAGCAGGTCCTGCAGCTGCAGGCGTCCCAC 1320
421   A  L  E  A  K  A  A  A  F  E  K  Q  V  L  Q  L  Q  A  S  H  440

                1330      1340      1350      1360      1370      1380
                   .         .         .         .         .         .
1321 AGGGAGAGTGAGGAGGCCCTGCAGAAGCGCCTGGACGAGGTCAGCCGGGAGCTGTGCCAC 1380
441   R  E  S  E  E  A  L  Q  K  R  L  D  E  V  S  R  E  L  C  H  460

                1390      1400      1410      1420      1430      1440
                   .         .         .         .         .         .
1381 ACGCAGAGCAGCCACGCCAGCCTCCGGGCGGATGCCGAGAAGGCCCAGGAGCAACAGCAG 1440
461   T  Q  S  S  H  A  S  L  R  A  D  A  E  K  A  Q  E  Q  Q  Q  480

                1450      1460      1470      1480      1490      1500
                   .         .         .         .         .         .
1441 CAGATGGCCGAGCTGCACAGCAAGTTACAGTCCTCCGAGGCGGAGGTGCGCAGCAAATGC 1500
481   Q  M  A  E  L  H  S  K  L  Q  S  S  E  A  E  V  R  S  K  C  500
```

FIG. 9F

```
          1510      1520      1530      1540      1550      1560
1501 GAGGAGCTGAGTGGCCTCCACGGGCAGCTCCAGGAGGCCAGGGCAGAGAACTCCCAGCTC 1560
 501 E  E  L  S  G  L  H  G  Q  L  Q  E  A  R  A  E  N  S  Q  L  520

          1570      1580      1590      1600      1610      1620
1561 ACAGAGAGAATCCGTTCCATTGAGGCCCTGCTGGAGGCGGGCCAGGCGCGGGATGCCCAG 1620
 521 T  E  R  I  R  S  I  E  A  L  L  E  A  G  Q  A  R  D  A  Q  540

          1630      1640      1650      1660      1670      1680
1621 GACGTCCAGGCCAGCCAGGCGGAGGCTGACCAGCAGCAGACTCGCCTCAAGGAGCTGGAG 1680
 541 D  V  Q  A  S  Q  A  E  A  D  Q  Q  Q  T  R  L  K  E  L  E  560

1690      1700      1710      1720      1730      1740
1681 TCCCAGGTGTCGGGTCTGGAGAAGGAGGCCATCGAGCTCAGGGAGGCCGTCGAGCAGCAG 1740
 561 S  Q  V  S  G  L  E  K  E  A  I  E  L  R  E  A  V  E  Q  Q  580

          1750      1760      1770      1780      1790      1800
1741 AAAGTGAAGAACAATGACCTCCGGGAGAAGAACTGGAAGGCCATGGAGGCACTGGCCACG 1800
 581 K  V  K  N  N  D  L  R  E  K  N  W  K  A  M  E  A  L  A  T  600
```

FIG.9G

```
               1810      1820      1830      1840      1850      1860
                  .         .         .         .         .         .
1801 GCCGAGCAGGCCTGCAAGGAGAAGCTGCACTCCCTGACCCAGGCCAAGGAGGAATCGGAG 1860
 601  A  E  Q  A  C  K  E  K  L  H  S  L  T  Q  A  K  E  E  S  E  620

               1870      1880      1890      1900      1910      1920
                  .         .         .         .         .         .
1861 AAGCAGCTCTGTCTGATTGAGGCGCAGACCATGGAGGCCCTGCTGGCTCTGCTCCCAGAA 1920
 621  K  Q  L  C  L  I  E  A  Q  T  M  E  A  L  L  A  L  L  P  E  640
               1930      1940      1950      1960      1970      1980
                  .         .         .         .         .         .
1921 CTCTCTGTCTTGGCACAACAGAATTACACCGAGTGGCTGCAGGATCTCAAAGAGAAAGGC 1980
 641  L  S  V  L  A  Q  Q  N  Y  T  E  W  L  Q  D  L  K  E  K  G  660

               1990      2000      2010      2020      2030      2040
             .         .         .         .         .
1981 CCCACGCTGCTGAAGCACCCGCCAGCTCCCGCGGAGCCCTCCTCGGACCTGGCCTCCAAG 2040
 661  P  T  L  L  K  H  P  P  A  P  A  E  P  S  S  D  L  A  S  K  680

               2050      2060      2070      2080      2090      2100
                  .         .         .         .         .         .
2041 TTGAGGGAGGCCGAGGAGACGCAGAGCACACTGCAGGCCGAGTGTGACCAGTACCGCAGC 2100
 681  L  R  E  A  E  E  T  Q  S  T  L  Q  A  E  C  D  Q  Y  R  S  700
```

FIG. 9H

```
                2110      2120      2130      2140      2150      2160
                   .         .         .         .         .         .
2101 ATCCTGGCGGAGACGGAGGGCATGCTCAGAGACCTGCAGAAGAGCGTGGAGGAGGAGGAG 2160
 701  I  L  A  E  T  E  G  M  L  R  D  L  Q  K  S  V  E  E  E  E  720

                2170      2180      2190      2200      2210      2220
                   .         .         .         .         .         .
2161 CAGGTGTGGAGGGCCAAGGTGGGCGCCGCAGAGGAGGAGCTCCAGAAGTCCCGGGTCACA 2220
 721  Q  V  W  R  A  K  V  G  A  A  E  E  E  L  Q  K  S  R  V  T  740

                2230      2240      2250      2260      2270      2280
                   .         .         .         .         .         .
2221 GTGAAGCATCTCGAAGAGATTGTAGAGAAGCTAAAAGGAGAACTTGAAAGTTCGGACCAG 2280
 741  V  K  H  L  E  E  I  V  E  K  L  K  G  E  L  E  S  S  D  Q  760

                2290      2300      2310      2320      2330      2340
                   .         .         .         .         .         .
2281 GTGAGGGAGCACACGTCGCATTTGGAGGCAGAGCTGGAAAAGCACATGGCGGCCGCCAGC 2340
 761  V  R  E  H  T  S  H  L  E  A  E  L  E  K  H  M  A  A  A  S  780

                2350      2360      2370      2380      2390      2400
                   .         .         .         .         .         .
2341 GCCGAGTGCCAGAACTACGCCAAGGAGGTGGCAGGGCTGAGGCAACTTCTCCTAGAATCT 2400
 781  A  E  C  Q  N  Y  A  K  E  V  A  G  L  R  Q  L  L  L  E  S  800
```

FIG. 9I

```
          2410      2420      2430      2440      2450      2460
2401 CAATCTCAGCTCGATGCCGCCAAGAGCGAAGCCCAGAAACAGAGCGATGAGCTTGCCCTG 2460
801   Q  S  Q  L  D  A  A  K  S  E  A  Q  K  Q  S  D  E  L  A  L  820

          2470      2480      2490      2500      2510      2520
2461 GTCAGGCAGCAGTTGAGTGAAATGAAGAGCCACGTAGAGGATGGTGACATAGCTGGGGCC 2520
821   V  R  Q  Q  L  S  E  M  K  S  H  V  E  D  G  D  I  A  G  A  840

          2530      2540      2550      2560      2570      2580
2521 CCAGCTTCCTCCCCAGAGGCGCCCCCAGCCGAGCAGGACCCCGTTCAGCTGAAGACGCAG 2580
841   P  A  S  S  P  E  A  P  P  A  E  Q  D  P  V  Q  L  K  T  Q  860

          2590      2600      2610      2620      2630      2640
2581 CTGGAGTGGACAGAAGCCATCCTGGAGGATGAGCAGACACAGCGGCAGAAGCTCATGGCC 2640
861   L  E  W  T  E  A  I  L  E  D  E  Q  T  Q  R  Q  K  L  M  A  880

          2650      2660      2670      2680      2690      2700
2641 GAGTTTGAGGAGGCTCAGACCTCGGCATGTCGGTTACAAGAAGAATTGGAGAAGCTCCGC 2700
881   E  F  E  E  A  Q  T  S  A  C  R  L  Q  E  E  L  E  K  L  R  900
```

FIG. 9J

```
               2710      2720      2730      2740      2750      2760
                  .         .         .         .         .         .
2701 ACAGCCGGCCCCCTAGAGTCTTCAGAAACAGAGGAGGCCTCACAGCTGAAGGAGAGACTA 2760
901   T  A  G  P  L  E  S  S  E  T  E  E  A  S  Q  L  K  E  R  L  920

               2770      2780      2790      2800      2810      2820
                  .         .         .         .         .         .
2761 GAAAAAGAGAAGAAGTTAACAAGTGACCTGGGGCGCGCCGCCACGAGACTGCAGGAGCTT 2820
921   E  K  E  K  K  L  T  S  D  L  G  R  A  A  T  R  L  Q  E  L  940

               2830      2840      2850      2860      2870      2880
                  .         .         .         .         .         .
2821 CTGAAGACGACCCAGGAGCAGCTGGCAAGGGAGAAGGACACGGTGAAGAAGCTGCAGGAA 2880
941   L  K  T  T  Q  E  Q  L  A  R  E  K  D  T  V  K  K  L  Q  E  960

               2890      2900      2910      2920      2930
                  .         .         .         .         .
2881 CAGCTGGAAAAGGCAGAGGACGGCAGCAGCTCAAAGGAGGGCACCTCTGTCTGA 2934
961   Q  L  E  K  A  E  D  G  S  S  S  K  E  G  T  S  V  *  977
```

FIG. 9K

HSXCK41 (SEQ ID NOS:19 and 20)

```
                10        20        30        40        50        60
                 .         .         .         .         .         .
  1 ATGGCCCAGCTGTTCCTGCCCCTGCTGGCAGCCCTGGTCCTGGCCCAGGCTCCTGCAGCT 60
  1  M  A  Q  L  F  L  P  L  L  A  A  L  V  L  A  Q  A  P  A  A  20

                70        80        90       100       110       120
                 .         .         .         .         .         .
 61 TTAGCAGATGTTCTGGAAGGAGACAGCTCAGAGGACCGCGCTTTTCGCGTGCGCATCGCG 120
 21  L  A  D  V  L  E  G  D  S  S  E  D  R  A  F  R  V  R  I  A  40
               130       140       150       160       170       180
                 .         .         .         .         .         .
121 GGCGACGCGCCACTGCAGGGCGTGCTCGGCGGCGCCCTCACCATCCCTTGCCACGTCCAC 180
 41  G  D  A  P  L  Q  G  V  L  G  G  A  L  T  I  P  C  H  V  H  60

               190       200       210       220       230       240
                 .         .         .         .         .         .
181 TACCTGCGGCCACCGCCGAGCCGCCGGGCTGTGCTGGGCTCTCCGCGGGTCAAGTGGACT 240
 61  Y  L  R  P  P  P  S  R  R  A  V  L  G  S  P  R  V  K  W  T  80
```

FIG. 10A

```
                250         260         270         280         290         300
                  .           .           .           .           .           .
241  TTCCTGTCCCGGGGCCGGGAGGCAGAGGTGCTGGTGGCGCGGGGAGTGCGCGTCAAGGTG 300
 81   F  L  S  R  G  R  E  A  E  V  L  V  A  R  G  V  R  V  K  V  100

                310         320         330         340         350         360
                  .           .           .           .           .           .
301  AACGAGGCCTACCGGTTCCGCGTGGCACTGCCTGCGTACCCAGCGTCGCTCACCGACGTC 360
101   N  E  A  Y  R  F  R  V  A  L  P  A  Y  P  A  S  L  T  D  V  120

                370         380         390         400         410         420
                  .           .           .           .           .           .
361  TCCCTGGCGCTGAGCGAGCTGCGCCCCAACGACTCAGGTATCTATCGCTGTGAGGTCCAG 420
121   S  L  A  L  S  E  L  R  P  N  D  S  G  I  Y  R  C  E  V  Q  140

                430         440         450         460         470         480
                  .           .           .           .           .           .
421  CACGGCATCGATGACAGCAGCGACGCTGTGGAGTCAAGTCAAAGGTATCCCATCCAGACC 480
141   H  G  I  D  D  S  S  D  A  V  E  S  S  Q  R  Y  P  I  Q  T  160

                490         500         510         520         530         540
                  .           .           .           .           .           .
481  CCACGAGAGGCCTGTTACGGAGACATGGATGGCTTCCCCGGGGTCCGGAACTATGGTGTG 540
161   P  R  E  A  C  Y  G  D  M  D  G  F  P  G  V  R  N  Y  G  V  180
```

FIG. 10B

```
                550       560       570       580       590       600
                  .         .         .         .         .         .
541 GTGGACCCGGATGACCTCTATGATGTGTACTGTTATGCTGAAGACCTAAATGGAGAACTG 600
181  V  D  P  D  D  L  Y  D  V  Y  C  Y  A  E  D  L  N  G  E  L  200

                610       620       630       640       650       660
                  .         .         .         .         .         .
601 TTCCTGGGTGACCCTCCAGAGAAGCTGACATTGGAGGAAGCACGGGCGTACTGCCAGGAG 660
201  F  L  G  D  P  P  E  K  L  T  L  E  E  A  R  A  Y  C  Q  E  220

                670       680       690       700       710       720
                  .         .         .         .         .         .
661 CGGGGTGCAGAGATTGCCACCACGGGCCAACTGTATGCAGCCTGGGATGGTGGCCTGGAC 720
221  R  G  A  E  I  A  T  T  G  Q  L  Y  A  A  W  D  G  G  L  D  240

                730       740       750       760       770       780
                  .         .         .         .         .         .
721 CACTGCAGCCCAGGGTGGCTAGCTGATGGCAGTGTGCGCTACCCCATCGTCACACCCAGC 780
241  H  C  S  P  G  W  L  A  D  G  S  V  R  Y  P  I  V  T  P  S  260
```

FIG. 10C

```
                790         800         810         820         830         840
                  .           .           .           .           .           .
781  CAGCGCTGTGGTGGGGGCTTGCCTGGTGTCAAGACTCTCTTCCTCTTCCCCAACCAGACT 840
261   Q  R  C  G  G  G  L  P  G  V  K  T  L  F  L  F  P  N  Q  T  280

                850         860         870         880         890         900
                  .           .           .           .           .           .
841  GGCTTCCCCAATAAGCACAGCCGCTTCAACGTCTACTGCTTCCGAGACTCGGCCCAGCTT 900
281   G  F  P  N  K  H  S  R  F  N  V  Y  C  F  R  D  S  A  Q  L  300

                910         920         930         940         950         960
                  .           .           .           .           .           .
901  CTGCCATCCCTGAGGCCTCCAACCCAGCCTCCAACCCAGCTTGATGGACTAGAGGCTATC 960
301   L  P  S  L  R  P  P  T  Q  P  P  T  Q  L  D  G  L  E  A  I  320

                970         980         990        1000        1010        1020
                  .           .           .           .           .           .
961  GTCACAGTGACAGAGACCCTGGAGGAACTGCAGCTGCCTCAGGAAGCCACAGAGAGTGAA 1020
321   V  T  V  T  E  T  L  E  E  L  Q  L  P  Q  E  A  T  E  S  E  340

               1030        1040        1050        1060        1070        1080
                  .           .           .           .           .           .
1021 TCCCGTGGGGCCATCTACTCCATCCCCATCATGGAGGACGGAGGAGGTGGAAGCTCCACT 1080
341   S  R  G  A  I  Y  S  I  P  I  M  E  D  G  G  G  G  S  S  T  360
```

FIG.10D

```
                1090      1100      1110      1120      1130      1140
                   .         .         .         .         .         .
1081 CCAGAAGACCCAGCAGAGGCCCCTAGGACGCTCCTAGAATTTGAAACACAATCCATGGTA 1140
 361  P  E  D  P  A  E  A  P  R  T  L  L  E  F  E  T  Q  S  M  V  380

                1150      1160      1170      1180      1190      1200
                   .         .         .         .         .         .
1141 CCGCCCACGGGGTTTTCAGAAGAGGAAGGTAAGGCATTGGAGGAAGAAGAGAAATATGAA 1200
 381  P  P  T  G  F  S  E  E  E  G  K  A  L  E  E  E  E  K  Y  E  400

                1210      1220      1230      1240      1250      1260
                   .         .         .         .         .         .
1201 GATGAAGAAGAGAAAGAGGAGGAAGAAGAAGAGGAGGAGGTGGAGGATGAGGCTCTGTGG 1260
 401  D  E  E  E  K  E  E  E  E  E  E  E  E  V  E  D  E  A  L  W  420

                1270      1280      1290      1300      1310      1320
                   .         .         .         .         .         .
1261 GCATGGCCCAGCGAGCTCAGCAGCCCGGGCCCTGAGGCCTCTCTCCCCACTGAGCCAGCA 1320
 421  A  W  P  S  E  L  S  S  P  G  P  E  A  S  L  P  T  E  P  A  440

                1330      1340      1350      1360      1370      1380
                   .         .         .         .         .         .
1321 GCCCAGGAGGAGTCACTCTCCCAGGCGCCAGCAAGGGCAGTCCTGCAGCCTGGTGCATCA 1380
 441  A  Q  E  E  S  L  S  Q  A  P  A  R  A  V  L  Q  P  G  A  S  460
```

FIG.10E

```
                 1390       1400       1410       1420       1430       1440
                    .          .          .          .          .          .
1381 CCACTTCCTGATGGAGAGTCAGAAGCTTCCAGGCCTCCAAGGGTCCATGGACCACCTACT 1440
 461  P  L  P  D  G  E  S  E  A  S  R  P  P  R  V  H  G  P  P  T  480

                 1450       1460       1470       1480       1490       1500
                    .          .          .          .          .          .
1441 GAGACTCTGCCCACTCCCAGGGAGAGGAACCTAGCATCCCCATCACCTTCCACTCTGGTT 1500
 481  E  T  L  P  T  P  R  E  R  N  L  A  S  P  S  P  S  T  L  V  500

                 1510       1520       1530       1540       1550       1560
                    .          .          .          .          .          .
1501 GAGGCAAGAGAGGTGGGGGAGGCAACTGGTGGTCCTGAGCTATCTGGGGTCCCTCGAGGG 1560
 501  E  A  R  E  V  G  E  A  T  G  G  P  E  L  S  G  V  P  R  G  520

                 1570       1580
                    .          .
1561 GGGGCCCGTACCCAATTCGCCCTATAG 1587
 521  G  A  R  T  Q  F  A  L  *  528
```

FIG.10F

HFKFY79 (SEQ ID NOS:21 and 22)

```
                   10         20         30         40         50         60
                    .          .          .          .          .          .
  1 ATGTCTGCCGACGGGGCAGAGGCTGATGGCAGCACCCAGGTGACAGTGGAAGAACCGGTA 60
  1  M  S  A  D  G  A  E  A  D  G  S  T  Q  V  T  V  E  E  P  V  20

                   70         80         90        100        110        120
                    .          .          .          .          .          .
 61 CAGCAGCCCAGTGTGGTGGACCGTGTGGCCAGCATGCCTCTGATCAGCTCCACCTGCGAC 120
 21  Q  Q  P  S  V  V  D  R  V  A  S  M  P  L  I  S  S  T  C  D  40

                  130        140        150        160        170        180
                    .          .          .          .          .          .
121 ATGGTGTCCGCAGCCTATGCCTCCACCAAGGAGAGCTACCCGCACGTCAAGACTGTCTGC 180
 41  M  V  S  A  A  Y  A  S  T  K  E  S  Y  P  H  V  K  T  V  C  60

                  190        200        210        220        230        240
                    .          .          .          .          .          .
181 GACGCAGCAGAGAAGGGAGTGAGGACCCTCACGGCGGCTGCTGTCAGCGGGGCTCAGCCG 240
 61  D  A  A  E  K  G  V  R  T  L  T  A  A  A  V  S  G  A  Q  P  80
```

FIG.11A

```
                250       260       270       280       290       300
                  .         .         .         .         .         .
241  ATCCTCTCCAAGCTGGAGCCCCAGATTGCATCAGCCAGCGAATACGCCCACAGGGGGCTG  300
 81   I  L  S  K  L  E  P  Q  I  A  S  A  S  E  Y  A  H  R  G  L   100

                310       320       330       340       350       360
                  .         .         .         .         .         .
301  GACAAGTTGGAGGAGAACCTCCCCATCCTGCAGCAGCCCACGGAGAAGTCCTGGCGGACA  360
101   D  K  L  E  E  N  L  P  I  L  Q  Q  P  T  E  K  S  W  R  T   120

                370       380       390       400       410       420
                  .         .         .         .         .         .
361  CAACGACTTGTGTCGTCTAAAGTGTCGGGGCCCAAGAAATGGTGTCTAGCGCCAACGACA  420
121   Q  R  L  V  S  S  K  V  S  G  P  K  K  W  C  L  A  P  T  T   140

                430       440       450       460       470       480
                  .         .         .         .         .         .
421  CGGTGGCCACCAATTGTCGGAGCGGTGGACGCGACCCGCGGTGCTGTGCAGAGCGGCGTG  480
141   R  W  P  P  I  V  G  A  V  D  A  T  R  G  A  V  Q  S  G  V   160

                490       500       510       520       530       540
                  .         .         .         .         .         .
481  GACAAGACAAAGTCCGTAGTGACCGGCGGCGTCCAATCGGTCATGGGCTCCCGCTTGGGC  540
161   D  K  T  K  S  V  V  T  G  G  V  Q  S  V  M  G  S  R  L  G   180
```

FIG.11B

```
                550       560       570       580       590       600
                  .         .         .         .         .         .
541  GGCACGAGGCTGAGTGGGGTCGACACGGTGCTGGGAAGTCGGAGGAGTGGGCGGACAAC  600
181   G  T  R  L  S  G  V  D  T  V  L  G  K  S  E  E  W  A  D  N   200

                610       620       630       640       650       660
                  .         .         .         .         .         .
601  CACCTGCCCCTTACGGATGCCGAACTGGCCCGCATCGCCACATCCCTGGATGGCTTCGAC  660
201   H  L  P  L  T  D  A  E  L  A  R  I  A  T  S  L  D  G  F  D   220

                670       680       690       700       710       720
                  .         .         .         .         .         .
661  GTCGCGTCCGTGCAGCAGCAGCGGCAGGAACAGAGCTACTTCGTACGTCTGGGCTCCCTG  720
221   V  A  S  V  Q  Q  Q  R  Q  E  Q  S  Y  F  V  R  L  G  S  L   240

                730       740       750       760       770       780
                  .         .         .         .         .         .
721  TCGGAGAGGCTGCGGCAGCACGCCTATGAGCACTCGCTGGGCAAGCTTCGAGCCACCAAG  780
241   S  E  R  L  R  Q  H  A  Y  E  H  S  L  G  K  L  R  A  T  K   260
```

FIG.11C

```
               790       800       810       820       830       840
                 .         .         .         .         .         .
 781 CAGAGGGCACAGGAGGCTCTGCTGCAGCTGTCGCAGGCCCTAAGCCTGATGGAAACTGTC 840
 261  Q  R  A  Q  E  A  L  L  Q  L  S  Q  A  L  S  L  M  E  T  V  280

               850       860       870       880       890       900
                 .         .         .         .         .         .
 841 AAGCAAGGCGTTGATCAGAAGCTGGTGGAAGGCCAGGAGAAGCTGCACCAGATGTGGCTC 900
 281  K  Q  G  V  D  Q  K  L  V  E  G  Q  E  K  L  H  Q  M  W  L  300

               910       920       930       940       950       960
                 .         .         .         .         .         .
 901 AGCTGGAACCAGAAGCAACTCCAGGGCCCCGAGAAGGAGCCGCCCAAGCCAGAGCAGGTC 960
 301  S  W  N  Q  K  Q  L  Q  G  P  E  K  E  P  P  K  P  E  Q  V  320

               970       980       990      1000      1010      1020
                 .         .         .         .         .         .
 961 GAGTCCCGGGCGCTCACCATGTTCCGGGACATTGCCCAGCAACTGCAGGCCACCTGTACC 1020
 321  E  S  R  A  L  T  M  F  R  D  I  A  Q  Q  L  Q  A  T  C  T  340

              1030      1040      1050      1060      1070      1080
                 .         .         .         .         .         .
1021 TCCCTGGGGTCCAGCATTCAGGGCCTCCCCACCAATGTGAAGGACCAGGTGCAGCAGGCC 1080
 341  S  L  G  S  S  I  Q  G  L  P  T  N  V  K  D  Q  V  Q  Q  A  360
```

FIG. 11D

```
              1090      1100      1110      1120      1130      1140
                 .         .         .         .         .         .
1081 CGCCGCCAGGTGGATGACCTCCATGCCACGTTTTCCAACATCCACTCCTTCCAGGACCTG 1140
 361  R  R  Q  V  D  D  L  H  A  T  F  S  N  I  H  S  F  Q  D  L  380

              1150      1160      1170      1180      1190      1200
                 .         .         .         .         .         .
1141 TCCAGCAACAATTCTGGCCCAGAGCCGTTAGTGTTCGCCAGCGCCCGCGAGGCCCTGGAC 1200
 381  S  S  N  N  S  G  P  E  P  L  V  F  A  S  A  R  E  A  L  D  400

              1210      1220      1230      1240      1250      1260
                 .         .         .         .         .         .
1201 CACATGGTGGGAATGATGTGGCCCACAACTCCCCTGTTTCCATGGTCTCTGTTGGGGACC 1260
 401  H  M  V  G  M  M  W  P  T  T  P  L  F  P  W  S  L  L  G  T  420

              1270      1280      1290      1300      1310      1320
                 .         .         .         .         .         .
1261 CTTTTGCCCCTTGTGATTCACTCGAGAAAGCCCCCAGAGGCAAAACAATTTTGGGGACAG 1320
 421  L  L  P  L  V  I  H  S  R  K  P  P  E  A  K  Q  F  W  G  Q  440

              1330      1340      1350
                 .         .         .
1321 GAGAGGACTCAGCGGGCTCCCGTCTCTATAATGCAGTGA 1359
 441  E  R  T  Q  R  A  P  V  S  I  M  Q  *  452
```

FIG. 11E

HAICH28 (SEQ ID NOS:23 and 24)

```
                10        20        30        40        50        60
                 .         .         .         .         .         .
  1 ATGGCGACCCCAGCCTCGGCCCCAGACACACGGGCTCTGGTGGCAGACTTTGTAGGTTAT 60
  1  M  A  T  P  A  S  A  P  D  T  R  A  L  V  A  D  F  V  G  Y  20

                70        80        90       100       110       120
                 .         .         .         .         .         .
 61 AAGCTGAGGCAGAAGGGTTATGTCTGTGGAGCTGGCCCCGGGGAGGGCCCAGCAGCTGAC 120
 21  K  L  R  Q  K  G  Y  V  C  G  A  G  P  G  E  G  P  A  A  D  40

               130       140       150       160       170       180
                 .         .         .         .         .         .
121 CCGCTGCACCAAGCCATGCGGGCAGCTGGAGATGAGTTCGAGACCCGCTTCCGGCGCACC 180
 41  P  L  H  Q  A  M  R  A  A  G  D  E  F  E  T  R  F  R  R  T  60

               190       200       210       220       230       240
                 .         .         .         .         .         .
181 TTCTCTGATCTGGCGGCTCAGCTGCATGTGACCCCAGGCTCAGCCCAACAACGCTTCACC 240
 61  F  S  D  L  A  A  Q  L  H  V  T  P  G  S  A  Q  Q  R  F  T  80
```

FIG. 12A

```
                250       260       270       280       290       300
                  .         .         .         .         .         .
241 CAGGTCTCCGATGAACTTTTTCAAGGGGGCCCCAACTGGGGCCGCCTTGTAGCCTTCTTT 300
 81  Q  V  S  D  E  L  F  Q  G  G  P  N  W  G  R  L  V  A  F  F  100

                310       320       330       340       350       360
                  .         .         .         .         .         .
301 GTCTTTGGGGCTGCACTGTGTGCTGAGAGTGTCAACAAGGAGATGGAACCACTGGTGGGA 360
101  V  F  G  A  A  L  C  A  E  S  V  N  K  E  M  E  P  L  V  G  120

                370       380       390       400       410       420
                  .         .         .         .         .         .
361 CAAGTGCAGGAGTGGATGGTGGCCTACCTGGAGACGCGGCTGGCTGACTGGATCCACAGC 420
121  Q  V  Q  E  W  M  V  A  Y  L  E  T  R  L  A  D  W  I  H  S  140

                430       440       450       460       470       480
                  .         .         .         .         .         .
421 AGTGGGGGCTGGTTATCCCAGATCACTGAAGCTGAGATGGCTGATGAAGTAATTTGCAGT 480
141  S  G  G  W  L  S  Q  I  T  E  A  E  M  A  D  E  V  I  C  S  160

                490       500       510       520       530       540
                  .         .         .         .         .         .
481 GAAATTTTAAGCGACTGTGACTCTGCTGCAAGTTCCCCAGATCTTGAGGAGCTGGAAGCT 540
161  E  I  L  S  D  C  D  S  A  A  S  S  P  D  L  E  E  L  E  A  180
```

FIG. 12B

```
               550       560       570       580       590       600
                 .         .         .         .         .         .
541 ATCAAAGCTCGAGTCAGGGAGATGGAGGAAGAAGCTGAGAAGCTAAAGGAGCTACAGAAC 600
181  I  K  A  R  V  R  E  M  E  E  E  A  E  K  L  K  E  L  Q  N  200

               610       620       630       640       650       660
                 .         .         .         .         .         .
601 GAGGTAGAGAAGCAGATGAATATGAGTCCACCTCCAGGCAATGCTGGCCCGGTGATCATG 660
201  E  V  E  K  Q  M  N  M  S  P  P  P  G  N  A  G  P  V  I  M  220

           670       680       690       700       710       720
                 .         .         .         .         .         .
661 TCCATTGAGGAGAAGATGGAGGCTGATGCCCGTTCCATCTATGTTGGCAATGTGGACTAT 720
221  S  I  E  E  K  M  E  A  D  A  R  S  I  Y  V  G  N  V  D  Y  240

               730       740       750       760       770       780
                 .         .         .         .         .         .
721 GGTGCAACAGCAGAAGAGCTGGAAGCTCACTTTCATGGCTGTGGTTCAGTCAACCGTGTT 780
241  G  A  T  A  E  E  L  E  A  H  F  H  G  C  G  S  V  N  R  V  260

               790       800       810       820       830       840
                 .         .         .         .         .         .
781 ACCATACTGTGTGACAAATTTAGTGGCCATCCCAAAGGGTTTGCGTATATAGAGTTCTCA 840
261  T  I  L  C  D  K  F  S  G  H  P  K  G  F  A  Y  I  E  F  S  280
```

FIG. 12C

```
              850       860       870       880       890       900
                .         .         .         .         .         .
 841 GACAAAGAGTCAGTGAGGACTTCCTTGGCCTTAGATGAGTCCCTATTTAGAGGAAGGCAA 900
 281  D  K  E  S  V  R  T  S  L  A  L  D  E  S  L  F  R  G  R  Q  300

              910       920       930       940       950       960
                .         .         .         .         .         .
 901 ATCAAGGTGATCCCAAAACGAACCAACAGACCAGGCATCAGCACAACAGACCGGGGTTTT 960
 301  I  K  V  I  P  K  R  T  N  R  P  G  I  S  T  T  D  R  G  F  320

              970       980       990      1000      1010      1020
                .         .         .         .         .         .
 961 CCACGAGCCCCGTACCGCGCCCGGACCACCAACTACAACAGCTCCCGCTCTCGATTCTAC 1020
 321  P  R  A  P  Y  R  A  R  T  T  N  Y  N  S  S  R  S  R  F  Y  340

             1030      1040      1050      1060      1070      1080
                .         .         .         .         .         .
1021 AGTGGTTTTAACAGCAGGCCCCGGGGTCGCGTCTACAGGGGCCGGGCTAGAGCGACATCA 1080
 341  S  G  F  N  S  R  P  R  G  R  V  Y  R  G  R  A  R  A  T  S  360

             1090
                .
1081 TGGTATTCCCCTTACTAA 1098
 361  W  Y  S  P  Y  *  365
```

FIG.12D

```
                              SEQUENCE LISTING


(1) GENERAL INFORMATION:

   (iii) NUMBER OF SEQUENCES: 24


(2) INFORMATION FOR SEQ ID NO: 1:

     (i) SEQUENCE CHARACTERISTICS:
          (A) LENGTH: 1093 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: CDS
          (B) LOCATION: 119..427

    (xi) SEQUENCE DESCRIPTION: SEQ ID NO: 1:

AGCCCGGCTG GGCTGAGCGC AGGGAGCTGC TTGGCAGTGC CAGAGCCCAG GCCCCAGAGC      60

CCTGCTGGAG AGGAGGCAGA CTGAGGCAGC AGGCCCCGCC AGCAGGCGAA GCAGGGAG       118

ATG TCA GAC TGC TAC ACG GAG CTG GAG AAG GCA GTC ATT GTC CTG GTG       166
Met Ser Asp Cys Tyr Thr Glu Leu Glu Lys Ala Val Ile Val Leu Val
  1               5                  10                  15

GAA AAC TTC TAC AAA TAT GTG TCT AAG TAC AGC CTG GTC AAG AAC AAG       214
Glu Asn Phe Tyr Lys Tyr Val Ser Lys Tyr Ser Leu Val Lys Asn Lys
             20                  25                  30

ATC AGC AAG AGC AGC TTC CGC GAG ATG CTC CAG AAA GAG CTG AAC CAC       262
Ile Ser Lys Ser Ser Phe Arg Glu Met Leu Gln Lys Glu Leu Asn His
         35                  40                  45

ATG CTG TCG GAC ACA GGG AAC CGG AAG GCT GCG GAT AAG CTC ATC CAG       310
Met Leu Ser Asp Thr Gly Asn Arg Lys Ala Ala Asp Lys Leu Ile Gln
     50                  55                  60

AAC CTG GAT GCC AAT CAT GAT GGG CGC ATC AGC TTC GAT GAG TAC TGG       358
```

-continued

```
Asn Leu Asp Ala Asn His Asp Gly Arg Ile Ser Phe Asp Glu Tyr Trp
 65                  70                  75                  80

ACC TTG ATA GGC GGC ATC ACC GGC CCC ATC GCC AAA CTC ATC CAT GAG      406
Thr Leu Ile Gly Gly Ile Thr Gly Pro Ile Ala Lys Leu Ile His Glu
                 85                  90                  95

CAG GAG CAG CAG AGC AGC AGC TAGAGACCCC TTTGGCCACA CCTTCCAGGC         457
Gln Glu Gln Gln Ser Ser Ser
            100

ACTGGCCTGA TGCCCCGCCC TGGTGCTCTC CCCAGGCTCC CTCCTCAGCC TCCTGCCCAC    517

CCAGGGCCCT TTACTCTCTT CTCCCTCCAG ACCTTCCTCT GACCCTTGCT GAACTGGGGT    577

CCCTTTGTGA GTGTCTCAGT CTAGAGGTAC CTCCCTCCCT GGGGGGTCTC AGCTCCTGGA    637

GTCGCAGGCC CTTGGGGCCC CTCTGTGAGA TCTCAATGCT GTCTGGGGAC CCTAAGAGTT    697

TTCTCACCTG TTCAGTCTCA TCTAACCTTC CAATGTCTGA TGTTCCTGCC AAATTCCTGC    757

CTGATTCTGG GTCCGTCCTG ACCTCCAAAG GTCAGCTTGG TGCTTGAGGT CTCCCTGCTC    817

TTGGTGGCAG TGGTAGCAGC AACAGCAGCA GCAGCAGCAG CAGCAGCAGC AGAGACCTCT    877

CCACTTTCCC TTAGCCCCTC TGCTGGGTAG AGAGGCACTT TCAGGGACTT CCCTCCAGCT    937

GCCTCTTCAT CTGGGAATGA GCTAAGCAAG GCTGAGCCTC CTCCTGTTGC TTGAAATAAT    997

GATGATATAA AGGCTGGATT TGGAGTTTGT ATCCCCTGGT CCCTCTGGGA TGCTCATTAA   1057

AACCTTCCCA CTCCTTGAAA AAAAAAAAAA AAAAAA                             1093
```

(2) INFORMATION FOR SEQ ID NO: 2:

(i) SEQUENCE CHARACTERISTICS:
(A) LENGTH: 103 amino acids
(B) TYPE: amino acid
(D) TOPOLOGY: linear (ii) MOLECULE TYPE: protein (xi) SEQUENCE DESCRIPTION: SEQ ID NO: 2:

```
Met Ser Asp Cys Tyr Thr Glu Leu Glu Lys Ala Val Ile Val Leu Val
  1               5                  10                  15

Glu Asn Phe Tyr Lys Tyr Val Ser Lys Tyr Ser Leu Val Lys Asn Lys
            20                  25                  30

Ile Ser Lys Ser Ser Phe Arg Glu Met Leu Gln Lys Glu Leu Asn His
        35                  40                  45

Met Leu Ser Asp Thr Gly Asn Arg Lys Ala Ala Asp Lys Leu Ile Gln
    50                  55                  60

Asn Leu Asp Ala Asn His Asp Gly Arg Ile Ser Phe Asp Glu Tyr Trp
 65                  70                  75                  80

Thr Leu Ile Gly Gly Ile Thr Gly Pro Ile Ala Lys Leu Ile His Glu
                 85                  90                  95

Gln Glu Gln Gln Ser Ser Ser
            100
```

(2) INFORMATION FOR SEQ ID NO: 3:

(i) SEQUENCE CHARACTERISTICS:
(A) LENGTH: 887 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS

-continued

```
          (B) LOCATION: 64..579

    (xi) SEQUENCE DESCRIPTION: SEQ ID NO: 3:

GCACGAGGCA GGCTCCCTGC CCATAAAACA GGGTGTGAAA GGCATCTCAG CGGCTGCCCC      60

ACC ATG GCT ACC TGG GCC CTC CTG CTC CTT GCA GCC ATG CTC CTG GGC       108
    Met Ala Thr Trp Ala Leu Leu Leu Leu Ala Ala Met Leu Leu Gly
      1               5                  10                  15

AAC CCA GGC CTT GAG GTC AGT GTG AGC CCC AAG GGC AAG AAC ACT TCT       156
Asn Pro Gly Leu Glu Val Ser Val Ser Pro Lys Gly Lys Asn Thr Ser
                 20                  25                  30

GGA AGG GAG AGT GGA TTT GGC TGG GCC ATC TGG ATG GAA GGT CTG GTC       204
Gly Arg Glu Ser Gly Phe Gly Trp Ala Ile Trp Met Glu Gly Leu Val
             35                  40                  45

TTC TCT CGT CTG AGC CCT GAG TAC TAC GAC CTG GCA AGA GCC CAC CTG       252
Phe Ser Arg Leu Ser Pro Glu Tyr Tyr Asp Leu Ala Arg Ala His Leu
         50                  55                  60

CGT GAT GAG GAG AAA TCC TGC CCG TGC CTG GCC CAG GAG GGC CCC CAG       300
Arg Asp Glu Glu Lys Ser Cys Pro Cys Leu Ala Gln Glu Gly Pro Gln
     65                  70                  75

GGT GAC CTG TTG ACC AAA ACA CAG GAG CTG GGC CGT GAC TAC AGG ACC       348
Gly Asp Leu Leu Thr Lys Thr Gln Glu Leu Gly Arg Asp Tyr Arg Thr
 80                  85                  90                  95

TGT CTG ACG ATA GTC CAA AAA CTG AAG AAG ATG GTG GAT AAG CCC ACC       396
Cys Leu Thr Ile Val Gln Lys Leu Lys Lys Met Val Asp Lys Pro Thr
                100                 105                 110

CAG AGA AGT GTT TCC AAT GCT GCG ACC CGG GTG TGT AGG ACG GGG AGG       444
Gln Arg Ser Val Ser Asn Ala Ala Thr Arg Val Cys Arg Thr Gly Arg
            115                 120                 125

TCA CGA TGG CGC GAC GTC TGC AGA AAT TTC ATG AGG AGG TAT CAG TCT       492
Ser Arg Trp Arg Asp Val Cys Arg Asn Phe Met Arg Arg Tyr Gln Ser
        130                 135                 140

AGA GTT ACC CAG GGC CTC GTG GCC GGA GAA ACT GCC CAG CAG ATC TGT       540
Arg Val Thr Gln Gly Leu Val Ala Gly Glu Thr Ala Gln Gln Ile Cys
    145                 150                 155

GAG GAC CTC AGG TTG TGT ATA CCT TCT ACA GGT CCC CTC TGAGCCCTCT        589
Glu Asp Leu Arg Leu Cys Ile Pro Ser Thr Gly Pro Leu
160                 165                 170

CACCTTGTCC TGTGGAAGAA GCACAGGCTC CTGTCCTCAG ATCCCGGGAA CCTCAGCAAC     649

CTCTGCCGGC TCCTCGCTTC CTCGATCCAG AATCCACTCT CCAGTCTCCC TCCCCTGACT     709

CCCTCTGCTG TCCTCCCCTC TCACGAGAAT AAAGTGTCAA GCAAGATTTT AGCCGCAGCT     769

GCTTCTTCTT TGGTGGATTT GAGGGGTGGG TGTCAGTGGC ATGCTGGGGT GAGCTGTGTA     829

GTCCTTCAAT AAATGTCTGT CGTGTGTCCC ATAAAAAAAA AAAAAAAAAA AAAAAAA        887
```

```
(2) INFORMATION FOR SEQ ID NO: 4:

     (i) SEQUENCE CHARACTERISTICS:
          (A) LENGTH: 172 amino acids
          (B) TYPE: amino acid
          (D) TOPOLOGY: linear

    (ii) MOLECULE TYPE: protein

    (xi) SEQUENCE DESCRIPTION: SEQ ID NO: 4:

Met Ala Thr Trp Ala Leu Leu Leu Leu Ala Ala Met Leu Leu Gly Asn
  1               5                  10                  15

Pro Gly Leu Glu Val Ser Val Ser Pro Lys Gly Lys Asn Thr Ser Gly
             20                  25                  30

Arg Glu Ser Gly Phe Gly Trp Ala Ile Trp Met Glu Gly Leu Val Phe
```

-continued

```
        35                  40                  45

Ser Arg Leu Ser Pro Glu Tyr Tyr Asp Leu Ala Arg Ala His Leu Arg
     50                  55                  60

Asp Glu Glu Lys Ser Cys Pro Cys Leu Ala Gln Glu Gly Pro Gln Gly
 65                  70                  75                  80

Asp Leu Leu Thr Lys Thr Gln Glu Leu Gly Arg Asp Tyr Arg Thr Cys
                 85                  90                  95

Leu Thr Ile Val Gln Lys Leu Lys Lys Met Val Asp Lys Pro Thr Gln
            100                 105                 110

Arg Ser Val Ser Asn Ala Ala Thr Arg Val Cys Arg Thr Gly Arg Ser
        115                 120                 125

Arg Trp Arg Asp Val Cys Arg Asn Phe Met Arg Arg Tyr Gln Ser Arg
    130                 135                 140

Val Thr Gln Gly Leu Val Ala Gly Glu Thr Ala Gln Gln Ile Cys Glu
145                 150                 155                 160

Asp Leu Arg Leu Cys Ile Pro Ser Thr Gly Pro Leu
                165                 170
```

(2) INFORMATION FOR SEQ ID NO: 5:

(i) SEQUENCE CHARACTERISTICS:
(A) LENGTH: 549 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 19..282

(xi) SEQUENCE DESCRIPTION: SEQ ID NO: 5:

```
CTCAGCGGCT GCCCCACC ATG GCT ACC TGG GCC CTC CTG CTC CTT GCA GCC       51
                    Met Ala Thr Trp Ala Leu Leu Leu Leu Ala Ala
                      1               5                  10

ATG CTC CTG GGC AAC CCA GGT CTG GTC TTC TCT CGT CTG AGC CCT GAG       99
Met Leu Leu Gly Asn Pro Gly Leu Val Phe Ser Arg Leu Ser Pro Glu
             15                  20                  25

TAC TAC GAC CTG GCA AGA GCC CAC CTG CGT GAT GAG GAG AAA TCC TGC      147
Tyr Tyr Asp Leu Ala Arg Ala His Leu Arg Asp Glu Glu Lys Ser Cys
        30                  35                  40

CCG TGC CTG GCC CAG GAG GGC CCC CAG GGT GAC CTG TTG ACC AAA ACA      195
Pro Cys Leu Ala Gln Glu Gly Pro Gln Gly Asp Leu Leu Thr Lys Thr
     45                  50                  55

CAG GAG CTG GGC CGT GAC TAC AGG ACC TGT CTG ACG ATA GTC CAA AAA      243
Gln Glu Leu Gly Arg Asp Tyr Arg Thr Cys Leu Thr Ile Val Gln Lys
 60                  65                  70                  75

CTG AAG AAG ATG GTG GAT AAG CCC ACC CAG GTC CCC TCT GAGCCCTCTC       292
Leu Lys Lys Met Val Asp Lys Pro Thr Gln Val Pro Ser
                 80                  85

ACCTTGTCCT GTGGAAGAAG CACAGGCTCC TGTCCTCAGA TCCCGGGAAC CTCAGCAACC    352

TCTGCCGGCT CCTCGCTTCC TCGATCCAGA ATCCACTCTC CAGTCTCCCT CCCCTGACTC    412

CCTCTGCTGT CCTCCCCTCT CACGAGAATA AAGTGTCAAG CCAGAAAAAA AAAAAAAAAA    472

AAAAAAAAAA AAAAAAAAAA AAAAAAAAAA AAAAAAAAAA AAAAAAAAAA AAAAAAAAAA    532

AAAAAAAAAA AAAAAAA                                                   549
```

(2) INFORMATION FOR SEQ ID NO: 6:

-continued (i) SEQUENCE CHARACTERISTICS:
(A) LENGTH: 88 amino acids
(B) TYPE: amino acid
(D) TOPOLOGY: linear (ii) MOLECULE TYPE: protein (xi) SEQUENCE DESCRIPTION: SEQ ID NO: 6:

```
Met Ala Thr Trp Ala Leu Leu Leu Leu Ala Ala Met Leu Leu Gly Asn
  1               5                  10                  15

Pro Gly Leu Val Phe Ser Arg Leu Ser Pro Glu Tyr Tyr Asp Leu Ala
             20                  25                  30

Arg Ala His Leu Arg Asp Glu Glu Lys Ser Cys Pro Cys Leu Ala Gln
         35                  40                  45

Glu Gly Pro Gln Gly Asp Leu Leu Thr Lys Thr Gln Glu Leu Gly Arg
     50                  55                  60

Asp Tyr Arg Thr Cys Leu Thr Ile Val Gln Lys Leu Lys Lys Met Val
 65                  70                  75                  80

Asp Lys Pro Thr Pro Gly Pro Leu
                 85
```

(2) INFORMATION FOR SEQ ID NO: 7:

(i) SEQUENCE CHARACTERISTICS:
(A) LENGTH: 520 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 112..288

(xi) SEQUENCE DESCRIPTION: SEQ ID NO: 7:

```
CGACCCACGC GTCCGGTTCG CTCTCTGGTA AGGGCGTGCA GGTGTTGGCC GCGGCCTCTG     60

AGCTGGGATG AGCCGTGCTC CCGGTGGAAG CAAGGGAGCC CAGCCGGAGC C ATG GCC     117
                                                         Met Ala
                                                           1

AGT ACA GTG GTA GCA GTT GGA CTG ACC ATT GCT GCT GCA GGA TTT GCA     165
Ser Thr Val Val Ala Val Gly Leu Thr Ile Ala Ala Ala Gly Phe Ala
          5                  10                  15

GGC CGT TAC GTT TTG CAA GCC ATG AAG CAT ATG GAG CCT CAA GTA AAA     213
Gly Arg Tyr Val Leu Gln Ala Met Lys His Met Glu Pro Gln Val Lys
     20                  25                  30

CAA GTT TTT CAA AGC CTA CCA AAA TCT GCC TTC AGT GGT GGC TAT TAT     261
Gln Val Phe Gln Ser Leu Pro Lys Ser Ala Phe Ser Gly Gly Tyr Tyr
 35                  40                  45                  50

AGA GCC CTA CTG CCA ATA AAG GGA AAA TAAGAGATGC TCATCGACGA           308
Arg Ala Leu Leu Pro Ile Lys Gly Lys
                 55

ATTATGCTTT TAAATCATCC TGACAAAGGA GGATCTCCTT ATATAGCAGC CAAAATCAAT    368

GAAGCTAAAG ATTTACTAGA AGGTCAAGCT AAAAAATGAA GTAAATGTAT GATGAATTTT    428

AAGTTCGTAT TAGTTTATGT ATATGAGTAC TAAGTTTTTA TAATAAAATG CTCCAGAGCT    488

ACAATTTTAA CAAACAATTA AAAAAAAAAA AA                                  520
```

(2) INFORMATION FOR SEQ ID NO: 8:

(i) SEQUENCE CHARACTERISTICS:

-continued (A) LENGTH: 59 amino acids
(B) TYPE: amino acid
(D) TOPOLOGY: linear (ii) MOLECULE TYPE: protein (xi) SEQUENCE DESCRIPTION: SEQ ID NO: 8:

```
Met Ala Ser Thr Val Val Ala Val Gly Leu Thr Ile Ala Ala Ala Gly
  1               5                  10                  15

Phe Ala Gly Arg Tyr Val Leu Gln Ala Met Lys His Met Glu Pro Gln
             20                  25                  30

Val Lys Gln Val Phe Gln Ser Leu Pro Lys Ser Ala Phe Ser Gly Gly
         35                  40                  45

Tyr Tyr Arg Ala Leu Leu Pro Ile Lys Gly Lys
     50                  55
```

(2) INFORMATION FOR SEQ ID NO: 9:

(i) SEQUENCE CHARACTERISTICS:
(A) LENGTH: 1352 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 55..402

(xi) SEQUENCE DESCRIPTION: SEQ ID NO: 9:

```
CTGAGCTGGG ATGAGCCGTG CTCCCGGTGG AAGCAAGGGA GCCCAGCCGG AGCC ATG       57
                                                            Met
                                                              1

GCC AGT ACA GTG GTA GCA GTT GGA CTG ACC ATT GCT GCT GCA GGA TTT      105
Ala Ser Thr Val Val Ala Val Gly Leu Thr Ile Ala Ala Ala Gly Phe
              5                  10                  15

GCA GGC CGT TAC GTT TTG CAA GCC ATG AAG CAT ATG GAG CCT CAA GTA      153
Ala Gly Arg Tyr Val Leu Gln Ala Met Lys His Met Glu Pro Gln Val
         20                  25                  30

AAA CAA GTT TTT CAA AGC CTA CCA AAA TCT GCC TTC AGT GGT GGC TAT      201
Lys Gln Val Phe Gln Ser Leu Pro Lys Ser Ala Phe Ser Gly Gly Tyr
     35                  40                  45

TAT AGA GGT GGG TTT GAA CCC AAA ATG ACA AAA CGG GAA GCA GCA TTA      249
Tyr Arg Gly Gly Phe Glu Pro Lys Met Thr Lys Arg Glu Ala Ala Leu
 50                  55                  60                  65

ATA CTA GGT GTA AGC CCT ACT GCC AAT AAA GGG AAA ATA AGA GAT GCT      297
Ile Leu Gly Val Ser Pro Thr Ala Asn Lys Gly Lys Ile Arg Asp Ala
                 70                  75                  80

CAT CGA CGA ATT ATG CTT TTA AAT CAT CCT GAC AAA GGA GGA TCT CCT      345
His Arg Arg Ile Met Leu Leu Asn His Pro Asp Lys Gly Gly Ser Pro
             85                  90                  95

TAT ATA GCA GCC AAA ATC AAT GAA GCT AAA GAT TTA CTA GAA GGT CAA      393
Tyr Ile Ala Ala Lys Ile Asn Glu Ala Lys Asp Leu Leu Glu Gly Gln
        100                 105                 110

GCT AAA AAA TGAAGTAAAT GTATGATGAA TTTTAAGTTC GTATTAGTTT              442
Ala Lys Lys
    115

ATGTATATGA GTACTAAGTT TTTATAATAA AATGCCTCAG AGCTACAATT TTAAAAAATG    502

ATTTAGCACA AGCTAAATCT CAAAGCCTTG GTATAATTTT CTTGTTTAAA TTTGGGGATT    562

TTAAATCAGA TTATAGTTTA GAATATTTGC GTATTAATTA TGGGCAAGCA CACACCTTCT    622
```

-continued

```
GAATAGAAAT ATTGTTCATT ACTCATTTAG CAGATAATTT GGGACCTATG TCTACTTTTC    682

AAGGCAAAGT GAAGATGACA GTCCTTGCTC TCAGGGAGCC CCCACTTTAA TGGGAGACTG    742

ATAAACTGGT AATTAGACTG TGATAAATAG TATGATGGAA ATTAGCTTAA GCTGTTTAAG    802

TAGGGACTCT TCTTATTCGG TGGAAAGGCT GTTCCAGGTA CAGGCAACTG GCCTGGCAAC    862

TTGGATACTT GGAACCTTGT ATTTAAAAGT GAATTTAACC ACAACTGAGA CCTAAGAAAT    922

TGACCTAGGG GTGTGTGTGT GTGTGTATTC TATGTACATA TAAACCCATT TTTATTTCAT    982

GCATTAAAAA TAGTATGATA AAGATTTCAG AGTACAGGTC TGGTACAATC ACAGTTCATT   1042

GCAGCCTCAA CCTCCTGGGT TTAAGCAGTC CTCCCGCCTC AGCCTCCCAA AGTACTGGGA   1102

TTACAGGCAT GAGTATTTAC ATTGTATTCA GCTAGCCCCT TAAAGGTAAT GACCATTTAT   1162

AAATTATTCC TTCAGTTGGC TATTTCTTGA CATAATCAAA CTTCTGCAAT TGTTATGATT   1222

AAGCTTAAAC CCTGTTAGCA AAACTGAAAA CTGAAATGTT CTCAATATCA ACATATTTAA   1282

TTTGGACTCT TTAGAATTTA TACACTAATA AATTTAAATG ATGTTTAAAG GCAAAAAAAA   1342

AAAAAAAAAA                                                          1352
```

(2) INFORMATION FOR SEQ ID NO: 10:

(i) SEQUENCE CHARACTERISTICS:
(A) LENGTH: 116 amino acids
(B) TYPE: amino acid
(D) TOPOLOGY: linear (ii) MOLECULE TYPE: protein (xi) SEQUENCE DESCRIPTION: SEQ ID NO: 10:

```
Met Ala Ser Thr Val Val Ala Val Gly Leu Thr Ile Ala Ala Ala Gly
  1               5                  10                  15

Phe Ala Gly Arg Tyr Val Leu Gln Ala Met Lys His Met Glu Pro Gln
             20                  25                  30

Val Lys Gln Val Phe Gln Ser Leu Pro Lys Ser Ala Phe Ser Gly Gly
         35                  40                  45

Tyr Tyr Arg Gly Gly Phe Glu Pro Lys Met Thr Lys Arg Glu Ala Ala
     50                  55                  60

Leu Ile Leu Gly Val Ser Pro Thr Ala Asn Lys Gly Lys Ile Arg Asp
 65                  70                  75                  80

Ala His Arg Arg Ile Met Leu Leu Asn His Pro Asp Lys Gly Gly Ser
                 85                  90                  95

Pro Tyr Ile Ala Ala Lys Ile Asn Glu Ala Lys Asp Leu Leu Glu Gly
            100                 105                 110

Gln Ala Lys Lys
        115
```

(2) INFORMATION FOR SEQ ID NO: 11:

(i) SEQUENCE CHARACTERISTICS:
(A) LENGTH: 632 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 88..537

(xi) SEQUENCE DESCRIPTION: SEQ ID NO: 11:

-continued

```
CACGAGGCCC GGACCAGGCG CCTGTGCCTC CTCCTCGTCC CTCGCCGCGT CCGCGAACCT     60

GGAGCCGGCG GGAGCCCCGC GCTCGCC ATG TCG GGC GAG CTC AGC AAC AGG        111
                              Met Ser Gly Glu Leu Ser Asn Arg
                                1               5

TTC CAA GGA GGG AAG GCG TTC GGC TTG CTC AAA GCC CGG CAG GAG AGG      159
Phe Gln Gly Gly Lys Ala Phe Gly Leu Leu Lys Ala Arg Gln Glu Arg
     10                  15                  20

AGG CTG GCC GAG ATC AAC CGG GAG TTT CTG TGT GAC CAG AAG TAC AGT      207
Arg Leu Ala Glu Ile Asn Arg Glu Phe Leu Cys Asp Gln Lys Tyr Ser
 25                  30                  35                  40

GAT GAA GAG AAC CTT CCA GAA AAG CTC ACA GCC TTC AAA GAG AAG TAC      255
Asp Glu Glu Asn Leu Pro Glu Lys Leu Thr Ala Phe Lys Glu Lys Tyr
                 45                  50                  55

ATG GAG TTT GAC CTG AAC AAT GAA GGC GAG ATT GAC CTG ATG TCT TTA      303
Met Glu Phe Asp Leu Asn Asn Glu Gly Glu Ile Asp Leu Met Ser Leu
             60                  65                  70

AAG AGG ATG ATG GAG AAG CTT GGT GTC CCC AAG ACC CAC CTG GAG ATG      351
Lys Arg Met Met Glu Lys Leu Gly Val Pro Lys Thr His Leu Glu Met
         75                  80                  85

AAG AAG ATG ATC TCA GAG GTG ACA GGA GGG GTC AGT GAC ACT ATA TCC      399
Lys Lys Met Ile Ser Glu Val Thr Gly Gly Val Ser Asp Thr Ile Ser
     90                  95                 100

TAC CGA GAC TTT GTG AAC ATG ATG CTG GGG AAA CGG TCG GCT GTC CTC      447
Tyr Arg Asp Phe Val Asn Met Met Leu Gly Lys Arg Ser Ala Val Leu
105                 110                 115                 120

AAG TTA GTC ATG ATG TTT GAA GGA AAA GCC AAC GAG AGC AGC CCC AAG      495
Lys Leu Val Met Met Phe Glu Gly Lys Ala Asn Glu Ser Ser Pro Lys
                125                 130                 135

CCA GTT GGC CCC CCT CCA GAG AGA GAC ATT GCT AGC CTG CCC              537
Pro Val Gly Pro Pro Pro Glu Arg Asp Ile Ala Ser Leu Pro
            140                 145                 150

TGAGGACCCC GCCTGGACTC CCCAGCCTTC CCACCCCATA CCTCCCTCCC GATCTTGCTG    597

CCCTTCTTGA CACACTGTGA TCCGGCACGA GCGGC                               632
```

(2) INFORMATION FOR SEQ ID NO: 12:

(i) SEQUENCE CHARACTERISTICS:
(A) LENGTH: 150 amino acids
(B) TYPE: amino acid
(D) TOPOLOGY: linear (ii) MOLECULE TYPE: protein (xi) SEQUENCE DESCRIPTION: SEQ ID NO: 12:

```
Met Ser Gly Glu Leu Ser Asn Arg Phe Gln Gly Gly Lys Ala Phe Gly
  1               5                  10                  15

Leu Leu Lys Ala Arg Gln Glu Arg Arg Leu Ala Glu Ile Asn Arg Glu
             20                  25                  30

Phe Leu Cys Asp Gln Lys Tyr Ser Asp Glu Glu Asn Leu Pro Glu Lys
         35                  40                  45

Leu Thr Ala Phe Lys Glu Lys Tyr Met Glu Phe Asp Leu Asn Asn Glu
     50                  55                  60

Gly Glu Ile Asp Leu Met Ser Leu Lys Arg Met Met Glu Lys Leu Gly
 65                  70                  75                  80

Val Pro Lys Thr His Leu Glu Met Lys Lys Met Ile Ser Glu Val Thr
                 85                  90                  95

Gly Gly Val Ser Asp Thr Ile Ser Tyr Arg Asp Phe Val Asn Met Met
            100                 105                 110
```

-continued

```
Leu Gly Lys Arg Ser Ala Val Leu Lys Leu Val Met Met Phe Glu Gly
        115                 120                 125

Lys Ala Asn Glu Ser Ser Pro Lys Pro Val Gly Pro Pro Pro Glu Arg
    130                 135                 140

Asp Ile Ala Ser Leu Pro
145                 150
```

(2) INFORMATION FOR SEQ ID NO: 13:

(i) SEQUENCE CHARACTERISTICS:
(A) LENGTH: 582 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..579

(xi) SEQUENCE DESCRIPTION: SEQ ID NO: 13:

```
ATG GGC AGC GCG GAC TGC GAG CTG AGC GCC AAG CTG CTG CGG CGC GCA        48
Met Gly Ser Ala Asp Cys Glu Leu Ser Ala Lys Leu Leu Arg Arg Ala
  1               5                  10                  15

GAC CTC AAC CAG GGC ATC GGC GAG CCC CAG TCG CCC AGC CGC CGC GTC        96
Asp Leu Asn Gln Gly Ile Gly Glu Pro Gln Ser Pro Ser Arg Arg Val
             20                  25                  30

TTC AAC CCC TAC ACC GAG TTC AAG GAG TTC TCC AGG AAG CAG ATC AAG       144
Phe Asn Pro Tyr Thr Glu Phe Lys Glu Phe Ser Arg Lys Gln Ile Lys
         35                  40                  45

GAC ATG GAG AAG ATG TTC AAG CAG TAT GAT GCC GGG CGG GAC GGC TTC       192
Asp Met Glu Lys Met Phe Lys Gln Tyr Asp Ala Gly Arg Asp Gly Phe
     50                  55                  60

ATC GAC CTG ATG GAG CTA AAA CTC ATG ATG GAG AAA CTT GGG GCC CCT       240
Ile Asp Leu Met Glu Leu Lys Leu Met Met Glu Lys Leu Gly Ala Pro
 65                  70                  75                  80

CAG ACC CAC CTG GGC CTG AAA AAC ATG ATC AAG GAG GTG GAT GAG GAC       288
Gln Thr His Leu Gly Leu Lys Asn Met Ile Lys Glu Val Asp Glu Asp
                 85                  90                  95

TTT GAC AGC AAG CTG AGC TTC CGG GAG TTC CTC CTG ATC TTC CGC AAG       336
Phe Asp Ser Lys Leu Ser Phe Arg Glu Phe Leu Leu Ile Phe Arg Lys
            100                 105                 110

GCG GCG GCC GGG GAG CTT CAG GAG GAC AGC GGG CTG TGC GTG CTG GCC       384
Ala Ala Ala Gly Glu Leu Gln Glu Asp Ser Gly Leu Cys Val Leu Ala
        115                 120                 125

CGC CTC TCT GAG ATC GAC GTC TCC AGT GAG GGT GTC AAG GGG GCC AAG       432
Arg Leu Ser Glu Ile Asp Val Ser Ser Glu Gly Val Lys Gly Ala Lys
    130                 135                 140

AGC TTC TTT GAG GCC AAG GTC CAG GCC ATC AAC GTG TCC AGC CGC TTC       480
Ser Phe Phe Glu Ala Lys Val Gln Ala Ile Asn Val Ser Ser Arg Phe
145                 150                 155                 160

GAG GAG GAG ATC AAG GCA GAG CAG GAG GAA AGG AAG AAG CAG GCG GAG       528
Glu Glu Glu Ile Lys Ala Glu Gln Glu Glu Arg Lys Lys Gln Ala Glu
                165                 170                 175

GAG ATG AAG CAG CGG AAA GCG GCC TTC AAG GAG CTG CAG TCC ACC TTT       576
Glu Met Lys Gln Arg Lys Ala Ala Phe Lys Glu Leu Gln Ser Thr Phe
            180                 185                 190

AAG TAG                                                                582
Lys
```

(2) INFORMATION FOR SEQ ID NO: 14:

-continued (i) SEQUENCE CHARACTERISTICS:
(A) LENGTH: 193 amino acids
(B) TYPE: amino acid
(D) TOPOLOGY: linear (ii) MOLECULE TYPE: protein (xi) SEQUENCE DESCRIPTION: SEQ ID NO: 14:

```
Met Gly Ser Ala Asp Cys Glu Leu Ser Ala Lys Leu Leu Arg Arg Ala
  1               5                  10                  15

Asp Leu Asn Gln Gly Ile Gly Glu Pro Gln Ser Pro Ser Arg Arg Val
             20                  25                  30

Phe Asn Pro Tyr Thr Glu Phe Lys Glu Phe Ser Arg Lys Gln Ile Lys
        35                  40                  45

Asp Met Glu Lys Met Phe Lys Gln Tyr Asp Ala Gly Arg Asp Gly Phe
     50                  55                  60

Ile Asp Leu Met Glu Leu Lys Leu Met Met Glu Lys Leu Gly Ala Pro
 65                  70                  75                  80

Gln Thr His Leu Gly Leu Lys Asn Met Ile Lys Glu Val Asp Glu Asp
                 85                  90                  95

Phe Asp Ser Lys Leu Ser Phe Arg Glu Phe Leu Leu Ile Phe Arg Lys
            100                 105                 110

Ala Ala Ala Gly Glu Leu Gln Glu Asp Ser Gly Leu Cys Val Leu Ala
        115                 120                 125

Arg Leu Ser Glu Ile Asp Val Ser Ser Glu Gly Val Lys Gly Ala Lys
    130                 135                 140

Ser Phe Phe Glu Ala Lys Val Gln Ala Ile Asn Val Ser Ser Arg Phe
145                 150                 155                 160

Glu Glu Glu Ile Lys Ala Glu Gln Glu Glu Arg Lys Lys Gln Ala Glu
                165                 170                 175

Glu Met Lys Gln Arg Lys Ala Ala Phe Lys Glu Leu Gln Ser Thr Phe
            180                 185                 190

Lys
```

(2) INFORMATION FOR SEQ ID NO: 15:

(i) SEQUENCE CHARACTERISTICS:
(A) LENGTH: 1356 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 115..1086

(xi) SEQUENCE DESCRIPTION: SEQ ID NO: 15:

```
ACATATTTAC ATTTGATTTA ACAGTGAACC TTAATTCTTT CTGGCTTCAC AGTGAAACAA      60

GTTTATGCAA TCGATCAAAT ATTTTCATCC CTGAGGTTAA CAATTACCAT CAAA ATG       117
                                                            Met
                                                              1

TTT TGT GGA GAC TAT GTG CAA GGA ACC ATC TTC CCA GCT CCC AAT TTC       165
Phe Cys Gly Asp Tyr Val Gln Gly Thr Ile Phe Pro Ala Pro Asn Phe
              5                  10                  15

AAT CCC ATA ATG GAT GCC CAA ATG CTA GGA GGA GCA CTC CAA GGA TTT       213
Asn Pro Ile Met Asp Ala Gln Met Leu Gly Gly Ala Leu Gln Gly Phe
         20                  25                  30
```

-continued

```
GAC TGT GAC AAA GAC ATG CTG ATC AAC ATT CTG ACT CAG CGC TGC AAT       261
Asp Cys Asp Lys Asp Met Leu Ile Asn Ile Leu Thr Gln Arg Cys Asn
     35                 40                  45

GCA CAA AGG ATG ATG ATT GCA GAG GCA TAC CAG AGC ATG TAT GGC CGG       309
Ala Gln Arg Met Met Ile Ala Glu Ala Tyr Gln Ser Met Tyr Gly Arg
 50                  55                  60                  65

GAC CTG ATT GGG GAT CTG AGG GAG CAG CTT TCG GAT CAC TTC AAA GAT       357
Asp Leu Ile Gly Asp Leu Arg Glu Gln Leu Ser Asp His Phe Lys Asp
                 70                  75                  80

GTG ATG GCT GGC CTC ATG TAC CCA CCA CCA CTG TAT GAT GCT CAT GAG       405
Val Met Ala Gly Leu Met Tyr Pro Pro Pro Leu Tyr Asp Ala His Glu
             85                  90                  95

CTC TGG CAT GCC ATG AAG GGA GTA GGC ACT GAT GAG AAT TGC CTC ATT       453
Leu Trp His Ala Met Lys Gly Val Gly Thr Asp Glu Asn Cys Leu Ile
        100                 105                 110

GAA ATA CTA GCT TCA AGA ACA AAT GGA GAA ATT TTC CAG ATG CGA GAA       501
Glu Ile Leu Ala Ser Arg Thr Asn Gly Glu Ile Phe Gln Met Arg Glu
    115                 120                 125

GCC TAC TGC TTG CAA TAC AGC AAT AAC CTC CAA GAG GAC ATT TAT TCA       549
Ala Tyr Cys Leu Gln Tyr Ser Asn Asn Leu Gln Glu Asp Ile Tyr Ser
130                 135                 140                 145

GAG ACC TCG GGA CAC TTC AGA GAT ACT CTC ATG AAC TTG GTC CAG GGG       597
Glu Thr Ser Gly His Phe Arg Asp Thr Leu Met Asn Leu Val Gln Gly
                150                 155                 160

ACC AGA GAG GAA GGA TAT ACA GAC CCT GCG ATG GCT GCT CAG GAT GCA       645
Thr Arg Glu Glu Gly Tyr Thr Asp Pro Ala Met Ala Ala Gln Asp Ala
            165                 170                 175

ATG GTC CTA TGG GAA GCC TGT CAG CAG AAG ACG GGG GAG CAC AAA ACC       693
Met Val Leu Trp Glu Ala Cys Gln Gln Lys Thr Gly Glu His Lys Thr
        180                 185                 190

ATG CTG CAA ATG ATC CTG TGC AAC AAG AGC TAC CAG CAG CTG CGG CTG       741
Met Leu Gln Met Ile Leu Cys Asn Lys Ser Tyr Gln Gln Leu Arg Leu
    195                 200                 205

GTT TTC CAG GAA TTT CAA AAT ATT TCT GGG CAA GAT ATG GTA GAT GCC       789
Val Phe Gln Glu Phe Gln Asn Ile Ser Gly Gln Asp Met Val Asp Ala
210                 215                 220                 225

ATT AAT GAA TGT TAT GAT GGA TAC TTT CAG GAG CTG CTG GTT GCA ATT       837
Ile Asn Glu Cys Tyr Asp Gly Tyr Phe Gln Glu Leu Leu Val Ala Ile
                230                 235                 240

GTT CTC TGT GTT CGA GAC AAA CCA GCC TAT TTT GCT TAT AGA TTA TAT       885
Val Leu Cys Val Arg Asp Lys Pro Ala Tyr Phe Ala Tyr Arg Leu Tyr
            245                 250                 255

AGT GCA ATT CAT GAC TTT GGT TTC CAT AAT AAA ACT GTA ATC AGG ATT       933
Ser Ala Ile His Asp Phe Gly Phe His Asn Lys Thr Val Ile Arg Ile
        260                 265                 270

CTC ATT GCC AGA AGT GAA ATA GAC CTG CTG ACC ATA AGG AAA CGA TAC       981
Leu Ile Ala Arg Ser Glu Ile Asp Leu Leu Thr Ile Arg Lys Arg Tyr
    275                 280                 285

AAA GAG CGA TAT GGA AAA TCC CTA TTT CAT GAT ATC AGA AAT TTT GCT      1029
Lys Glu Arg Tyr Gly Lys Ser Leu Phe His Asp Ile Arg Asn Phe Ala
290                 295                 300                 305

TCA GGG CAT TAT AAG AAA GCA CTG CTT GCC ATC TGT GCT GGT GAT GCT      1077
Ser Gly His Tyr Lys Lys Ala Leu Leu Ala Ile Cys Ala Gly Asp Ala
                310                 315                 320

GAG GAC TAC TAAAATGAAG AGGACTTGGA GTACTGTGCA CTCCTCTTTC              1126
Glu Asp Tyr

TAGACACTTC CAAATAGAGA TTTTCTCACA AATTTGTACT GTTCATGGCA CTATTAACAA    1186

AACTATACAA TCATATTTTC TCTTCTATCT TTGAAATTAT TCTAAGCCAA AGAAAACTAT    1246
```

-continued

```
GAATGAAAGT ATATGATACT GAATTTGCCT ACTATCCTGA ATTTGCCTAC TATCTAATCA   1306

GCAATTAAAT AAATTGTGCA TGATGGAATA ATAAAAAAAA AAAAAAAAAA              1356


(2) INFORMATION FOR SEQ ID NO: 16:

     (i) SEQUENCE CHARACTERISTICS:
          (A) LENGTH: 324 amino acids
          (B) TYPE: amino acid
          (D) TOPOLOGY: linear

    (ii) MOLECULE TYPE: protein

    (xi) SEQUENCE DESCRIPTION: SEQ ID NO: 16:

Met Phe Cys Gly Asp Tyr Val Gln Gly Thr Ile Phe Pro Ala Pro Asn
  1               5                  10                  15

Phe Asn Pro Ile Met Asp Ala Gln Met Leu Gly Gly Ala Leu Gln Gly
            20                  25                  30

Phe Asp Cys Asp Lys Asp Met Leu Ile Asn Ile Leu Thr Gln Arg Cys
        35                  40                  45

Asn Ala Gln Arg Met Met Ile Ala Glu Ala Tyr Gln Ser Met Tyr Gly
    50                  55                  60

Arg Asp Leu Ile Gly Asp Leu Arg Glu Gln Leu Ser Asp His Phe Lys
 65                  70                  75                  80

Asp Val Met Ala Gly Leu Met Tyr Pro Pro Pro Leu Tyr Asp Ala His
                 85                  90                  95

Glu Leu Trp His Ala Met Lys Gly Val Gly Thr Asp Glu Asn Cys Leu
            100                 105                 110

Ile Glu Ile Leu Ala Ser Arg Thr Asn Gly Glu Ile Phe Gln Met Arg
        115                 120                 125

Glu Ala Tyr Cys Leu Gln Tyr Ser Asn Asn Leu Gln Glu Asp Ile Tyr
    130                 135                 140

Ser Glu Thr Ser Gly His Phe Arg Asp Thr Leu Met Asn Leu Val Gln
145                 150                 155                 160

Gly Thr Arg Glu Glu Gly Tyr Thr Asp Pro Ala Met Ala Ala Gln Asp
                165                 170                 175

Ala Met Val Leu Trp Glu Ala Cys Gln Gln Lys Thr Gly Glu His Lys
            180                 185                 190

Thr Met Leu Gln Met Ile Leu Cys Asn Lys Ser Tyr Gln Gln Leu Arg
        195                 200                 205

Leu Val Phe Gln Glu Phe Gln Asn Ile Ser Gly Gln Asp Met Val Asp
    210                 215                 220

Ala Ile Asn Glu Cys Tyr Asp Gly Tyr Phe Gln Glu Leu Leu Val Ala
225                 230                 235                 240

Ile Val Leu Cys Val Arg Asp Lys Pro Ala Tyr Phe Ala Tyr Arg Leu
                245                 250                 255

Tyr Ser Ala Ile His Asp Phe Gly Phe His Asn Lys Thr Val Ile Arg
            260                 265                 270

Ile Leu Ile Ala Arg Ser Glu Ile Asp Leu Leu Thr Ile Arg Lys Arg
        275                 280                 285

Tyr Lys Glu Arg Tyr Gly Lys Ser Leu Phe His Asp Ile Arg Asn Phe
    290                 295                 300

Ala Ser Gly His Tyr Lys Lys Ala Leu Leu Ala Ile Cys Ala Gly Asp
305                 310                 315                 320

Ala Glu Asp Tyr
```

-continued (2) INFORMATION FOR SEQ ID NO: 17:

(i) SEQUENCE CHARACTERISTICS:
(A) LENGTH: 2934 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..2931

(xi) SEQUENCE DESCRIPTION: SEQ ID NO: 17:

```
ATG GAT ATT TAC GAC ACT CAA ACC TTG GGG GTT GTG GTC TTT GGA GGA        48
Met Asp Ile Tyr Asp Thr Gln Thr Leu Gly Val Val Val Phe Gly Gly
  1               5                  10                  15

TTC ATG GTT GTT TCT GCC ATT GGC ATC TTC CTG GTG TCG ACT TTC TCC        96
Phe Met Val Val Ser Ala Ile Gly Ile Phe Leu Val Ser Thr Phe Ser
             20                  25                  30

ATG AAG GAA ACG TCA TAT GAA GAA GCC CTA GCC AAC CAG CGC AAG GAG       144
Met Lys Glu Thr Ser Tyr Glu Glu Ala Leu Ala Asn Gln Arg Lys Glu
         35                  40                  45

ATG GCG AAA ACT CAC CAC CAG AAA GTC GAG AAG AAA AAG AAG GAG AAA       192
Met Ala Lys Thr His His Gln Lys Val Glu Lys Lys Lys Lys Glu Lys
     50                  55                  60

ACA GTG GAG AAG AAA GGA AAG ACC AAG AAA AAG GAA GAG AAA CCT AAT       240
Thr Val Glu Lys Lys Gly Lys Thr Lys Lys Lys Glu Glu Lys Pro Asn
 65                  70                  75                  80

GGG AAG ATA CCT GAT CAT GAT CCA GCC CCC AAT GTG ACT GTC CTC CTT       288
Gly Lys Ile Pro Asp His Asp Pro Ala Pro Asn Val Thr Val Leu Leu
                 85                  90                  95

CGA GAA CCA GTG CGG GCT CCT GCT GTG GCT GTG GCT CCA ACC CCA GTG       336
Arg Glu Pro Val Arg Ala Pro Ala Val Ala Val Ala Pro Thr Pro Val
            100                 105                 110

CAG CCC CCC ATT ATC GTT GCT CCT GTC GCC ACA GTT CCA GCC ATG CCC       384
Gln Pro Pro Ile Ile Val Ala Pro Val Ala Thr Val Pro Ala Met Pro
        115                 120                 125

CAG GAG AAG CTG GCC TCC TCC CCC AAG GAC AAA AAG AAG AAG GAG AAA       432
Gln Glu Lys Leu Ala Ser Ser Pro Lys Asp Lys Lys Lys Lys Glu Lys
    130                 135                 140

AAA GTG GCA AAA GTG GAA CCA GCT GTC AGC TCT GTA GTG AAT TCC ATC       480
Lys Val Ala Lys Val Glu Pro Ala Val Ser Ser Val Val Asn Ser Ile
145                 150                 155                 160

CAG GTT CTC ACT TCG AAG GCT GCC ATC TTG GAA ACT GCT CCC AAG GAG       528
Gln Val Leu Thr Ser Lys Ala Ala Ile Leu Glu Thr Ala Pro Lys Glu
                165                 170                 175

GGC AGA AAT ACA GAT GTG GCC CAG AGC CCA GAG GCA CCA AAG CAA GAG       576
Gly Arg Asn Thr Asp Val Ala Gln Ser Pro Glu Ala Pro Lys Gln Glu
            180                 185                 190

GCT CCT GCC AAG AAG AAG TCT GGT TCA AAG AAA AAA GGG CCC CCA GAT       624
Ala Pro Ala Lys Lys Lys Ser Gly Ser Lys Lys Lys Gly Pro Pro Asp
        195                 200                 205

GCC GAC GGC CCT CTC TAC CTC CCC TAC AAG ACG CTG GTC TCC ACG GTT       672
Ala Asp Gly Pro Leu Tyr Leu Pro Tyr Lys Thr Leu Val Ser Thr Val
    210                 215                 220

GGG AGC ATG GTG TTC AAC GAG GGC GAG GCC CAG CGG CTC ATC GAG ATC       720
Gly Ser Met Val Phe Asn Glu Gly Glu Ala Gln Arg Leu Ile Glu Ile
225                 230                 235                 240

CTG TCT GAG AAG GCT GGC ATC ATT CAG GAC ACC TGG CAC AAG GCC ACT       768
Leu Ser Glu Lys Ala Gly Ile Ile Gln Asp Thr Trp His Lys Ala Thr
                245                 250                 255
```

-continued

```
CAG AAG GGT GAC CCT GTG GCG ATT CTG AAA CGC CAG CTG GAA GAG AAG      816
Gln Lys Gly Asp Pro Val Ala Ile Leu Lys Arg Gln Leu Glu Glu Lys
            260                 265                 270

GAA AAA CTG CTG GCC ACA GAA CAG GAA GAT GCG GCT GTC GCC AAG AGC      864
Glu Lys Leu Leu Ala Thr Glu Gln Glu Asp Ala Ala Val Ala Lys Ser
        275                 280                 285

AAA CTG AGG GAG CTC AAC AAG GAG ATG GCA GCA GAA AAG GCC AAA GCA      912
Lys Leu Arg Glu Leu Asn Lys Glu Met Ala Ala Glu Lys Ala Lys Ala
    290                 295                 300

GCA GCC GGG GAG GCC AAA GTG AAA AAG CAG CTG GTG GCC CGG GAG CAG      960
Ala Ala Gly Glu Ala Lys Val Lys Lys Gln Leu Val Ala Arg Glu Gln
305                 310                 315                 320

GAG ATC ACG GCT GTG CAG GCA CGC ATG CAG GCC AGC TAC CGG GAG CAC     1008
Glu Ile Thr Ala Val Gln Ala Arg Met Gln Ala Ser Tyr Arg Glu His
                325                 330                 335

GTG AAG GAG GTG CAG CAG CTG CAG GGC AAG ATC CGG ACT CTT CAG GAG     1056
Val Lys Glu Val Gln Gln Leu Gln Gly Lys Ile Arg Thr Leu Gln Glu
            340                 345                 350

CAG CTG GAG AAT GGC CCC AAC ACG CAG CTG GCC CGC CTG CAG CAG GAG     1104
Gln Leu Glu Asn Gly Pro Asn Thr Gln Leu Ala Arg Leu Gln Gln Glu
        355                 360                 365

AAC TCC ATC CTG CGG GAT GCC TTG AAC CAG GCC ACG AGC CAG GTG GAG     1152
Asn Ser Ile Leu Arg Asp Ala Leu Asn Gln Ala Thr Ser Gln Val Glu
    370                 375                 380

AGC AAG CAG AAC GCA GAG CTG GCC AAG CTT CGG CAG GAG CTC AGC AAG     1200
Ser Lys Gln Asn Ala Glu Leu Ala Lys Leu Arg Gln Glu Leu Ser Lys
385                 390                 395                 400

GTC AGC AAA GAG CTG GTG GAG AAG TCA GAG GCT GTG CGG CAA GAT GAG     1248
Val Ser Lys Glu Leu Val Glu Lys Ser Glu Ala Val Arg Gln Asp Glu
                405                 410                 415

CAG CAG CGG AAA GCT CTG GAA GCC AAG GCA GCT GCC TTC GAG AAG CAG     1296
Gln Gln Arg Lys Ala Leu Glu Ala Lys Ala Ala Ala Phe Glu Lys Gln
            420                 425                 430

GTC CTG CAG CTG CAG GCG TCC CAC AGG GAG AGT GAG GAG GCC CTG CAG     1344
Val Leu Gln Leu Gln Ala Ser His Arg Glu Ser Glu Glu Ala Leu Gln
        435                 440                 445

AAG CGC CTG GAC GAG GTC AGC CGG GAG CTG TGC CAC ACG CAG AGC AGC     1392
Lys Arg Leu Asp Glu Val Ser Arg Glu Leu Cys His Thr Gln Ser Ser
    450                 455                 460

CAC GCC AGC CTC CGG GCG GAT GCC GAG AAG GCC CAG GAG CAA CAG CAG     1440
His Ala Ser Leu Arg Ala Asp Ala Glu Lys Ala Gln Glu Gln Gln Gln
465                 470                 475                 480

CAG ATG GCC GAG CTG CAC AGC AAG TTA CAG TCC TCC GAG GCG GAG GTG     1488
Gln Met Ala Glu Leu His Ser Lys Leu Gln Ser Ser Glu Ala Glu Val
                485                 490                 495

CGC AGC AAA TGC GAG GAG CTG AGT GGC CTC CAC GGG CAG CTC CAG GAG     1536
Arg Ser Lys Cys Glu Glu Leu Ser Gly Leu His Gly Gln Leu Gln Glu
            500                 505                 510

GCC AGG GCA GAG AAC TCC CAG CTC ACA GAG AGA ATC CGT TCC ATT GAG     1584
Ala Arg Ala Glu Asn Ser Gln Leu Thr Glu Arg Ile Arg Ser Ile Glu
        515                 520                 525

GCC CTG CTG GAG GCG GGC CAG GCG CGG GAT GCC CAG GAC GTC CAG GCC     1632
Ala Leu Leu Glu Ala Gly Gln Ala Arg Asp Ala Gln Asp Val Gln Ala
    530                 535                 540

AGC CAG GCG GAG GCT GAC CAG CAG CAG ACT CGC CTC AAG GAG CTG GAG     1680
Ser Gln Ala Glu Ala Asp Gln Gln Gln Thr Arg Leu Lys Glu Leu Glu
545                 550                 555                 560

TCC CAG GTG TCG GGT CTG GAG AAG GAG GCC ATC GAG CTC AGG GAG GCC     1728
Ser Gln Val Ser Gly Leu Glu Lys Glu Ala Ile Glu Leu Arg Glu Ala
```

-continued

```
                565                 570                 575

GTC GAG CAG CAG AAA GTG AAG AAC AAT GAC CTC CGG GAG AAG AAC TGG     1776
Val Glu Gln Gln Lys Val Lys Asn Asn Asp Leu Arg Glu Lys Asn Trp
            580                 585                 590

AAG GCC ATG GAG GCA CTG GCC ACG GCC GAG CAG GCC TGC AAG GAG AAG     1824
Lys Ala Met Glu Ala Leu Ala Thr Ala Glu Gln Ala Cys Lys Glu Lys
        595                 600                 605

CTG CAC TCC CTG ACC CAG GCC AAG GAG GAA TCG GAG AAG CAG CTC TGT     1872
Leu His Ser Leu Thr Gln Ala Lys Glu Glu Ser Glu Lys Gln Leu Cys
    610                 615                 620

CTG ATT GAG GCG CAG ACC ATG GAG GCC CTG CTG GCT CTG CTC CCA GAA     1920
Leu Ile Glu Ala Gln Thr Met Glu Ala Leu Leu Ala Leu Leu Pro Glu
625                 630                 635                 640

CTC TCT GTC TTG GCA CAA CAG AAT TAC ACC GAG TGG CTG CAG GAT CTC     1968
Leu Ser Val Leu Ala Gln Gln Asn Tyr Thr Glu Trp Leu Gln Asp Leu
                645                 650                 655

AAA GAG AAA GGC CCC ACG CTG CTG AAG CAC CCG CCA GCT CCC GCG GAG     2016
Lys Glu Lys Gly Pro Thr Leu Leu Lys His Pro Pro Ala Pro Ala Glu
            660                 665                 670

CCC TCC TCG GAC CTG GCC TCC AAG TTG AGG GAG GCC GAG GAG ACG CAG     2064
Pro Ser Ser Asp Leu Ala Ser Lys Leu Arg Glu Ala Glu Glu Thr Gln
        675                 680                 685

AGC ACA CTG CAG GCC GAG TGT GAC CAG TAC CGC AGC ATC CTG GCG GAG     2112
Ser Thr Leu Gln Ala Glu Cys Asp Gln Tyr Arg Ser Ile Leu Ala Glu
    690                 695                 700

ACG GAG GGC ATG CTC AGA GAC CTG CAG AAG AGC GTG GAG GAG GAG GAG     2160
Thr Glu Gly Met Leu Arg Asp Leu Gln Lys Ser Val Glu Glu Glu Glu
705                 710                 715                 720

CAG GTG TGG AGG GCC AAG GTG GGC GCC GCA GAG GAG GAG CTC CAG AAG     2208
Gln Val Trp Arg Ala Lys Val Gly Ala Ala Glu Glu Glu Leu Gln Lys
                725                 730                 735

TCC CGG GTC ACA GTG AAG CAT CTC GAA GAG ATT GTA GAG AAG CTA AAA     2256
Ser Arg Val Thr Val Lys His Leu Glu Glu Ile Val Glu Lys Leu Lys
            740                 745                 750

GGA GAA CTT GAA AGT TCG GAC CAG GTG AGG GAG CAC ACG TCG CAT TTG     2304
Gly Glu Leu Glu Ser Ser Asp Gln Val Arg Glu His Thr Ser His Leu
        755                 760                 765

GAG GCA GAG CTG GAA AAG CAC ATG GCG GCC GCC AGC GCC GAG TGC CAG     2352
Glu Ala Glu Leu Glu Lys His Met Ala Ala Ala Ser Ala Glu Cys Gln
    770                 775                 780

AAC TAC GCC AAG GAG GTG GCA GGG CTG AGG CAA CTT CTC CTA GAA TCT     2400
Asn Tyr Ala Lys Glu Val Ala Gly Leu Arg Gln Leu Leu Leu Glu Ser
785                 790                 795                 800

CAA TCT CAG CTC GAT GCC GCC AAG AGC GAA GCC CAG AAA CAG AGC GAT     2448
Gln Ser Gln Leu Asp Ala Ala Lys Ser Glu Ala Gln Lys Gln Ser Asp
                805                 810                 815

GAG CTT GCC CTG GTC AGG CAG CAG TTG AGT GAA ATG AAG AGC CAC GTA     2496
Glu Leu Ala Leu Val Arg Gln Gln Leu Ser Glu Met Lys Ser His Val
            820                 825                 830

GAG GAT GGT GAC ATA GCT GGG GCC CCA GCT TCC TCC CCA GAG GCG CCC     2544
Glu Asp Gly Asp Ile Ala Gly Ala Pro Ala Ser Ser Pro Glu Ala Pro
        835                 840                 845

CCA GCC GAG CAG GAC CCC GTT CAG CTG AAG ACG CAG CTG GAG TGG ACA     2592
Pro Ala Glu Gln Asp Pro Val Gln Leu Lys Thr Gln Leu Glu Trp Thr
    850                 855                 860

GAA GCC ATC CTG GAG GAT GAG CAG ACA CAG CGG CAG AAG CTC ATG GCC     2640
Glu Ala Ile Leu Glu Asp Glu Gln Thr Gln Arg Gln Lys Leu Met Ala
865                 870                 875                 880

GAG TTT GAG GAG GCT CAG ACC TCG GCA TGT CGG TTA CAA GAA GAA TTG     2688
```

-continued

```
Glu Phe Glu Glu Ala Gln Thr Ser Ala Cys Arg Leu Gln Glu Glu Leu
                885                 890                 895

GAG AAG CTC CGC ACA GCC GGC CCC CTA GAG TCT TCA GAA ACA GAG GAG     2736
Glu Lys Leu Arg Thr Ala Gly Pro Leu Glu Ser Ser Glu Thr Glu Glu
            900                 905                 910

GCC TCA CAG CTG AAG GAG AGA CTA GAA AAA GAG AAG AAG TTA ACA AGT     2784
Ala Ser Gln Leu Lys Glu Arg Leu Glu Lys Glu Lys Lys Leu Thr Ser
        915                 920                 925

GAC CTG GGG CGC GCC GCC ACG AGA CTG CAG GAG CTT CTG AAG ACG ACC     2832
Asp Leu Gly Arg Ala Ala Thr Arg Leu Gln Glu Leu Leu Lys Thr Thr
    930                 935                 940

CAG GAG CAG CTG GCA AGG GAG AAG GAC ACG GTG AAG AAG CTG CAG GAA     2880
Gln Glu Gln Leu Ala Arg Glu Lys Asp Thr Val Lys Lys Leu Gln Glu
945                 950                 955                 960

CAG CTG GAA AAG GCA GAG GAC GGC AGC AGC TCA AAG GAG GGC ACC TCT     2928
Gln Leu Glu Lys Ala Glu Asp Gly Ser Ser Ser Lys Glu Gly Thr Ser
                965                 970                 975

GTC TGA                                                             2934
Val
```

(2) INFORMATION FOR SEQ ID NO: 18:

(i) SEQUENCE CHARACTERISTICS:
(A) LENGTH: 977 amino acids
(B) TYPE: amino acid
(D) TOPOLOGY: linear (ii) MOLECULE TYPE: protein (xi) SEQUENCE DESCRIPTION: SEQ ID NO: 18:

```
Met Asp Ile Tyr Asp Thr Gln Thr Leu Gly Val Val Val Phe Gly Gly
  1               5                  10                  15

Phe Met Val Val Ser Ala Ile Gly Ile Phe Leu Val Ser Thr Phe Ser
            20                  25                  30

Met Lys Glu Thr Ser Tyr Glu Glu Ala Leu Ala Asn Gln Arg Lys Glu
        35                  40                  45

Met Ala Lys Thr His His Gln Lys Val Glu Lys Lys Lys Lys Glu Lys
     50                  55                  60

Thr Val Glu Lys Lys Gly Lys Thr Lys Lys Lys Glu Glu Lys Pro Asn
 65                  70                  75                  80

Gly Lys Ile Pro Asp His Asp Pro Ala Pro Asn Val Thr Val Leu Leu
                 85                  90                  95

Arg Glu Pro Val Arg Ala Pro Ala Val Ala Val Ala Pro Thr Pro Val
            100                 105                 110

Gln Pro Pro Ile Ile Val Ala Pro Val Ala Thr Val Pro Ala Met Pro
        115                 120                 125

Gln Glu Lys Leu Ala Ser Ser Pro Lys Asp Lys Lys Lys Lys Glu Lys
    130                 135                 140

Lys Val Ala Lys Val Glu Pro Ala Val Ser Ser Val Val Asn Ser Ile
145                 150                 155                 160

Gln Val Leu Thr Ser Lys Ala Ala Ile Leu Glu Thr Ala Pro Lys Glu
                165                 170                 175

Gly Arg Asn Thr Asp Val Ala Gln Ser Pro Glu Ala Pro Lys Gln Glu
            180                 185                 190

Ala Pro Ala Lys Lys Lys Ser Gly Ser Lys Lys Lys Gly Pro Pro Asp
        195                 200                 205

Ala Asp Gly Pro Leu Tyr Leu Pro Tyr Lys Thr Leu Val Ser Thr Val
    210                 215                 220
```

-continued

```
Gly Ser Met Val Phe Asn Glu Gly Glu Ala Gln Arg Leu Ile Glu Ile
225                 230                 235                 240

Leu Ser Glu Lys Ala Gly Ile Ile Gln Asp Thr Trp His Lys Ala Thr
                245                 250                 255

Gln Lys Gly Asp Pro Val Ala Ile Leu Lys Arg Gln Leu Glu Glu Lys
            260                 265                 270

Glu Lys Leu Leu Ala Thr Glu Gln Glu Asp Ala Ala Val Ala Lys Ser
        275                 280                 285

Lys Leu Arg Glu Leu Asn Lys Glu Met Ala Ala Glu Lys Ala Lys Ala
    290                 295                 300

Ala Ala Gly Glu Ala Lys Val Lys Lys Gln Leu Val Ala Arg Glu Gln
305                 310                 315                 320

Glu Ile Thr Ala Val Gln Ala Arg Met Gln Ala Ser Tyr Arg Glu His
                325                 330                 335

Val Lys Glu Val Gln Gln Leu Gln Gly Lys Ile Arg Thr Leu Gln Glu
            340                 345                 350

Gln Leu Glu Asn Gly Pro Asn Thr Gln Leu Ala Arg Leu Gln Gln Glu
        355                 360                 365

Asn Ser Ile Leu Arg Asp Ala Leu Asn Gln Ala Thr Ser Gln Val Glu
    370                 375                 380

Ser Lys Gln Asn Ala Glu Leu Ala Lys Leu Arg Gln Glu Leu Ser Lys
385                 390                 395                 400

Val Ser Lys Glu Leu Val Glu Lys Ser Glu Ala Val Arg Gln Asp Glu
                405                 410                 415

Gln Gln Arg Lys Ala Leu Glu Ala Lys Ala Ala Ala Phe Glu Lys Gln
            420                 425                 430

Val Leu Gln Leu Gln Ala Ser His Arg Glu Ser Glu Glu Ala Leu Gln
        435                 440                 445

Lys Arg Leu Asp Glu Val Ser Arg Glu Leu Cys His Thr Gln Ser Ser
    450                 455                 460

His Ala Ser Leu Arg Ala Asp Ala Glu Lys Ala Gln Glu Gln Gln Gln
465                 470                 475                 480

Gln Met Ala Glu Leu His Ser Lys Leu Gln Ser Ser Glu Ala Glu Val
                485                 490                 495

Arg Ser Lys Cys Glu Glu Leu Ser Gly Leu His Gly Gln Leu Gln Glu
            500                 505                 510

Ala Arg Ala Glu Asn Ser Gln Leu Thr Glu Arg Ile Arg Ser Ile Glu
        515                 520                 525

Ala Leu Leu Glu Ala Gly Gln Ala Arg Asp Ala Gln Asp Val Gln Ala
    530                 535                 540

Ser Gln Ala Glu Ala Asp Gln Gln Gln Thr Arg Leu Lys Glu Leu Glu
545                 550                 555                 560

Ser Gln Val Ser Gly Leu Glu Lys Glu Ala Ile Glu Leu Arg Glu Ala
                565                 570                 575

Val Glu Gln Gln Lys Val Lys Asn Asn Asp Leu Arg Glu Lys Asn Trp
            580                 585                 590

Lys Ala Met Glu Ala Leu Ala Thr Ala Glu Gln Ala Cys Lys Glu Lys
        595                 600                 605

Leu His Ser Leu Thr Gln Ala Lys Glu Glu Ser Glu Lys Gln Leu Cys
    610                 615                 620

Leu Ile Glu Ala Gln Thr Met Glu Ala Leu Leu Ala Leu Leu Pro Glu
625                 630                 635                 640
```

-continued

```
Leu Ser Val Leu Ala Gln Gln Asn Tyr Thr Glu Trp Leu Gln Asp Leu
                645                 650                 655

Lys Glu Lys Gly Pro Thr Leu Leu Lys His Pro Pro Ala Pro Ala Glu
            660                 665                 670

Pro Ser Ser Asp Leu Ala Ser Lys Leu Arg Glu Ala Glu Glu Thr Gln
        675                 680                 685

Ser Thr Leu Gln Ala Glu Cys Asp Gln Tyr Arg Ser Ile Leu Ala Glu
    690                 695                 700

Thr Glu Gly Met Leu Arg Asp Leu Gln Lys Ser Val Glu Glu Glu Glu
705                 710                 715                 720

Gln Val Trp Arg Ala Lys Val Gly Ala Ala Glu Glu Glu Leu Gln Lys
                725                 730                 735

Ser Arg Val Thr Val Lys His Leu Glu Glu Ile Val Glu Lys Leu Lys
            740                 745                 750

Gly Glu Leu Glu Ser Ser Asp Gln Val Arg Glu His Thr Ser His Leu
        755                 760                 765

Glu Ala Glu Leu Glu Lys His Met Ala Ala Ala Ser Ala Glu Cys Gln
    770                 775                 780

Asn Tyr Ala Lys Glu Val Ala Gly Leu Arg Gln Leu Leu Leu Glu Ser
785                 790                 795                 800

Gln Ser Gln Leu Asp Ala Ala Lys Ser Glu Ala Gln Lys Gln Ser Asp
                805                 810                 815

Glu Leu Ala Leu Val Arg Gln Gln Leu Ser Glu Met Lys Ser His Val
            820                 825                 830

Glu Asp Gly Asp Ile Ala Gly Ala Pro Ala Ser Ser Pro Glu Ala Pro
        835                 840                 845

Pro Ala Glu Gln Asp Pro Val Gln Leu Lys Thr Gln Leu Glu Trp Thr
    850                 855                 860

Glu Ala Ile Leu Glu Asp Glu Gln Thr Gln Arg Gln Lys Leu Met Ala
865                 870                 875                 880

Glu Phe Glu Glu Ala Gln Thr Ser Ala Cys Arg Leu Gln Glu Glu Leu
                885                 890                 895

Glu Lys Leu Arg Thr Ala Gly Pro Leu Glu Ser Ser Glu Thr Glu Glu
            900                 905                 910

Ala Ser Gln Leu Lys Glu Arg Leu Glu Lys Glu Lys Lys Leu Thr Ser
        915                 920                 925

Asp Leu Gly Arg Ala Ala Thr Arg Leu Gln Glu Leu Leu Lys Thr Thr
    930                 935                 940

Gln Glu Gln Leu Ala Arg Glu Lys Asp Thr Val Lys Lys Leu Gln Glu
945                 950                 955                 960

Gln Leu Glu Lys Ala Glu Asp Gly Ser Ser Ser Lys Glu Gly Thr Ser
                965                 970                 975

Val
```

(2) INFORMATION FOR SEQ ID NO: 19:

(i) SEQUENCE CHARACTERISTICS:
(A) LENGTH: 1587 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..1584

-continued (xi) SEQUENCE DESCRIPTION: SEQ ID NO: 19:

```
ATG GCC CAG CTG TTC CTG CCC CTG CTG GCA GCC CTG GTC CTG GCC CAG       48
Met Ala Gln Leu Phe Leu Pro Leu Leu Ala Ala Leu Val Leu Ala Gln
  1               5                  10                  15

GCT CCT GCA GCT TTA GCA GAT GTT CTG GAA GGA GAC AGC TCA GAG GAC       96
Ala Pro Ala Ala Leu Ala Asp Val Leu Glu Gly Asp Ser Ser Glu Asp
             20                  25                  30

CGC GCT TTT CGC GTG CGC ATC GCG GGC GAC GCG CCA CTG CAG GGC GTG      144
Arg Ala Phe Arg Val Arg Ile Ala Gly Asp Ala Pro Leu Gln Gly Val
         35                  40                  45

CTC GGC GGC GCC CTC ACC ATC CCT TGC CAC GTC CAC TAC CTG CGG CCA      192
Leu Gly Gly Ala Leu Thr Ile Pro Cys His Val His Tyr Leu Arg Pro
     50                  55                  60

CCG CCG AGC CGC CGG GCT GTG CTG GGC TCT CCG CGG GTC AAG TGG ACT      240
Pro Pro Ser Arg Arg Ala Val Leu Gly Ser Pro Arg Val Lys Trp Thr
 65                  70                  75                  80

TTC CTG TCC CGG GGC CGG GAG GCA GAG GTG CTG GTG GCG CGG GGA GTG      288
Phe Leu Ser Arg Gly Arg Glu Ala Glu Val Leu Val Ala Arg Gly Val
                 85                  90                  95

CGC GTC AAG GTG AAC GAG GCC TAC CGG TTC CGC GTG GCA CTG CCT GCG      336
Arg Val Lys Val Asn Glu Ala Tyr Arg Phe Arg Val Ala Leu Pro Ala
            100                 105                 110

TAC CCA GCG TCG CTC ACC GAC GTC TCC CTG GCG CTG AGC GAG CTG CGC      384
Tyr Pro Ala Ser Leu Thr Asp Val Ser Leu Ala Leu Ser Glu Leu Arg
        115                 120                 125

CCC AAC GAC TCA GGT ATC TAT CGC TGT GAG GTC CAG CAC GGC ATC GAT      432
Pro Asn Asp Ser Gly Ile Tyr Arg Cys Glu Val Gln His Gly Ile Asp
    130                 135                 140

GAC AGC AGC GAC GCT GTG GAG TCA AGT CAA AGG TAT CCC ATC CAG ACC      480
Asp Ser Ser Asp Ala Val Glu Ser Ser Gln Arg Tyr Pro Ile Gln Thr
145                 150                 155                 160

CCA CGA GAG GCC TGT TAC GGA GAC ATG GAT GGC TTC CCC GGG GTC CGG      528
Pro Arg Glu Ala Cys Tyr Gly Asp Met Asp Gly Phe Pro Gly Val Arg
                165                 170                 175

AAC TAT GGT GTG GTG GAC CCG GAT GAC CTC TAT GAT GTG TAC TGT TAT      576
Asn Tyr Gly Val Val Asp Pro Asp Asp Leu Tyr Asp Val Tyr Cys Tyr
            180                 185                 190

GCT GAA GAC CTA AAT GGA GAA CTG TTC CTG GGT GAC CCT CCA GAG AAG      624
Ala Glu Asp Leu Asn Gly Glu Leu Phe Leu Gly Asp Pro Pro Glu Lys
        195                 200                 205

CTG ACA TTG GAG GAA GCA CGG GCG TAC TGC CAG GAG CGG GGT GCA GAG      672
Leu Thr Leu Glu Glu Ala Arg Ala Tyr Cys Gln Glu Arg Gly Ala Glu
    210                 215                 220

ATT GCC ACC ACG GGC CAA CTG TAT GCA GCC TGG GAT GGT GGC CTG GAC      720
Ile Ala Thr Thr Gly Gln Leu Tyr Ala Ala Trp Asp Gly Gly Leu Asp
225                 230                 235                 240

CAC TGC AGC CCA GGG TGG CTA GCT GAT GGC AGT GTG CGC TAC CCC ATC      768
His Cys Ser Pro Gly Trp Leu Ala Asp Gly Ser Val Arg Tyr Pro Ile
                245                 250                 255

GTC ACA CCC AGC CAG CGC TGT GGT GGG GGC TTG CCT GGT GTC AAG ACT      816
Val Thr Pro Ser Gln Arg Cys Gly Gly Gly Leu Pro Gly Val Lys Thr
            260                 265                 270

CTC TTC CTC TTC CCC AAC CAG ACT GGC TTC CCC AAT AAG CAC AGC CGC      864
Leu Phe Leu Phe Pro Asn Gln Thr Gly Phe Pro Asn Lys His Ser Arg
        275                 280                 285

TTC AAC GTC TAC TGC TTC CGA GAC TCG GCC CAG CTT CTG CCA TCC CTG      912
Phe Asn Val Tyr Cys Phe Arg Asp Ser Ala Gln Leu Leu Pro Ser Leu
    290                 295                 300
```

-continued

```
AGG CCT CCA ACC CAG CCT CCA ACC CAG CTT GAT GGA CTA GAG GCT ATC       960
Arg Pro Pro Thr Gln Pro Pro Thr Gln Leu Asp Gly Leu Glu Ala Ile
305                 310                 315                 320

GTC ACA GTG ACA GAG ACC CTG GAG GAA CTG CAG CTG CCT CAG GAA GCC      1008
Val Thr Val Thr Glu Thr Leu Glu Glu Leu Gln Leu Pro Gln Glu Ala
                325                 330                 335

ACA GAG AGT GAA TCC CGT GGG GCC ATC TAC TCC ATC CCC ATC ATG GAG      1056
Thr Glu Ser Glu Ser Arg Gly Ala Ile Tyr Ser Ile Pro Ile Met Glu
            340                 345                 350

GAC GGA GGA GGT GGA AGC TCC ACT CCA GAA GAC CCA GCA GAG GCC CCT      1104
Asp Gly Gly Gly Gly Ser Ser Thr Pro Glu Asp Pro Ala Glu Ala Pro
        355                 360                 365

AGG ACG CTC CTA GAA TTT GAA ACA CAA TCC ATG GTA CCG CCC ACG GGG      1152
Arg Thr Leu Leu Glu Phe Glu Thr Gln Ser Met Val Pro Pro Thr Gly
    370                 375                 380

TTT TCA GAA GAG GAA GGT AAG GCA TTG GAG GAA GAA GAG AAA TAT GAA      1200
Phe Ser Glu Glu Glu Gly Lys Ala Leu Glu Glu Glu Glu Lys Tyr Glu
385                 390                 395                 400

GAT GAA GAA GAG AAA GAG GAG GAA GAA GAA GAG GAG GAG GTG GAG GAT      1248
Asp Glu Glu Glu Lys Glu Glu Glu Glu Glu Glu Glu Glu Val Glu Asp
                405                 410                 415

GAG GCT CTG TGG GCA TGG CCC AGC GAG CTC AGC AGC CCG GGC CCT GAG      1296
Glu Ala Leu Trp Ala Trp Pro Ser Glu Leu Ser Ser Pro Gly Pro Glu
            420                 425                 430

GCC TCT CTC CCC ACT GAG CCA GCA GCC CAG GAG GAG TCA CTC TCC CAG      1344
Ala Ser Leu Pro Thr Glu Pro Ala Ala Gln Glu Glu Ser Leu Ser Gln
        435                 440                 445

GCG CCA GCA AGG GCA GTC CTG CAG CCT GGT GCA TCA CCA CTT CCT GAT      1392
Ala Pro Ala Arg Ala Val Leu Gln Pro Gly Ala Ser Pro Leu Pro Asp
    450                 455                 460

GGA GAG TCA GAA GCT TCC AGG CCT CCA AGG GTC CAT GGA CCA CCT ACT      1440
Gly Glu Ser Glu Ala Ser Arg Pro Pro Arg Val His Gly Pro Pro Thr
465                 470                 475                 480

GAG ACT CTG CCC ACT CCC AGG GAG AGG AAC CTA GCA TCC CCA TCA CCT      1488
Glu Thr Leu Pro Thr Pro Arg Glu Arg Asn Leu Ala Ser Pro Ser Pro
                485                 490                 495

TCC ACT CTG GTT GAG GCA AGA GAG GTG GGG GAG GCA ACT GGT GGT CCT      1536
Ser Thr Leu Val Glu Ala Arg Glu Val Gly Glu Ala Thr Gly Gly Pro
            500                 505                 510

GAG CTA TCT GGG GTC CCT CGA GGG GGG GCC CGT ACC CAA TTC GCC CTA      1584
Glu Leu Ser Gly Val Pro Arg Gly Gly Ala Arg Thr Gln Phe Ala Leu
        515                 520                 525

TAG                                                                  1587
```

(2) INFORMATION FOR SEQ ID NO: 20:

(i) SEQUENCE CHARACTERISTICS:
(A) LENGTH: 528 amino acids
(B) TYPE: amino acid
(D) TOPOLOGY: linear (ii) MOLECULE TYPE: protein (xi) SEQUENCE DESCRIPTION: SEQ ID NO: 20:

```
Met Ala Gln Leu Phe Leu Pro Leu Leu Ala Ala Leu Val Leu Ala Gln
  1               5                  10                  15

Ala Pro Ala Ala Leu Ala Asp Val Leu Glu Gly Asp Ser Ser Glu Asp
             20                  25                  30

Arg Ala Phe Arg Val Arg Ile Ala Gly Asp Ala Pro Leu Gln Gly Val
        35                  40                  45
```

-continued

```
Leu Gly Gly Ala Leu Thr Ile Pro Cys His Val His Tyr Leu Arg Pro
     50                  55                  60

Pro Pro Ser Arg Arg Ala Val Leu Gly Ser Pro Arg Val Lys Trp Thr
 65                  70                  75                  80

Phe Leu Ser Arg Gly Arg Glu Ala Glu Val Leu Val Ala Arg Gly Val
                 85                  90                  95

Arg Val Lys Val Asn Glu Ala Tyr Arg Phe Arg Val Ala Leu Pro Ala
            100                 105                 110

Tyr Pro Ala Ser Leu Thr Asp Val Ser Leu Ala Leu Ser Glu Leu Arg
        115                 120                 125

Pro Asn Asp Ser Gly Ile Tyr Arg Cys Glu Val Gln His Gly Ile Asp
    130                 135                 140

Asp Ser Ser Asp Ala Val Glu Ser Ser Gln Arg Tyr Pro Ile Gln Thr
145                 150                 155                 160

Pro Arg Glu Ala Cys Tyr Gly Asp Met Asp Gly Phe Pro Gly Val Arg
                165                 170                 175

Asn Tyr Gly Val Val Asp Pro Asp Asp Leu Tyr Asp Val Tyr Cys Tyr
            180                 185                 190

Ala Glu Asp Leu Asn Gly Glu Leu Phe Leu Gly Asp Pro Pro Glu Lys
        195                 200                 205

Leu Thr Leu Glu Glu Ala Arg Ala Tyr Cys Gln Glu Arg Gly Ala Glu
    210                 215                 220

Ile Ala Thr Thr Gly Gln Leu Tyr Ala Ala Trp Asp Gly Gly Leu Asp
225                 230                 235                 240

His Cys Ser Pro Gly Trp Leu Ala Asp Gly Ser Val Arg Tyr Pro Ile
                245                 250                 255

Val Thr Pro Ser Gln Arg Cys Gly Gly Gly Leu Pro Gly Val Lys Thr
            260                 265                 270

Leu Phe Leu Phe Pro Asn Gln Thr Gly Phe Pro Asn Lys His Ser Arg
        275                 280                 285

Phe Asn Val Tyr Cys Phe Arg Asp Ser Ala Gln Leu Leu Pro Ser Leu
    290                 295                 300

Arg Pro Pro Thr Gln Pro Pro Thr Gln Leu Asp Gly Leu Glu Ala Ile
305                 310                 315                 320

Val Thr Val Thr Glu Thr Leu Glu Glu Leu Gln Leu Pro Gln Glu Ala
                325                 330                 335

Thr Glu Ser Glu Ser Arg Gly Ala Ile Tyr Ser Ile Pro Ile Met Glu
            340                 345                 350

Asp Gly Gly Gly Gly Ser Ser Thr Pro Glu Asp Pro Ala Glu Ala Pro
        355                 360                 365

Arg Thr Leu Leu Glu Phe Glu Thr Gln Ser Met Val Pro Pro Thr Gly
    370                 375                 380

Phe Ser Glu Glu Glu Gly Lys Ala Leu Glu Glu Glu Glu Lys Tyr Glu
385                 390                 395                 400

Asp Glu Glu Glu Lys Glu Glu Glu Glu Glu Glu Glu Glu Val Glu Asp
                405                 410                 415

Glu Ala Leu Trp Ala Trp Pro Ser Glu Leu Ser Ser Pro Gly Pro Glu
            420                 425                 430

Ala Ser Leu Pro Thr Glu Pro Ala Ala Gln Glu Glu Ser Leu Ser Gln
        435                 440                 445

Ala Pro Ala Arg Ala Val Leu Gln Pro Gly Ala Ser Pro Leu Pro Asp
    450                 455                 460

Gly Glu Ser Glu Ala Ser Arg Pro Pro Arg Val His Gly Pro Pro Thr
```

-continued

```
465                 470                 475                 480

Glu Thr Leu Pro Thr Pro Arg Glu Arg Asn Leu Ala Ser Pro Ser Pro
                485                 490                 495

Ser Thr Leu Val Glu Ala Arg Glu Val Gly Glu Ala Thr Gly Gly Pro
            500                 505                 510

Glu Leu Ser Gly Val Pro Arg Gly Gly Ala Arg Thr Gln Phe Ala Leu
        515                 520                 525
```

(2) INFORMATION FOR SEQ ID NO: 21:

(i) SEQUENCE CHARACTERISTICS:
(A) LENGTH: 1359 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..1356

(xi) SEQUENCE DESCRIPTION: SEQ ID NO: 21:

```
ATG TCT GCC GAC GGG GCA GAG GCT GAT GGC AGC ACC CAG GTG ACA GTG       48
Met Ser Ala Asp Gly Ala Glu Ala Asp Gly Ser Thr Gln Val Thr Val
  1               5                  10                  15

GAA GAA CCG GTA CAG CAG CCC AGT GTG GTG GAC CGT GTG GCC AGC ATG       96
Glu Glu Pro Val Gln Gln Pro Ser Val Val Asp Arg Val Ala Ser Met
             20                  25                  30

CCT CTG ATC AGC TCC ACC TGC GAC ATG GTG TCC GCA GCC TAT GCC TCC      144
Pro Leu Ile Ser Ser Thr Cys Asp Met Val Ser Ala Ala Tyr Ala Ser
         35                  40                  45

ACC AAG GAG AGC TAC CCG CAC GTC AAG ACT GTC TGC GAC GCA GCA GAG      192
Thr Lys Glu Ser Tyr Pro His Val Lys Thr Val Cys Asp Ala Ala Glu
     50                  55                  60

AAG GGA GTG AGG ACC CTC ACG GCG GCT GCT GTC AGC GGG GCT CAG CCG      240
Lys Gly Val Arg Thr Leu Thr Ala Ala Ala Val Ser Gly Ala Gln Pro
 65                  70                  75                  80

ATC CTC TCC AAG CTG GAG CCC CAG ATT GCA TCA GCC AGC GAA TAC GCC      288
Ile Leu Ser Lys Leu Glu Pro Gln Ile Ala Ser Ala Ser Glu Tyr Ala
                 85                  90                  95

CAC AGG GGG CTG GAC AAG TTG GAG GAG AAC CTC CCC ATC CTG CAG CAG      336
His Arg Gly Leu Asp Lys Leu Glu Glu Asn Leu Pro Ile Leu Gln Gln
            100                 105                 110

CCC ACG GAG AAG TCC TGG CGG ACA CAA CGA CTT GTG TCG TCT AAA GTG      384
Pro Thr Glu Lys Ser Trp Arg Thr Gln Arg Leu Val Ser Ser Lys Val
        115                 120                 125

TCG GGG CCC AAG AAA TGG TGT CTA GCG CCA ACG ACA CGG TGG CCA CCA      432
Ser Gly Pro Lys Lys Trp Cys Leu Ala Pro Thr Thr Arg Trp Pro Pro
    130                 135                 140

ATT GTC GGA GCG GTG GAC GCG ACC CGC GGT GCT GTG CAG AGC GGC GTG      480
Ile Val Gly Ala Val Asp Ala Thr Arg Gly Ala Val Gln Ser Gly Val
145                 150                 155                 160

GAC AAG ACA AAG TCC GTA GTG ACC GGC GGC GTC CAA TCG GTC ATG GGC      528
Asp Lys Thr Lys Ser Val Val Thr Gly Gly Val Gln Ser Val Met Gly
                165                 170                 175

TCC CGC TTG GGC GGC ACG AGG CTG AGT GGG GTC GAC ACG GTG CTG GGG      576
Ser Arg Leu Gly Gly Thr Arg Leu Ser Gly Val Asp Thr Val Leu Gly
            180                 185                 190

AAG TCG GAG GAG TGG GCG GAC AAC CAC CTG CCC CTT ACG GAT GCC GAA      624
Lys Ser Glu Glu Trp Ala Asp Asn His Leu Pro Leu Thr Asp Ala Glu
        195                 200                 205
```

-continued

```
CTG GCC CGC ATC GCC ACA TCC CTG GAT GGC TTC GAC GTC GCG TCC GTG      672
Leu Ala Arg Ile Ala Thr Ser Leu Asp Gly Phe Asp Val Ala Ser Val
    210                 215                 220

CAG CAG CAG CGG CAG GAA CAG AGC TAC TTC GTA CGT CTG GGC TCC CTG      720
Gln Gln Gln Arg Gln Glu Gln Ser Tyr Phe Val Arg Leu Gly Ser Leu
225                 230                 235                 240

TCG GAG AGG CTG CGG CAG CAC GCC TAT GAG CAC TCG CTG GGC AAG CTT      768
Ser Glu Arg Leu Arg Gln His Ala Tyr Glu His Ser Leu Gly Lys Leu
                245                 250                 255

CGA GCC ACC AAG CAG AGG GCA CAG GAG GCT CTG CTG CAG CTG TCG CAG      816
Arg Ala Thr Lys Gln Arg Ala Gln Glu Ala Leu Leu Gln Leu Ser Gln
            260                 265                 270

GCC CTA AGC CTG ATG GAA ACT GTC AAG CAA GGC GTT GAT CAG AAG CTG      864
Ala Leu Ser Leu Met Glu Thr Val Lys Gln Gly Val Asp Gln Lys Leu
        275                 280                 285

GTG GAA GGC CAG GAG AAG CTG CAC CAG ATG TGG CTC AGC TGG AAC CAG      912
Val Glu Gly Gln Glu Lys Leu His Gln Met Trp Leu Ser Trp Asn Gln
    290                 295                 300

AAG CAA CTC CAG GGC CCC GAG AAG GAG CCG CCC AAG CCA GAG CAG GTC      960
Lys Gln Leu Gln Gly Pro Glu Lys Glu Pro Pro Lys Pro Glu Gln Val
305                 310                 315                 320

GAG TCC CGG GCG CTC ACC ATG TTC CGG GAC ATT GCC CAG CAA CTG CAG     1008
Glu Ser Arg Ala Leu Thr Met Phe Arg Asp Ile Ala Gln Gln Leu Gln
                325                 330                 335

GCC ACC TGT ACC TCC CTG GGG TCC AGC ATT CAG GGC CTC CCC ACC AAT     1056
Ala Thr Cys Thr Ser Leu Gly Ser Ser Ile Gln Gly Leu Pro Thr Asn
            340                 345                 350

GTG AAG GAC CAG GTG CAG CAG GCC CGC CGC CAG GTG GAT GAC CTC CAT     1104
Val Lys Asp Gln Val Gln Gln Ala Arg Arg Gln Val Asp Asp Leu His
        355                 360                 365

GCC ACG TTT TCC AAC ATC CAC TCC TTC CAG GAC CTG TCC AGC AAC AAT     1152
Ala Thr Phe Ser Asn Ile His Ser Phe Gln Asp Leu Ser Ser Asn Asn
    370                 375                 380

TCT GGC CCA GAG CCG TTA GTG TTC GCC AGC GCC CGC GAG GCC CTG GAC     1200
Ser Gly Pro Glu Pro Leu Val Phe Ala Ser Ala Arg Glu Ala Leu Asp
385                 390                 395                 400

CAC ATG GTG GGA ATG ATG TGG CCC ACA ACT CCC CTG TTT CCA TGG TCT     1248
His Met Val Gly Met Met Trp Pro Thr Thr Pro Leu Phe Pro Trp Ser
                405                 410                 415

CTG TTG GGG ACC CTT TTG CCC CTT GTG ATT CAC TCG AGA AAG CCC CCA     1296
Leu Leu Gly Thr Leu Leu Pro Leu Val Ile His Ser Arg Lys Pro Pro
            420                 425                 430

GAG GCA AAA CAA TTT TGG GGA CAG GAG AGG ACT CAG CGG GCT CCC GTC     1344
Glu Ala Lys Gln Phe Trp Gly Gln Glu Arg Thr Gln Arg Ala Pro Val
        435                 440                 445

TCT ATA ATG CAG TGA                                                 1359
Ser Ile Met Gln
    450
```

(2) INFORMATION FOR SEQ ID NO: 22:

(i) SEQUENCE CHARACTERISTICS:
(A) LENGTH: 452 amino acids
(B) TYPE: amino acid
(D) TOPOLOGY: linear (ii) MOLECULE TYPE: protein (xi) SEQUENCE DESCRIPTION: SEQ ID NO: 22:

```
Met Ser Ala Asp Gly Ala Glu Ala Asp Gly Ser Thr Gln Val Thr Val
  1               5                  10                  15
```

-continued

```
Glu Glu Pro Val Gln Gln Pro Ser Val Val Asp Arg Val Ala Ser Met
            20                  25                  30

Pro Leu Ile Ser Ser Thr Cys Asp Met Val Ser Ala Ala Tyr Ala Ser
        35                  40                  45

Thr Lys Glu Ser Tyr Pro His Val Lys Thr Val Cys Asp Ala Ala Glu
    50                  55                  60

Lys Gly Val Arg Thr Leu Thr Ala Ala Ala Val Ser Gly Ala Gln Pro
65                  70                  75                  80

Ile Leu Ser Lys Leu Glu Pro Gln Ile Ala Ser Ala Ser Glu Tyr Ala
                85                  90                  95

His Arg Gly Leu Asp Lys Leu Glu Glu Asn Leu Pro Ile Leu Gln Gln
            100                 105                 110

Pro Thr Glu Lys Ser Trp Arg Thr Gln Arg Leu Val Ser Ser Lys Val
        115                 120                 125

Ser Gly Pro Lys Lys Trp Cys Leu Ala Pro Thr Thr Arg Trp Pro Pro
    130                 135                 140

Ile Val Gly Ala Val Asp Ala Thr Arg Gly Ala Val Gln Ser Gly Val
145                 150                 155                 160

Asp Lys Thr Lys Ser Val Val Thr Gly Gly Val Gln Ser Val Met Gly
                165                 170                 175

Ser Arg Leu Gly Gly Thr Arg Leu Ser Gly Val Asp Thr Val Leu Gly
            180                 185                 190

Lys Ser Glu Glu Trp Ala Asp Asn His Leu Pro Leu Thr Asp Ala Glu
        195                 200                 205

Leu Ala Arg Ile Ala Thr Ser Leu Asp Gly Phe Asp Val Ala Ser Val
    210                 215                 220

Gln Gln Gln Arg Gln Glu Gln Ser Tyr Phe Val Arg Leu Gly Ser Leu
225                 230                 235                 240

Ser Glu Arg Leu Arg Gln His Ala Tyr Glu His Ser Leu Gly Lys Leu
                245                 250                 255

Arg Ala Thr Lys Gln Arg Ala Gln Glu Ala Leu Leu Gln Leu Ser Gln
            260                 265                 270

Ala Leu Ser Leu Met Glu Thr Val Lys Gln Gly Val Asp Gln Lys Leu
        275                 280                 285

Val Glu Gly Gln Glu Lys Leu His Gln Met Trp Leu Ser Trp Asn Gln
    290                 295                 300

Lys Gln Leu Gln Gly Pro Glu Lys Glu Pro Pro Lys Pro Glu Gln Val
305                 310                 315                 320

Glu Ser Arg Ala Leu Thr Met Phe Arg Asp Ile Ala Gln Gln Leu Gln
                325                 330                 335

Ala Thr Cys Thr Ser Leu Gly Ser Ser Ile Gln Gly Leu Pro Thr Asn
            340                 345                 350

Val Lys Asp Gln Val Gln Gln Ala Arg Arg Gln Val Asp Asp Leu His
        355                 360                 365

Ala Thr Phe Ser Asn Ile His Ser Phe Gln Asp Leu Ser Ser Asn Asn
    370                 375                 380

Ser Gly Pro Glu Pro Leu Val Phe Ala Ser Ala Arg Glu Ala Leu Asp
385                 390                 395                 400

His Met Val Gly Met Met Trp Pro Thr Thr Pro Leu Phe Pro Trp Ser
                405                 410                 415

Leu Leu Gly Thr Leu Leu Pro Leu Val Ile His Ser Arg Lys Pro Pro
            420                 425                 430
```

-continued

```
Glu Ala Lys Gln Phe Trp Gly Gln Glu Arg Thr Gln Arg Ala Pro Val
        435                 440                 445

Ser Ile Met Gln
    450


(2) INFORMATION FOR SEQ ID NO: 23:

     (i) SEQUENCE CHARACTERISTICS:
          (A) LENGTH: 1098 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: CDS
          (B) LOCATION: 1..1095

    (xi) SEQUENCE DESCRIPTION: SEQ ID NO: 23:

ATG GCG ACC CCA GCC TCG GCC CCA GAC ACA CGG GCT CTG GTG GCA GAC        48
Met Ala Thr Pro Ala Ser Ala Pro Asp Thr Arg Ala Leu Val Ala Asp
  1               5                  10                  15

TTT GTA GGT TAT AAG CTG AGG CAG AAG GGT TAT GTC TGT GGA GCT GGC        96
Phe Val Gly Tyr Lys Leu Arg Gln Lys Gly Tyr Val Cys Gly Ala Gly
             20                  25                  30

CCC GGG GAG GGC CCA GCA GCT GAC CCG CTG CAC CAA GCC ATG CGG GCA       144
Pro Gly Glu Gly Pro Ala Ala Asp Pro Leu His Gln Ala Met Arg Ala
         35                  40                  45

GCT GGA GAT GAG TTC GAG ACC CGC TTC CGG CGC ACC TTC TCT GAT CTG       192
Ala Gly Asp Glu Phe Glu Thr Arg Phe Arg Arg Thr Phe Ser Asp Leu
     50                  55                  60

GCG GCT CAG CTG CAT GTG ACC CCA GGC TCA GCC CAA CAA CGC TTC ACC       240
Ala Ala Gln Leu His Val Thr Pro Gly Ser Ala Gln Gln Arg Phe Thr
 65                  70                  75                  80

CAG GTC TCC GAT GAA CTT TTT CAA GGG GGC CCC AAC TGG GGC CGC CTT       288
Gln Val Ser Asp Glu Leu Phe Gln Gly Gly Pro Asn Trp Gly Arg Leu
                 85                  90                  95

GTA GCC TTC TTT GTC TTT GGG GCT GCA CTG TGT GCT GAG AGT GTC AAC       336
Val Ala Phe Phe Val Phe Gly Ala Ala Leu Cys Ala Glu Ser Val Asn
            100                 105                 110

AAG GAG ATG GAA CCA CTG GTG GGA CAA GTG CAG GAG TGG ATG GTG GCC       384
Lys Glu Met Glu Pro Leu Val Gly Gln Val Gln Glu Trp Met Val Ala
        115                 120                 125

TAC CTG GAG ACG CGG CTG GCT GAC TGG ATC CAC AGC AGT GGG GGC TGG       432
Tyr Leu Glu Thr Arg Leu Ala Asp Trp Ile His Ser Ser Gly Gly Trp
    130                 135                 140

TTA TCC CAG ATC ACT GAA GCT GAG ATG GCT GAT GAA GTA ATT TGC AGT       480
Leu Ser Gln Ile Thr Glu Ala Glu Met Ala Asp Glu Val Ile Cys Ser
145                 150                 155                 160

GAA ATT TTA AGC GAC TGT GAC TCT GCT GCA AGT TCC CCA GAT CTT GAG       528
Glu Ile Leu Ser Asp Cys Asp Ser Ala Ala Ser Ser Pro Asp Leu Glu
                165                 170                 175

GAG CTG GAA GCT ATC AAA GCT CGA GTC AGG GAG ATG GAG GAA GAA GCT       576
Glu Leu Glu Ala Ile Lys Ala Arg Val Arg Glu Met Glu Glu Glu Ala
            180                 185                 190

GAG AAG CTA AAG GAG CTA CAG AAC GAG GTA GAG AAG CAG ATG AAT ATG       624
Glu Lys Leu Lys Glu Leu Gln Asn Glu Val Glu Lys Gln Met Asn Met
        195                 200                 205

AGT CCA CCT CCA GGC AAT GCT GGC CCG GTG ATC ATG TCC ATT GAG GAG       672
Ser Pro Pro Pro Gly Asn Ala Gly Pro Val Ile Met Ser Ile Glu Glu
    210                 215                 220
```

-continued

```
AAG ATG GAG GCT GAT GCC CGT TCC ATC TAT GTT GGC AAT GTG GAC TAT      720
Lys Met Glu Ala Asp Ala Arg Ser Ile Tyr Val Gly Asn Val Asp Tyr
225                 230                 235                 240

GGT GCA ACA GCA GAA GAG CTG GAA GCT CAC TTT CAT GGC TGT GGT TCA      768
Gly Ala Thr Ala Glu Glu Leu Glu Ala His Phe His Gly Cys Gly Ser
                245                 250                 255

GTC AAC CGT GTT ACC ATA CTG TGT GAC AAA TTT AGT GGC CAT CCC AAA      816
Val Asn Arg Val Thr Ile Leu Cys Asp Lys Phe Ser Gly His Pro Lys
            260                 265                 270

GGG TTT GCG TAT ATA GAG TTC TCA GAC AAA GAG TCA GTG AGG ACT TCC      864
Gly Phe Ala Tyr Ile Glu Phe Ser Asp Lys Glu Ser Val Arg Thr Ser
        275                 280                 285

TTG GCC TTA GAT GAG TCC CTA TTT AGA GGA AGG CAA ATC AAG GTG ATC      912
Leu Ala Leu Asp Glu Ser Leu Phe Arg Gly Arg Gln Ile Lys Val Ile
    290                 295                 300

CCA AAA CGA ACC AAC AGA CCA GGC ATC AGC ACA ACA GAC CGG GGT TTT      960
Pro Lys Arg Thr Asn Arg Pro Gly Ile Ser Thr Thr Asp Arg Gly Phe
305                 310                 315                 320

CCA CGA GCC CCG TAC CGC GCC CGG ACC ACC AAC TAC AAC AGC TCC CGC     1008
Pro Arg Ala Pro Tyr Arg Ala Arg Thr Thr Asn Tyr Asn Ser Ser Arg
                325                 330                 335

TCT CGA TTC TAC AGT GGT TTT AAC AGC AGG CCC CGG GGT CGC GTC TAC     1056
Ser Arg Phe Tyr Ser Gly Phe Asn Ser Arg Pro Arg Gly Arg Val Tyr
            340                 345                 350

AGG GGC CGG GCT AGA GCG ACA TCA TGG TAT TCC CCT TAC TAA             1098
Arg Gly Arg Ala Arg Ala Thr Ser Trp Tyr Ser Pro Tyr
        355                 360                 365
```

(2) INFORMATION FOR SEQ ID NO: 24:

(i) SEQUENCE CHARACTERISTICS:
(A) LENGTH: 365 amino acids
(B) TYPE: amino acid
(D) TOPOLOGY: linear (ii) MOLECULE TYPE: protein (xi) SEQUENCE DESCRIPTION: SEQ ID NO: 24:

```
Met Ala Thr Pro Ala Ser Ala Pro Asp Thr Arg Ala Leu Val Ala Asp
  1               5                  10                  15

Phe Val Gly Tyr Lys Leu Arg Gln Lys Gly Tyr Val Cys Gly Ala Gly
             20                  25                  30

Pro Gly Glu Gly Pro Ala Ala Asp Pro Leu His Gln Ala Met Arg Ala
         35                  40                  45

Ala Gly Asp Glu Phe Glu Thr Arg Phe Arg Arg Thr Phe Ser Asp Leu
     50                  55                  60

Ala Ala Gln Leu His Val Thr Pro Gly Ser Ala Gln Gln Arg Phe Thr
 65                  70                  75                  80

Gln Val Ser Asp Glu Leu Phe Gln Gly Gly Pro Asn Trp Gly Arg Leu
                 85                  90                  95

Val Ala Phe Phe Val Phe Gly Ala Ala Leu Cys Ala Glu Ser Val Asn
            100                 105                 110

Lys Glu Met Glu Pro Leu Val Gly Gln Val Gln Glu Trp Met Val Ala
        115                 120                 125

Tyr Leu Glu Thr Arg Leu Ala Asp Trp Ile His Ser Ser Gly Gly Trp
    130                 135                 140

Leu Ser Gln Ile Thr Glu Ala Glu Met Ala Asp Glu Val Ile Cys Ser
145                 150                 155                 160

Glu Ile Leu Ser Asp Cys Asp Ser Ala Ala Ser Ser Pro Asp Leu Glu
```

-continued

```
                165                 170                 175

Glu Leu Glu Ala Ile Lys Ala Arg Val Arg Glu Met Glu Glu Glu Ala
            180                 185                 190

Glu Lys Leu Lys Glu Leu Gln Asn Glu Val Glu Lys Gln Met Asn Met
        195                 200                 205

Ser Pro Pro Pro Gly Asn Ala Gly Pro Val Ile Met Ser Ile Glu Glu
    210                 215                 220

Lys Met Glu Ala Asp Ala Arg Ser Ile Tyr Val Gly Asn Val Asp Tyr
225                 230                 235                 240

Gly Ala Thr Ala Glu Glu Leu Glu Ala His Phe His Gly Cys Gly Ser
                245                 250                 255

Val Asn Arg Val Thr Ile Leu Cys Asp Lys Phe Ser Gly His Pro Lys
            260                 265                 270

Gly Phe Ala Tyr Ile Glu Phe Ser Asp Lys Glu Ser Val Arg Thr Ser
        275                 280                 285

Leu Ala Leu Asp Glu Ser Leu Phe Arg Gly Arg Gln Ile Lys Val Ile
    290                 295                 300

Pro Lys Arg Thr Asn Arg Pro Gly Ile Ser Thr Thr Asp Arg Gly Phe
305                 310                 315                 320

Pro Arg Ala Pro Tyr Arg Ala Arg Thr Thr Asn Tyr Asn Ser Ser Arg
                325                 330                 335

Ser Arg Phe Tyr Ser Gly Phe Asn Ser Arg Pro Arg Gly Arg Val Tyr
            340                 345                 350

Arg Gly Arg Ala Arg Ala Thr Ser Trp Tyr Ser Pro Tyr
        355                 360                 365
```

HUMAN CCV POLYPEPTIDES

This application claims benefit of 35 U.S.C. section 119(e) based on copending U.S. Provisional Application Ser. Nos. 60/034,204, filed Jan. 21, 1997 and 60/034,205, filed Jan. 21, 1997.

FIELD OF THE INVENTION

The present invention relates to genes encoding novel human proteins which exhibit a variety useful biological activities. More specifically, isolated nucleic acid molecules are provided which encode polypeptides comprising various forms of human proteins. Human polypeptides are also provided, as are vectors, host cells and recombinant methods for producing the same. Also provided are methods for detecting nucleic acids or polypeptides related to those of the invention, for example, to aid in identification of a biological sample or diagnosis of disorders related to expression of protein genes of this invention. The invention further relates to methods for identifying agonists and antagonists of the proteins of the invention, as well as to methods for treatment of disorders related to protein gene expression using polypeptides, antagonists and agonists of the invention.

BACKGROUND OF THE INVENTION

Identification and sequencing of human genes is a major goal of modem scientific research. For example, by identifying genes and determining their sequences, scientists have been able to make large quantities of valuable human gene products. These include human insulin, interferon, Factor VIII, human growth hormone, tissue plasminogen activator, erythropoeitin and numerous other proteins. Additionally, knowledge of gene sequences can provide keys to diagnosis, treatment or cure of genetic diseases such as muscular dystrophy and cystic fibrosis.

Despite the great progress that has been made in recent years, only a small number of genes which encode the presumably thousands of human proteins have been identified and sequenced. Therefore, there is a need for identification and characterization of novel human proteins and corresponding genes which can play a role in detecting, preventing, ameliorating or correcting disorders related to abnormal expression of and responses to such proteins.

SUMMARY OF THE INVENTION

The present invention provides isolated nucleic acid molecules comprising polynucleotide sequences which have been identified as sequences encoding human proteins of the invention. Each protein of the invention is identified in Table 1, below (see Example 2) by a reference number designated as a "Protein ID (Identifier)" (e.g., "PF353-01"). Each protein of the invention is related to a human complementary DNA (cDNA) clone prepared from a messenger RNA (MRNA) encoding the related protein. The cDNA clone related to each protein of the invention is identified by a "cDNA Clone ID (Identifier)" in Table 1 (e.g., "HABCE99"). DNA of each CDNA clone in Table 1 is contained in the material deposited with the American Type Culture Collection and given the ATCC Deposit Number shown for each cDNA Clone ID in Table 1, as further described below.

The invention provides a nucleotide sequence determined for an mRNA molecule encoding each protein identified in Table 1, which is designated in Table 1 as the "Total NT (Nucleotide) Sequence." This determined nucleotide sequence has been assigned a SEQ ID NO="X" in the Sequence Listing hereinbelow, where the value of X for the determined nucleotide sequence of each protein is an integer specified in Table 1. The determined nucleotide sequence provided for each protein of the invention was determined by applying conventional automated nucleotide sequencing methods to DNA of the corresponding deposited cDNA clone cited in Table 1.

The determined nucleotide sequence for the mRNA encoding each protein of the invention has been translated to provide a determined amino acid sequence for each protein which is identified in Table 1 by a SEQ ID NO="Y" where the value of Y for each protein is an integer defined in Table 1. The determined amino acid sequence for each protein represents the amino acid sequence encoded by the determined nucleotide sequence, beginning at or near the translation initiation ("start") codon of the protein and continuing until the first translation termination ("stop") codon. Due to possible errors inherent in determining nucleotide sequences from any DNA molecule, particularly using the conventional automated sequencing technology used to sequence the cDNA clones described herein, occasional nucleotide sequence errors are expected in the determined nucleotide sequences of the invention. These errors may include insertions or deletions of one or a few nucleotides in the determined nucleotide sequence as compared to the actual nucleotide sequence of the deposited cDNA. As one of ordinary skill would appreciate, incorrect insertions or deletions of one or two nucleotides into a determined nucleotide sequence leads to a shift in the translation reading frame compared to the reading frame actually encoded by a cDNA clone. Further, such a shift in frame within an actual open reading frame frequently leads to the appearance of a translation termination (stop) codon within the sequence encoding the polypeptide. Accordingly, due to occasional errors in the nucleotide sequences determined from the deposited cDNAs and any related DNA clones used to prepare the determined sequence for the mRNA encoding each secreted protein of the invention, the translations shown as determined amino acid sequences in SEQ ID NO:Y may represent only a portion of the complete amino acid sequence of the human secreted protein actually encoded by the mRNA represented by the corresponding cDNA clone in the ATCC deposit identified in Table 1. In any event, the determined amino acid sequence for each protein in Table 1, which is shown in SEQ ID NO:Y for each protein, comprises at least a portion of the amino acid sequence determined for that protein.

More particularly, the determined amino acid sequence is the amino acid sequence translated from the determined nucleotide sequence in the open reading frame of the first amino acid of the ORF to the last amino acid of that frame. In other words, the determined amino acid sequence is translated from the determined nucleotide sequence beginning at the codon having as its 5' end the nucleotide in the position of SEQ ID NO:X identified in Table 1 as the 5' nucleotide of the first amino acid (abbreviated in Table 1 as "5' NT of First AA"). Translation of the determined nucleotide sequence is continued in the reading frame of that first amino acid codon to the first stop codon in that same open reading frame, i.e., to the position in SEQ ID NO:X which encodes the amino acid at the position in SEQ ID NO:Y identified as the "last amino acid of the open reading frame" (abbreviated as "Last AA of ORF").

For any determined amino acid sequence in which the first amino acid is the methionine encoded by the translation initiation codon for the protein, Table 1 also identifies the position in SEQ ID NO:X of the 5' nucleotide of the start codon ("5' NT of Start Codon") as the same position in SEQ ID NO:X as that of the 5' nucleotide of the first amino acid ("First AA").

Table 1 also identifies the positions in SEQ ID NO:Y of the last amino acid of the signal peptide ("Last AA of Sig Pep") and the first amino acid of the secreted portion ("First AA of Secreted Portion") of the protein, for those polypeptide having a secretory leader sequence. The "secreted portion" of a secreted protein in the present context indicates that portion of the complete polypeptide translated from an mRNA which remains after cleavage of the signal peptide by a signal peptidase. In this context the term "mature" may also be used interchangeably with "secreted portion" although it is recognized that in other contexts "mature" may designate a portion of a "proprotein" which is produced by further cleavage of the polypeptide after cleavage of the signal peptide.

Accordingly, in one aspect the invention provides an isolated nucleic acid molecule comprising a nucleotide sequence which is identical to the nucleotide sequence of SEQ ID NO:X, where X is any integer as defined in Table 1. The invention also provides an isolated nucleic acid molecule comprising a nucleotide sequence which is identical to a portion of the nucleotide sequence of SEQ ID NO:X, for instance, a sequence of at least 50, 100 or 150 contiguous nucleotides in the nucleotide sequence of SEQ ID NO:X. Such a portion of the nucleotide sequence of SEQ ID NO:X may be described most generally as a sequence of at least C contiguous nucleotides in the nucleotide sequence of SEQ ID NO:X where: (1) the sequence of at least C contiguous nucleotides begins with the nucleotide at position N of SEQ ID NO:X and ends with the nucleotide at position M of SEQ ID NO:X; (2) C is any integer in the range beginning with a convenient primer size, for instance, about 20, to the total nucleotide sequence length ("Total NT Seq.") as set forth for SEQ ID NO:X in Table 1; (3) N is any integer in the range of 1 to the first position of the last C nucleotides in SEQ ID NO:X, or more particularly, N is equal to the value of Total NT Seq. minus the quantity C plus 1 (i.e., Total NT Seq.–(C+1)); and (4) M is any integer in the range of C to Total NT Seq.

Preferably, the sequence of contiguous nucleotides in the nucleotide sequence of SEQ ID NO:X is included in SEQ ID NO:X in the range of positions beginning with the nucleotide at about the 5' nucleotide of the clone sequence ("5' NT of Clone Seq." in Table 1) and ending with the nucleotide at about the 3' nucleotide of the clone sequence ("3' NT of Clone Seq." in Table 1). More preferably, the sequence of contiguous nucleotides is in the range of positions beginning with the nucleotide at about the position of the 5' Nucleotide of the Start Codon ("5' NT of Start Codon" in Table 1) and ending with the nucleotide at about the position of the 3' Nucleotide of the Clone Sequence as set forth for SEQ ID NO:X in Table 1. For instance, one preferred embodiment of this aspect of the invention is an isolated nucleic acid molecule which comprises a sequence at least 95%, 96%, 97%, 98%, or 99% identical to a sequence of about 500 contiguous nucleotides included in the nucleotide sequence of SEQ ID NO:X beginning at about the 5' NT of Start Codon position as set forth for SEQ ID NO:X in Table 1. Another preferred embodiment of this aspect of the invention is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Further embodiments of the invention include isolated nucleic acid molecules which comprise a nucleotide sequence at least 90% identical, and more preferably at least 95%, 96%, 97%, 98%, 99% or 99.9% identical, to any of the determined nucleotide sequences above. For instance, one such embodiment is an isolated nucleic acid molecule comprising a nucleotide sequence which is at least 95% identical to a sequence of at least 50 contiguous nucleotides in the nucleotide sequence of SEQ ID NO:X wherein X is any integer as defined in Table 1. Another embodiment of this aspect of the invention is an isolated nucleic acid molecule comprising a nucleotide sequence which is at least 95% identical to the complete nucleotide sequence of SEQ ID NO:X.

Isolated nucleic acid molecules which hybridize under stringent hybridization conditions to a nucleic acid molecule described above also are provided. Such a nucleic acid molecule which hybridizes does not hybridize under stringent hybridization conditions to a nucleic acid molecule having a nucleotide sequence consisting of only A residues or of only T residues.

The invention further provides a composition of matter comprising a nucleic acid molecule which comprises a human cDNA clone identified by a cDNA Clone ID (Identifier) in Table 1, which DNA molecule is contained in the material deposited with the American Type Culture Collection and given the ATCC Deposit Number shown in Table 1 for that cDNA clone. As described further in Example 1, this deposited material comprises a mixture of plasmid DNA molecules containing cloned cDNAs of the invention. Further, the invention provides an isolated nucleic acid molecule comprising a nucleotide sequence which is, for instance, at least 95% identical to a sequence of at least 50, 150 or 500 contiguous nucleotides in the nucleotide sequence encoded by a human cDNA clone contained in the deposit given the ATCC Deposit Number shown in Table 1. One preferred embodiment of this aspect is an isolated nucleic acid molecule comprising a nucleotide sequence which is at least 95% identical to the complete nucleotide sequence encoded by a human cDNA clone identified in Table 1 and as contained in the deposit with the ATCC Deposit Number shown in Table 1. Also provided are isolated nucleic acid molecules which hybridize under stringent hybridization conditions to a nucleic acid molecule comprising a nucleotide sequence encoded by a human cDNA clone identified in Table 1 and contained in the cited deposit.

These nucleic acid molecules of the invention may be used for a variety of identification and diagnostic purposes. For instance, the invention provides a method for detecting in a biological sample a nucleic acid molecule comprising a nucleotide sequence which is at least 95% identical to a sequence of at least 50 contiguous nucleotides in a nucleotide sequence of the invention. The sequence of the nucleic acid molecule used in this method is selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. This method of the invention comprises a step of comparing a nucleotide sequence of at least one nucleic acid molecule in the biological sample with a sequence selected from the group above, and determining whether the sequence of the nucleic acid molecule in the sample is at least 95% identical to the selected sequence. The step of comparing sequences may comprise determining the extent of nucleic acid hybridization between nucleic acid molecules in the sample and a nucleic acid molecule comprising the sequence selected from the above group. Alternatively, this step may be performed by comparing the nucleotide sequence determined from a nucleic acid molecule in the sample, for instance by automated DNA sequence methods, with the sequence selected from the above group.

In another aspect, the invention provides methods for identifying the species, tissue or cell type of a biological sample based on detecting nucleic acid molecules in the sample which comprise a nucleotide sequence of a nucleic acid molecule of the invention (for instance, a nucleic acid molecule comprising a nucleotide sequence that is at least 95% identical to at least a portion of a nucleotide sequence of SEQ ID NO:X or a nucleotide sequence encoded by a human cDNA clone identified in Table 1 as contained in the deposit with the ATCC Deposit Number shown therein. This method may be conducted by detecting a nucleotide sequence of an individual cDNA of the invention or using panel of nucleotide sequences of the invention. Thus, this method may comprise a step of detecting nucleic acid molecules comprising a nucleotide sequence in a panel of at least two nucleotide sequences, where at least one sequence in the panel is at least 95% identical to at least a portion of a nucleotide sequence of SEQ ID NO:X or a nucleotide sequence encoded by a human cDNA clone contained in the ATCC deposit. In this method for identifying the species, tissue or cell type of a biological sample, the detection of nucleic acid molecules comprising nucleotide sequences of the invention may be conducted by various techniques known in the art including, for instance, hybridization of either DNA or RNA probes to either DNA or RNA molecules obtained from the biological sample, as well as computational comparisons of nucleotide sequences determined from nucleic acids in a biological sample with nucleotide sequences of the invention.

Similarly, nucleic acid molecules of the invention may be used in a method for diagnosing in a subject a pathological condition associated with abnormal structure or expression of a gene encoding a protein identified in Table 1. This method may comprise a step of detecting in a biological sample obtained from the subject nucleic acid molecules comprising a nucleotide sequence that is at least 95% identical to at least a portion of a nucleotide sequence of SEQ ID NO:X or a nucleotide sequence encoded by a human cDNA clone identified in Table 1 as contained in the deposit with the given ATCC Deposit Number. Again, this diagnostic method may involve analysis of individual nucleotide sequences or panels of several nucleotide sequences, and the analysis of either DNA or RNA species using either DNA or RNA probes.

For use in identification or diagnostic methods such as those described above, therefore, the invention also provides a composition of matter comprising isolated nucleic acid molecules in which the nucleotide sequences of the nucleic acid molecules comprise a panel of sequences, at least one of which is at least 95% identical to a sequence, either a nucleotide sequence of SEQ ID NO:X or a nucleotide sequence encoded by a human cDNA clone contained in the ATCC deposit in Table 1. In this composition, the nucleic acid molecules may comprise DNA molecules or RNA molecules or both, as well as polynucleotide equivalents of DNA and RNA which are not naturally occurring but are known in the art as such.

Another aspect of the invention relates to polypeptides comprising amino acid sequences encoded by nucleotide sequences of the invention. For identification and diagnostic purposes, these polypeptides need not include the amino acid sequence of a complete secreted protein or even of the secreted form of such a protein, since, for instance, antibodies may bind specifically to a linear epitope of a polypeptide which comprises as few as 6 to 8 amino acids. Accordingly, the invention also provides an isolated polypeptide comprising an amino acid sequence at least 90%, preferably 95%, 96%, 97%, 98%, or 99% identical to a sequence of at least about 10, 30 or 100 contiguous amino acids in the amino acid sequence of SEQ ID NO:Y wherein Y is any integer as defined in Table 1. Preferably, the sequence of contiguous amino acids is included in the amino acid sequence of SEQ ID NO:Y beginning with the residue at about the position of the First Amino Acid of the Secreted Portion where one exists or the first amino acid of the open reading frame if the protein is not indicated as having a signal peptide and ending with the residue at about the Last Amino Acid of the Open Reading Frame as set forth for SEQ ID NO:Y in Table 1. A preferred embodiment of this aspect relates to an isolated polypeptide comprising an amino acid sequence at least 95% identical to the complete amino acid sequence of SEQ ID NO:Y.

As noted above, however, the determined amino acid sequence of SEQ ID NO:Y may not include the complete amino acid sequence of the protein encoded by each cDNA in the ATCC deposit identified in Table 1. Accordingly, the invention further provides an isolated polypeptide comprising an amino acid sequence at least 90% identical, preferably at least 95%, 96%, 97%, 98% or 99% identical to a sequence of at least about 10, 300 or 100 contiguous amino acids in the complete amino acid sequence of a secreted protein encoded by a human cDNA clone identified by a cDNA Clone Identifier in Table 1 and contained in the deposit with the ATCC Deposit Number shown for that cDNA clone in Table 1. A particularly preferred embodiment of this aspect is a polypeptide in which the sequence of contiguous amino acids is included in the amino acid sequence of a secreted ("mature") portion of the protein encoded by a human cDNA clone contained in the deposit, particularly a polypeptide comprising the entire amino acid sequence of the secreted portion of the secreted protein encoded by a human cDNA clone of the invention.

For purposes such as tissue identification and diagnosis of pathological conditions, the invention also provides an isolated antibody which binds specifically to a polypeptide comprising an amino acid sequence of the invention, (for instance, a sequence that is identical to a sequence of at least 6, preferably at least 7, 8, 9 or 10, contiguous amino acids in an amino acid sequence of SEQ ID NO:Y or in a complete amino acid sequence of a protein encoded by a human cDNA clone identified by a cDNA Clone Identifier in Table 1 and contained in the deposit cited therein. Further in the same vein, the invention provides a method for detecting in a biological sample a polypeptide comprising an amino acid sequence which is identical to a sequence of at least 6, preferably at least 7, 8, 9 or 10 contiguous amino acids in a sequence selected from the group consisting of an amino acid sequence of SEQ ID NO:Y and a complete amino acid sequence of a protein encoded by a human cDNA clone identified by a cDNA Clone Identifier in Table 1 and contained in the deposit with the ATCC Deposit Number shown for that cDNA clone in Table 1;. This method comprises a step of comparing an amino acid sequence of at least one polypeptide molecule in said sample with a sequence selected from the above group and determining whether the sequence of that polypeptide molecule in the sample is identical to the selected sequence of at least 6–10 contiguous amino acids. This step of comparing an amino acid sequence of at least one polypeptide molecule in the sample with a sequence selected from the above group may comprise determining the extent of specific binding of polypeptides in the sample to an antibody which binds specifically to a polypeptide comprising an amino acid sequence of the invention. Alternatively, this comparison step may be performed by comparing the amino acid sequence determined from a polypeptide molecule in the sample with the sequence selected from the above group, for instance, using computational methods.

The invention further provides methods for identifying the species, tissue or cell type of a biological sample comprising a step of detecting polypeptide molecules in the sample which include an amino acid sequence that is identical to a sequence of at least 6–10 contiguous amino acids an amino acid sequence of SEQ ID NO:Y or of a cDNA identified in Table 1 and contained in the cited deposit. This method may involve analyses of polypeptides for the presence of individual amino acid sequences of the invention or of panels of such sequences. Similarly provided are methods for diagnosing in a subject a pathological condition associated with abnormal structure or expression of a gene encoding a protein identified in Table 1. In preferred embodiments of these methods of the invention for identification or diagnosis, an antibody which binds specifically to a polypeptide comprising an amino acid sequence of the invention is used to analyze amino acid sequences of polypeptides in a biological sample.

In yet another aspect, the invention provides recombinant means for making a polypeptide comprising all or a portion of an amino acid sequence of the invention. For this purpose, an isolated nucleic acid molecule comprising a nucleotide sequence which is, for instance, at least 95% identical to a nucleotide sequence encoding a polypeptide which comprises an amino acid sequence of the invention (for instance, one that is at least 90% identical to SEQ ID NO:Y.

It will be readily appreciated by one of ordinary skill that, due to the degeneracy of the genetic code, any nucleotide sequence encoding the amino acid sequence of a given protein needs to share only a low level of identity with the nucleotide sequence of a human cDNA clone which encodes the identical amino acid sequence of that protein. It will be further appreciated that the nucleotide of the deposited cDNAs presumably all comprise codons optimized for expression by human cells from which the cDNAs originated. Therefore, for improved expression in recombinant prokaryotic host cells, for instance, it may be desirable to alter the codon usage in a nucleic acid molecule encoding an amino acid sequence of the invention, selecting codons in accordance with the redundancy of the genetic code, which provide optimal codon usage in the selected host. Preferred nucleic acid molecules of this aspect of the invention are those which encode a polypeptide which comprises an complete amino acid sequence of SEQ ID NO:Y or a complete amino acid sequence of a protein encoded by a human cDNA clone identified in Table 1 and contained in the deposit cited therein.

Using such nucleic acid molecules encoding polypeptides of the invention, the invention further provides recombinant means for making the polypeptides. Thus, included is a method of making a recombinant vector comprising inserting an isolated nucleic acid molecule of the invention into a vector, as well as a recombinant vector produced by this method. Also included is a method of making a recombinant host cell comprising introducing a vector of the invention into a host cell, and a recombinant host so made. Such cells are useful, for instance, in a method of making an isolated polypeptide of the invention which comprises culturing a recombinant host cell under conditions such that the polypeptide is expressed and recovering the polypeptide.

In a preferred embodiment of this method, the recombinant host cell is a eukaryotic cell and the polypeptide encoded by the nucleic acid of the invention encodes the complete amino acid sequence of a protein encoded by a cDNA identified in Table 1, so that the polypeptide produced by this method is a secreted ("mature") portion of a human secreted protein of the invention (i.e., one comprising an amino acid sequence of SEQ ID NO:Y beginning with the residue at the position identified in Table 1 as the First AA of Secreted Portion of SEQ ID NO:Y or an amino acid sequence of a secreted portion of a secreted protein encoded by a human cDNA clone identified in Table 1 and contained in the deposit with the ATCC Deposit Number shown in Table 1. The invention further provides an isolated polypeptide which is a secreted portion of a human secreted protein produced by the above method. Where the polypeptide shown in Table 1 does not have a leader sequence one may be provided by the vector. Such vectors are known in the art and are discussed below.

In yet another aspect, the invention provides a method of treatment of an individual in need of an increased level of a secreted protein activity. As described herein, diagnostic methods of the invention enable the identification of such individuals, that is, individuals with a pathological condition involving a particular organ, tissue or cell type, exhibiting lower levels of expression product (e.g., mRNA or antigen) of a given secreted protein in that organ, tissue or cell type, or those with mutant expression products, compared with normal individuals not suffering from the pathology. The method of the invention for treatment of an individual with such a pathological condition comprises administering to such an individual a pharmaceutical composition comprising an amount of an isolated polypeptide of a secreted protein of the invention effective to increase the level of activity of that secreted protein in the individual.

Agonists and antagonists of the polypeptides of the invention and methods for using these also are provided.

BRIEF DESCRIPTION OF THE DRAWINGS

FIGS. 1A–C show the nucleotide sequence and deduced amino acid sequence of CCV (HEMFI85), SEQ ID NOS:1 and 2, respectively.

FIGS. 2A–B show the nucleotide sequence and deduced amino acid sequence of CAT-1 (HTXET53), SEQ ID NOS:3 and 4, respectively.

FIGS. 3A–B show the nucleotide sequence and deduced amino acid sequence of CAT-2 (HT3SG28), SEQ ID NOS:5 and 6, respectively.

FIG. 4 shows the nucleotide sequence and deduced amino acid sequence of MIA-2 (HBXAK03), SEQ ID NOS:7 and 8, respectively.

FIGS. 5A–C show the nucleotide sequence and deduced amino acid sequence of MIA-3 (HLFBD44), SEQ ID NOS:9 and 10, respectively.

FIGS. 6A–B show the nucleotide sequence and deduced amino acid sequence of AIF-2 (HEBGM49), SEQ ID NOS:11 and 12, respectively.

FIGS. 7A–B show the nucleotide sequence and deduced amino acid sequence of AIF-3 (HNGBH45), SEQ ID NOS:13 and 14, respectively.

FIGS. 8A–C show the nucleotide sequence and deduced amino acid sequence of Annexin HSAAL25, SEQ ID NOS:15 and 16, respectively.

FIGS. 9A–K shows the nucleotide sequence and deduced amino acid sequence of ES/130-like I, SEQ ID NOS:17 and 18, respectively.

FIGS. 10A–F shows the nucleotide sequence and deduced amino acid sequence of BEF, SEQ ID NOS:19 and 20, respectively.

FIGS. 11A–E shows the nucleotide sequence and deduced amino acid sequence of ADF, SEQ ID NOS:21 and 22, respectively.

FIGS. 12A–D shows the nucleotide sequence and deduced amino acid sequence of Bcl-like, SEQ ID NOS:23 and 24, respectively.

DETAILED DESCRIPTION

Nucleic Acid Molecules

Nucleotide Sequences and ATCC Deposits of cDNA Clones Encoding Human Proteins The present invention provides isolated nucleic acid molecules comprising polynucleotide sequences which have been identified as sequences encoding human proteins. The invention further provides a nucleotide sequence determined from an mRNA molecule encoding each human protein identified in Table 1, which comprises all or a substantial portion of the complete nucleotide sequence of the mRNA encoding each protein of the invention and has been assigned a SEQ ID N="X" in the Sequence Listing and Figures hereinbelow, The term "isolated" means that the material is removed from its original environment (e.g., the natural environment if it is naturally occurring). For example, a naturally-occurring nucleic acid molecule or polynucleotide present in a living organism is not isolated, but the same nucleic acid molecule or polynucleotide, separated from some or all of the coexisting materials in the natural environment, is isolated. Such nucleic acid molecule could be part of a vector and/or such polynucleotide could be part of a composition, and still be isolated in that such vector or composition is not part of the natural environment of the nucleic acid molecule or polynucleotide.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as a nucleotide sequence shown in the sequence listing, a nucleic acid molecule of the present invention encoding a polypeptide may be obtained using standard cloning and screening procedures, such as those for cloning cDNAs using mRNA as starting material. The present invention provides not only the determined nucleotide sequences of the mRNA encoding each human secreted protein of the invention, as set forth in SEQ ID NO:X for each protein, but also a sample of plasmid DNA containing a cDNA of the invention deposited with the American Type Culture Collection (Rockville, Md.), as set forth in Table 1. These deposits enable recovery of each cDNA clone and recombinant production of each secreted protein of the invention actually encoded by a cDNA clone identified in Table 1, as further described hereinbelow.

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

In addition to nucleic acid molecules comprising a determined nucleotide sequence in SEQ ID NO:X or the nucleotide sequence of a deposited human cDNA clone, isolated nucleic acid molecules of the invention include DNA molecules which comprise a sequence substantially different from those described above but which, due to the degeneracy of the genetic code, still encode the proteins shown in the sequence listing or those encoded by the clones contained in the deposited plasmids. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*). Preferably, this nucleic acid molecule will encode a secreted portion (mature polypeptide) encoded by the deposited cDNA.

The invention further provides a nucleic acid molecule having a sequence complementary to one of the above sequences. Such isolated molecules, particularly DNA molecules, are useful as probes for gene mapping, by in situ hybridization with chromosomes, and for detecting expression of the corresponding gene(s) in human tissue, for instance, by Northern blot analysis.

The present invention is further directed to nucleic acid molecules encoding portions of the nucleotide sequences described herein as-well as to fragments of the isolated nucleic acid molecules described herein. By a "fragment" of an isolated nucleic acid molecule having the nucleotide sequence of the deposited cDNA or the nucleotide sequence shown in the sequence listing is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–500 nt in length are also useful according to the present invention as are fragments corresponding to most, if not all, of the nucleotide sequence of the deposited cDNA or as shown in the sequence listing. By a fragment "at least 20 nt in length," for example, is intended fragments which include 20 or more contiguous bases from the nucleotide sequence of the deposited cDNA or the determined nucleotide sequence shown in SEQ ID NO:X. Preferred nucleic acid fragments of the present invention include nucleic acid molecules encoding epitope-bearing portions of the polypeptides of the present invention, as described further below.

In another aspect, the invention provides an isolated nucleic acid molecule comprising a polynucleotide which hybridizes under stringent hybridization conditions to a portion of a nucleic acid molecule of the invention described above, for instance, a cDNA contained in the plasmid sample deposited with the ATCC. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below. For certain applications, such as the FISH technique for gene mapping on chromosomes, probes of 500 nucleotides up to 2000 nucleotides may be preferred.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:X). Of course, a polynucleotide which hybridizes only to a poly A sequence (such as any 3' terminal poly(A) tract of a cDNA shown in the sequence listing), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

Also encoded by nucleic acids of the invention are the amino acid sequences of the invention together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; and additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amine acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. USA*86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell*37: 767 (1984). As discussed below, other such fusion proteins include those fused to Fc at the N- or C-terminus.

Sequences Encoding Signal Peptide and Secreted Portions

According to the signal hypothesis, proteins secreted by eukaryotic cells have a signal peptide (or secretory leader sequence) which is cleaved from the complete polypeptide to produce a secreted portion or "mature" form of the protein. Methods for predicting whether a protein has a signal peptide (or "secretory leader") as well as the cleavage point for that leader sequence are well known in the art. See, for instance, von Heinje, supra. The determined amino acid sequence of several proteins of the invention, determined by translation of the determined nucleotide sequence identified in Table 1, have been found to comprise an amino acid sequence of a secretory signal peptide. The sequence and cleavage site of that signal peptide are described in Table 1 and in the Examples and the signal sequence is underlined in the Figures, to the extent that these have been determined for each secreted protein of the invention.

More in particular, the present invention provides nucleic acid molecules encoding a secreted portion (mature form) of each secreted protein identified in Table 1. Most mammalian cells and even insect cells cleave signal peptides from secreted proteins with approximately the same specificity. However, in some cases, cleavage of the signal peptide (as referred to herein as a "leader sequence" or "leader") from a secreted protein is not entirely uniform, which results in more than one secreted (also herein "mature") for or species of the protein. Further, it has long been known that the cleavage specificity of a secreted protein is ultimately determined by the primary structure of the complete protein, that is, it is inherent in the amino acid sequence of the initial polypeptide translated from its mRNA. Therefore, the present invention provides not only a determined nucleotide sequence and translated amino acid sequence identifying a signal peptide and secreted portion of each secreted protein of the invention, but also a deposited sample of a cDNA clone encoding a secreted (mature) form of each secreted protein of the invention.

More particularly, the invention further provides an isolated polypeptide comprising an amino acid sequence at least 90% identical, preferably 95%, 96%, 97%, 98% or 99% identical, to a sequence of at least about 25, 50 or 100 contiguous amino acids in the complete amino acid sequence of a protein encoded by a human cDNA clone identified by a cDNA Clone Identifier in Table 1 and contained in the deposit with the ATCC Deposit Number shown for that cDNA clone in Table 1. A particularly preferred embodiment of this aspect of the invention is a polypeptide in which the sequence of contiguous amino acids is included in the amino acid sequence of a secreted portion of a secreted protein encoded by a human cDNA clone identified by a cDNA Clone Identifier in Table 1 and contained in the deposit with the ATCC Deposit Number shown for said cDNA clone in Table 1. By the "secreted portion [or mature form] of a secreted protein encoded by a human cDNA clone identified by a cDNA Clone Identifier in Table 1 and contained in the deposit with the ATCC Deposit Number shown for said cDNA clone in Table 1" is meant the secreted portion(s) or mature form(s) of the protein produced by expression in any eukaryotic cell (for instance, cells of an established insect or mammalian cell line), preferably a human cell (for instance, cells of the well known HeLa cell line), of the complete open reading frame encoded by the human cDNA clone identified in Table 1 and contained in the deposit cited in Table 1.

Variant and Mutant Polynucleotides

The present invention further relates to variants of the nucleic acid molecules of the present invention, which encode portions, analogs or derivatives of the secreted proteins. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the secreted protein or portions thereof. Also especially preferred in this regard are conservative substitutions.

Most highly preferred are nucleic acid molecules encoding a secreted portion (mature form) of a protein described in Table 1 and having the amino acid sequence shown in the sequence listing as SEQ ID NO:X, or the amino acid sequence of the secreted portion (mature form) of the protein encoded by a deposited cDNA clone. Further embodiments include an isolated nucleic acid molecule comprising a polynucleotide having a nucleotide sequence at least 85% identical, more preferably at least 90% identical, and most preferably at least 95%, 96%, 97%, 98% or 99% identical to a polynucleotide of the invention described in Table 1, or a polynucleotide which hybridizes under stringent hybridization conditions to such a polynucleotide. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a secreted polypeptide having an amino acid sequence of SEQ ID NO:Y or an amino acid sequence of a secreted protein encoded by a cDNA clone in the deposit identified in Table 1.

By a polynucleotide having a nucleotide sequence at least, for example, 95% "identical" to a reference nucleotide sequence encoding a secreted polypeptide is intended that the nucleotide sequence of the polynucleotide is identical to the reference sequence except that the polynucleotide sequence may include up to five point mutations per each 100 nucleotides of the reference nucleotide sequence encoding the secreted polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 85%, 90%, 95%, 96%, 97%, 98% or 99% identical to, for instance, the nucleotide sequence shown in SEQ ID NO:1, or to the nucleotide sequence of a deposited cDNA can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Uses for Nucleic Acid Molecules of the Invention

Each of the nucleic acid molecules identified herein can be used in numerous ways as polynucleotide reagents. The polynucleotides can be used as diagnostic probes for the presence of a specific mRNA in a particular cell type. In addition, these polynucleotides can be used as diagnostic probes suitable for use in genetic linkage analysis (polymorphisms). Further, the polynucleotides can be used as probes for locating gene regions associated with genetic disease, as explained in more detail below.

The polynucleotides of the present invention are also valuable for chromosome identification. Each polynucleotide is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of cDNAs to chromosomes according to the present invention is an important first step in correlating those sequences with genes associated with disease.

Briefly, sequences can be mapped to chromosomes by preparing PCR primers (preferably 15–25 bp) from the sequences shown in the sequence listing. Computer analysis of the sequences is used to rapidly select primers that do not span more than one exon in the genomic DNA, thus complicating the amplification process. These primers are then used for All PCR screening of somatic cell hybrids containing individual human chromosomes. Only those hybrids containing the human gene corresponding to the secreted protein will yield an amplified fragment.

PCR mapping of somatic cell hybrids is a rapid procedure for assigning a particular nucleic acid sequence to a particular chromosome. Three or more clones can be assigned per day using a single thermal cycler. Using the present invention with the same oligonucleotide primers, sublocalization can be achieved with panels of fragments from specific chromosomes or pools of large genomic clones in an analogous manner. Other mapping strategies that can similarly be used to map a gene to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. For example, 2,000 bp is good, 4,000 is better, and more than 4,000 is probably not necessary to get good results a reasonable percentage of the time. For a review of this technique, see Verma et al., Human Chromosomes: a Manual of Basic Techniques. Pergamon Press, New York (1988).

Reagents for chromosome mapping can be used individually (to mark a single chromosome or a single site on that chromosome) or as panels of reagents (for marking multiple sites and/or multiple chromosomes). Reagents corresponding to noncoding regions of the genes actually are preferred for mapping purposes. Coding sequences are more likely to be conserved within gene families, thus increasing the chance of cross hybridizations during chromosomal mapping.

Once a polynucleotide sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library).) The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb.)

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

In addition to the foregoing, the polynucleotides of the invention, as broadly described, can be used to control gene expression through triple helix formation or antisense DNA or RNA, both of which methods are based on binding of a polynucleotide sequence to DNA or RNA. Polynucleotides suitable for use in these methods are usually 20 to 40 bases in length and are designed to be complementary to a region of the gene involved in transcription (triple helix—see Lee et al, Nucl. Acids Res., 6:3073 (1979); Cooney et al, Science, 241:456 (1988); and Dervan et al, Science, 251: 1360 (1991).) or to the mRNA itself (antisense—Okano, J. Neurochem., 56:560 (1991) Oligodeoxy-nucleotides as Antisense Inhibitors of Gene Expression, CRC Press, Boca Raton, Fla. (1988)). Triple helix formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

Nucleic acid molecules of the present invention are also a useful in gene therapy which requires isolation of the disease-associated gene in question as a prerequisite to the insertion of a normal gene into an organism to correct a genetic defect. The high specificity of the cDNA probes according to this invention offer means of targeting such gene locations in a highly accurate manner.

The sequences of the present invention, as broadly defined, are also useful for identification of individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The sequences of the present invention are useful as additional DNA markers for RFLP.

However, RFLP is a pattern based technique, which does not require the DNA sequence of the individual to be sequenced. The polynucleotides and sequences of the present invention can be used to provide an alternative technique that determines the actual base-by-base DNA sequence of selected portions of an individual's genome. These sequences can be used to prepare PCR primers for amplifying and isolating such selected DNA. One can, for example, take a sequence of the invention and prepare two PCR primers. These are used to amplify an individual's DNA, corresponding to the gene or gene fragment. The amplified DNA is sequenced.

Panels of corresponding DNA sequences from individuals, made this way, can provide unique individual identifications, as each individual will have a unique set of such DNA sequences, due to allelic differences. The sequences of the present invention can be used to particular advantage to obtain such identification sequences from individuals and from tissue, as further described in the Examples. The polynucleotide sequences shown in the sequence listing and the inserts contained in the deposited cDNAs uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences comprising a part of the present invention can, to some degree, be used as a standard against which DNA from an individual can be compared for identification purposes. Because greater numbers of polymorphisms occur in the noncoding regions, fewer sequences are necessary to differentiate individuals.

If a panel of reagents from sequences of this invention is used to generate a unique ID database for an individual, those same reagents can later be used to identify tissue from that individual. Positive identification of that individual, living or dead can be made from extremely small tissue samples.

Another use for DNA-based identification techniques is in forensic biology. PCR technology can be used to amplify DNA sequences taken from very small biological samples such as tissues, e.g., hair or skin, or body fluids, e.g., blood, saliva, semen, etc. In one prior art technique, gene sequences are amplified at specific loci known to contain a large number of allelic variations, for example the DQa class II HLA gene (Erlich, H., PCR Technology, Freeman and Co. (1992)). Once this specific area of the genome is amplified, it is digested with one or more restriction enzymes to yield an identifying set of bands on a Southern blot probed with DNA corresponding to the DQa class II HLA gene.

The sequences of the present invention can be used to provide polynucleotide reagents specifically targeted to additional loci in the human genome, and can enhance the reliability of DNA-based forensic identifications. Those sequences targeted to noncoding regions are particularly appropriate. As mentioned above, actual base sequence information can be used for identification as an accurate alternative to patterns formed by restriction enzyme generated fragments. Reagents for obtaining such sequence information are within the scope of the present invention. Such reagents can comprise complete genes, ESTs or corresponding coding regions, or fragments of either of at least 20 bp, preferably at least 50 bp, most preferably at least 500 to 1,000 bp.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

The present application is directed to nucleic acid molecules at least 85%, 90%, 95%, 96%, 97%, 98% or 99% identical to a nucleic acid sequence referenced in Table 1 and shown in the sequence listing or to the nucleic acid sequence of a deposited cDNA, irrespective of whether they encode a polypeptide having biological activity. This is because even where a particular nucleic acid molecule does not encode a polypeptide having biological activity, one of skill in the art would still know how to use the nucleic acid molecule, for instance, for one of the uses above.

Preferred, however, are nucleic acid molecules having sequences at least 85%, 90%, 95%, 96%, 97%, 98% or 99% identical to the nucleic acid sequence shown in FIGS. 1A–C (SEQ ID NO:1) or to the nucleic acid sequence of the deposited cDNA which do, in fact, encode a secreted polypeptide having biological activity. By "a polypeptide having biological activity" is intended polypeptides exhibiting activity similar, but not necessarily identical, to an activity of the mature protein of the invention, as measured in a particular biological assay. "A polypeptide having biological activity" includes polypeptides that also exhibit any of the same activities as a protein of the invention in an assay in a dose-dependent manner. Although the degree of dose-dependent activity need not be identical to that of the protein, preferably, "a polypeptide having biological activity" will exhibit substantially similar dose-dependence in a given activity as compared to the protein (i.e., the candidate polypeptide will exhibit greater activity or not more than about 25-fold less and, preferably, not more than about tenfold less activity relative to the reference protein).

Of course, due to the degeneracy of the genetic code, one of ordinary skill in the art will immediately recognize that a large number of the nucleic acid molecules having a sequence at least 85%, 90%, 95%, 96%, 97%, 98%, or 99% identical to the nucleic acid sequence of the deposited cDNA or the nucleic acid sequence shown in the sequence listing will encode a polypeptide "having biological activity." In fact, since degenerate variants of these nucleotide sequences all encode the same polypeptide, this will be clear to the skilled artisan even without performing the comparison assay. It will be further recognized in the art that, for such nucleic acid molecules that are not degenerate variants, a reasonable number will also encode a polypeptide having biological activity. This is because the skilled artisan is fully aware of amino acid substitutions that are either less likely or not likely to significantly affect protein function (e.g., replacing one aliphatic amino acid with a second aliphatic amino acid), as further described below.

Vectors, Host Cells and Protein Production

The present invention also relates to vectors which include the isolated DNA molecules of the present invention, host cells which are genetically engineered with the recombinant vectors, and the production of polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G4 18 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc., supra; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., *J. Molecular Recognition* 8:52–58 (1995) and K. Johanson et al., *J. Biol. Chem.* 270:9459–9471 (1995).

A protein of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Polypeptides and Fragments

The invention further provides isolated polypeptides having an amino acid sequence encoded by a deposited cDNA, or an amino acid sequence in the sequence listing identified SEQ ID NO:Y as defined in Table 1, or a peptide or polypeptide comprising a portion of the above polypeptides. At the simplest level, the amino acid sequence can be synthesized using commercially available peptide synthesizers. This is particularly useful in producing small peptides and fragments of larger polypeptides. Such fragments are useful, for example, in generating antibodies against the native polypeptide.

Variant and Mutant Polypeptides

To improve or alter the characteristics of the polypeptides of the invention, protein engineering may be employed. Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

For instance, for many proteins, including the mature form(s) of a secreted protein, it is known in the art that one or more amino acids may be deleted from the N-terminus or C-terminus without substantial loss of biological function. For instance, Ron et al., *J. Biol. Chem.*, 268:2984–2988 (1993) reported modified KGF proteins that had heparin binding activity even if 3, 8, or 27 amino-terminal amino acid residues were missing. Similarly, many examples of biologically functional C-terminal deletion muteins are known. For instance, Interferon gamma shows up to ten times higher activities by deleting 8–10 amino acid residues from the carboxy terminus of the protein (Dobeli et al., *J. Biotechnology* 7:199–216 (1988). Furthermore, even if deletion of one or more amino acids from the N-terminus or C-terminus of a protein results in modification or loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature form of the protein are removed from the N-terminus or C-terminus. Whether a particular polypeptide lacking N- or C-terminal residues of a complete protein retains such immunologic activities can readily be determined by routine methods described herein and otherwise known in the art.

In addition to terminal deletion forms of the protein discussed above, it also will be recognized by one of ordinary skill in the art that some amino acid sequences of a polypeptide can be varied without significant effect of the structure or function of the protein. If such differences in sequence are contemplated, it should be remembered that there will be critical areas on the protein which determine activity.

Thus, the invention further includes variants of a polypeptide which show substantial biological activity or which include regions of the protein such as the portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of a polypeptide shown in the figures (and sequence listing), or one encoded by the deposited CDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein Thus, the mature polypeptide of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 2).

TABLE 2

| CONSERVATIVE AMINO ACID SUBSTITUTIONS | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331–340 (1967); Robbins et al., Diabetes 36: 838–845 (1987); Cleland et al., *Crit. Rev. Therapeutic Drug Carrier Systems* 10:307–377 (1993).

Replacement of amino acids can also change the selectivity of the binding of a ligand to cell surface receptors. For example, Ostade et al., *Nature* 361:266–268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form, and preferably are substantially purified. A recombinantly produced version of a polypeptide of the invention can be substantially purified by the one-step method described in Smith and Johnson, *Gene* 67:31–40 (1988). Polypeptides of the invention also can be purified from natural or recombinant sources using antibodies of the invention raised against the protein in methods which are well known in the art of protein purification.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to a polypeptide encoded by a deposited cDNA or to the polypeptide of SEQ ID NO:Y, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a polypeptide described herein is intended that the amino acid sequence of the polypeptide is identical to the reference sequence except that the polypeptide sequence may include up to five amino acid alterations per each 100 amino acids of the reference amino acid of the polypeptide of the invention. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, an amino acid sequence shown in the sequence listing or to an amino acid sequence encoded by the deposited cDNA can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting the corresponding protein expression as described below or as agonists and antagonists capable of enhancing or inhibiting function of the protein. Further, such polypeptides can be used in the yeast two-hybrid system to "capture" receptors of secreted proteins which are also candidate agonists and antagonists according to the present invention. The yeast two hybrid system is described in Fields and Song, Nature 340:245–246 (1989).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins," *Science*, 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention.

The epitope-bearing peptides and polypeptides of the invention may be produced by any conventional means. See, e.g., Houghten, R. A. (1985) "General method for the rapid solid-phase synthesis of large numbers of peptides: specificity of antigen-antibody interaction at the level of individual amino acids." *Proc. Natl. Acad. Sci. USA* 82:5131–5135; this "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol*, 66:2347–2354 (1985). Immunogenic epitope-bearing peptides of the invention, i.e., those parts of a protein that elicit an antibody response when the whole protein is the immunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1-C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric secreted protein or protein fragment alone (Fountoulakis et al., *J. Biochem.* 270:3958–3964 (1995)).

Antibodies

Protein-species specific antibodies for use in the present invention can be raised against an intact protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the protein of the present invention or an antigenic fragment thereof can be administered to an animal in order to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology (köhler et al., *Nature* 256:495 (1975); köhler et al., *Eur. J. Immunol.* 6:511 (1976); köhler et al., *Eur. J. Immunol.* 6:292 (1976); Hammerling et al., in: *Monoclonal Antibodies and T-Cell Hybridomas*, Elsevier, N.Y., (1981) pp. 563–681). In general, such procedures involve immunizing an animal (preferably a mouse) with a protein antigen of the invention or, more preferably, with a protein-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 $\mu$/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the American Type Culture Collection, Rockville, Maryland. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the protein antigen.

Alternatively, additional antibodies capable of binding to the protein antigen of the invention may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the protein antigen. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Identification and Diagnostic Applications

Assaying protein levels in a biological sample can occur using antibody-based techniques. For example, protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

In addition to assaying protein levels in a biological sample obtained from an individual, protein can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, $^{131}I$, $^{112}In$, $^{99m}Tc$), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Treatment of Conditions Related to Proteins of the Invention

It will be appreciated that conditions caused by a decrease in the standard or normal expression level of a protein of the invention, particularly a secreted protein, in an individual can be treated by administration of the polypeptide (in the form of a mature protein for secreted polypeptides). Thus, the invention also provides a method of treatment of an individual in need of an increased level of the protein of the present invention comprising administering to such an individual a pharmaceutical composition comprising an amount of the isolated polypeptide of the invention effective to increase the activity level of the protein in such an individual.

Formulations

Polypeptide composition will be formulated and dosed in a fashion consistent with good medical practice, taking into account the clinical condition of the individual patient (especially the side effects of treatment with the polypeptide alone), the site of delivery, the method of administration, the scheduling of administration, and other factors known to practitioners. The "effective amount" for purposes herein is thus determined by such considerations.

As a general proposition, the total pharmaceutically effective amount of a polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the protein of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

The polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988). Sustained-release compositions also include liposomally entrapped polypeptides. Liposomes containing the polypeptide are prepared by methods known per se: DE 3,218,121; Epstein et al., *Proc. Natl. Acad. Sci. (USA)* 82:3688–3692 (1985); Hwang et al., *Proc. Natl. Acad. Sci. (USA)* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal polypeptide therapy.

For parenteral administration, in one embodiment, the polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration must be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized. formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Having generally described the invention, the same will be more readily understood by reference to the following examples, which are provided by way of illustration and are not intended as limiting.

EXAMPLES

Example 1

Isolation of A Selected CDNA Clone From the Deposited Sample

Each protein of the invention is related to a human complementary DNA (cDNA) clone prepared from a messenger RNA (MRNA) encoding the related protein. The cDNA clone related to each protein of the invention is identified by a "cDNA Clone ID (Identifier)" in Table 1, below (e.g., "HABCE99"). DNA of each cDNA clone in Table 1 is contained in the material deposited with the American Type Culture Collection and given the ATCC Deposit Number shown for each cDNA Clone ID in Table 1. All deposits containing such clones have been submitted to the American Type Culture Collection (10801 University Blvd, Mannasas, Va. 20110–2209) on the date indicated for each given accession number indicated in Table 1. All deposits have been made in accordance with the Budapest Treaty, and in full compliance with 37 CFR §1.801 et seq.

The cDNA clones contained in the ATCC deposits cited in Table 1 can be utilized by those of skill in the art by reference to the information describing each clone, and by reference to SEQ ID NO:X, provided in Table 1 for the determined nucleotide sequence of each deposited clone. The following additional information is provided for convenience. Each cDNA clone in a cited ATCC deposit is contained in a plasmid vector. Table 1 identifies the vector used to construct the cDNA library from which each clone was isolated. In many cases the vector used to construct the library is a phage vector from which a plasmid has been excised. The table immediately below provides a correlation of the related plasmid for each such phage vector used in construction of the cDNA library from which each cDNA clone listed in Table 1 originally was isolated. For example, where a particular clone is identified in Table 1 as being isolated in the vector "Lambda Zap," it can be seen from the following table that this cDNA clone contained in the biological deposit in pBluescript.

| Vector Used to Construct Library | Corresponding Deposited Plasmid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ®2.1 | pCR ®2.1 |

Vectors Lambda Zap (U.S. Pat. Nos. 5,128,256 and 5,286,636), Uni-Zap XR (U.S. Pat. Nos. 5,128, 256 and 5,286,636), Zap Express (U.S. Pat. Nos. 5,128,256 and 5,286,636), pBluescript (pBS) (Short, J. M. et al., *Nucleic Acids Res.* 16:7583–7600 (1988); Alting-Mees, M. A. and Short, J. M., *Nucleic Acids Res.* 17:9494 (1989)) and pBK (Alting-Mees, M. A. et al., *Strategies* 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both may be transformed into *E. coli* strain XL-1 Blue, also available from Stratagene. pBS comes in 4 forms SK+, SK−, KS+and KS−. The S and K refer to the orientation of the polylinker to the T7 and T3 primer sequences which flank the polylinker region ("S" is for SacI and "K" is for KpnI which are the first restriction enzyme sites on each respective end of the linker). "+" or "−" refer to the orientation of the f1 origin of replication ("ori"), such that in one orientation single stranded rescue initiated from the f1 ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into *E. coli* strain DH10B, also available from Life Technologies. See, for instance, Gruber, C. E., et al., *Focus* 15:59- (1993). Vector lafmid BA (Bento Soares, Columbia University, N.Y.) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from Life Technologies. See, for instance, Clark, J. M., *Nuc. Acids Res.* 16.9677–9686 (1988) and Mead, D. et al., *Bio/Technology* 9: (1991).

The deposited material in the sample assigned the ATCC Deposit Number cited in Table 1 for any given cDNA clone also may contain one or more additional plasmids, each comprising a cDNA clone different from that given clone. Thus, each cited deposit contains at least a plasmid for each cDNA clone identified in Table 1 as sharing the same ATCC Deposit Number.

Two approaches are used herein to isolate a particular clone from the deposited sample of plasmid DNAs cited for that clone in Table 1, although others are known in art. In the first, a plasmid is isolated directly by screening clones using an oligonucleotide probe. To isolate a particular clone, a specific oligonucleotide with 30–40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods (e.g., Maniatis et al., Molecular Cloning: A Laboratory Manual, Cold Spring Harbor Press, Cold Spring, N.Y., 1982). The plasmid mixture is transformed into a suitable host, as indicated above (such as XL-1 Blue (Stratagene)) using techniques known to those of skill in the art such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other technique known to those of skill in the art.

An alternative approach to isolate any polynucleotide of interest in the deposited library is to prepare two oligonucleotide primers of 17–20 nucleotides derived from both ends of the determined sequence for the selected clone (i.e., within the region of SEQ ID NO:X bounded by the 5' NT of the clone and the 3' NT of the clone defined in Table 1 for each cDNA clone identified therein. These two oligonucleotide primers are used to amplify the polynucleotide of interest using the deposited cDNA plasmid as a template. The polymerase chain reaction is carried out under routine conditions, for instance, in 25 μl of reaction mixture with 0.5 μg of the above cDNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to filter probing, clone enrichment using specific probes and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res., 21(7):1683–1684 (1993). Briefly, a specific RNA oligonucleotide is ligated to the 5' ends of a population of RNA presumably containing full-length gene RNA transcript and a primer set containing a primer specific to the ligated RNA oligonucleotide and a primer specific to a known sequence of the gene of interest, is used to PCR amplify the 5' portion of the desired full-length gene which may then be sequenced and used to generate the full length gene. This method starts with total RNA isolated from the desired source; poly A RNA may be used but is not a prerequisite for this procedure. The RNA preparation may then be treated with phosphatase if necessary to eliminate 5' phosphate groups on degraded or damaged RNA which may interfere with the later RN-A ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis-reaction can then be used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Features of Proteins of the Invention

Table 1, below, describes particular features of the proteins and related nucleotide and amino acid sequences of this invention.

TABLE 1

FEATURES OF PROTEINS OF THE INVENTION

| Protein ID (Group-Nr) | cDNA Clone ID | ATCC Deposit Nr and Date | Vector | NT SEQ ID NO: X | Total NT Seq. | 5' NT of Clone Seq. | 3' NT of Clone Seq. | NOTE | 5' NT of Start Codon | 5' NT of First AA | AA SEQ ID NO: Y | First AA | Last AA of Sig Pep | First AA of Secreted Portion | Last AA of ORF |
|---|---|---|---|---|---|---|---|---|---|---|---|---|---|---|---|
| PF353-1 | HEMFI85 | 209053 05/16/97 | pBluescript SK- | 1 | 1093 | 1 | 1093 | | 119 | 119 | 2 | 1 | | | 103 |
| PF353-2 | HTXET53 | 209053 05/16/97 | pBluescript SK- | 3 | 887 | 1 | 887 | | 64 | 64 | 4 | 1 | 15 | 16 | 172 |
| PF353-3 | HT3SG28 | 209053 05/16/97 | pBluescript SK- | 5 | 540 | 1 | 540 | | 19 | 19 | 6 | 1 | 22 | 23 | 88 |
| PF353-4 | HBZAK03 | 209053 05/16/97 | pSport 1.0 | 7 | 520 | 1 | 520 | | 112 | 112 | 8 | 1 | | | 59 |
| PF353-5 | HDFUB43 | 209053 05/16/97 | pBluescript SK- | 9 | 1352 | 1 | 1352 | | 55 | 55 | 10 | 1 | | | 116 |
| PF353-6 | HEBGM49 | 209054 05/16/97 | pBlue script SK- | 11 | 632 | 1 | 632 | | 88 | 88 | 12 | 1 | | | 150 |
| PF353-7 | HNGBH54 | 209054 05/16/97 | Uni-ZAP XR | 13 | 582 | 1 | 582 | | 1 | 1 | 14 | 1 | | | 193 |
| PF353-8 | HSAAL25 | 209054 05/16/97 | pBluescript SK- | 15 | 1356 | 1 | 1356 | | 115 | 115 | 16 | 1 | | | 324 |
| PF353-9 | HUSAX55 | 209054 05/16/97 | pBluescript SK- | 17 | 2934 | 1 | 2934 | | 1 | 1 | 18 | 1 | | | 977 |
| PF353-10 | HSXCK41 | 209054 05/16/97 | pBluescript SK- | 19 | 1587 | 1 | 1587 | | 1 | 1 | 20 | 1 | 15 | 16 | 528 |
| PF353-11 | HFKFY79 | 209054 05/16/97 | pBluescript SK- | 21 | 1359 | 1 | 1359 | | 1 | 1 | 22 | 1 | | | 452 |
| PF353-12 | HAICH28 | 209054 05/16/97 | Uni-Zap XR | 23 | 1098 | 1 | 1098 | | 1 | 1 | 24 | 1 | | | 365 |

FEATURES OF THE PROTEIN ENCODED BY SEQ ID NO: 1

The novel full-length chemotactic cytokine V (CCV) polypeptide exhibits significant sequence identity to a chemotactic protein isolated from the murine S100 fraction designated CP-10 (chemotactic protein, 10 kD). The chemotactic cytokine V cDNA clone contains an 1091 nucleotide insert (SEQ ID NO:1) which encodes a 103 amino acid polypeptide (SEQ ID NO:2), both shown in FIGS. 1A–C. The clone was obtained from an induced endothelial cell cDNA library. A sequence alignment analysis of the deduced amino acid sequence of HEMFI85 shows that CCV shares approximately 24% identity and 69% similarity to the amino acid sequence of the murine CP-10 protein. In addition, it was determined by a BLAST analysis that the amino acid sequence of chemotactic cytokine V also exhibits approximately 31% identity and 67% similarity to the previously described rat intracellular Ca2+-binding protein. An examination of expression of chemotactic cytokine V in the HGS database reveals a widespread cell and tissue distribution of this gene. Expression of this clone was observed in a wide variety of human cDNA libraries in the Human Genome Sciences, Inc. (HGS) express sequence tag (EST) database including colon carcinoma (HCC) cell line, smooth muscle, amygdala depression, keratinocytes, uninduced endothelial cells, osteoblasts, and others.

CP-10 is a potent factor capable of extravascular recruitment of polymorphonuclear cells (PMN) and monocytes from circulation. Optimal chemotactic activity of CP-10 for murine PMN and neutrophils is in the range of 10–11 and 10–13 M, making this factor one of the most potent chemotactic factors reported to date. CP-10 is the murine homologue of a human S100 protein designated migration inhibition factor-related protein 8 (MRP8). MRP 8 can occur as a complex with an additional human S100 protein termed MRP14 (the complex has previously been reported as the cystic fibrosis antigen, calgranulin A and B, or LI antigen). This complex can comprise as much as 10–20% of the total cytoplasmic protein content of resting neutrophils and, although a significantly lower percentage of total cytoplasmic protein content, MRP8/14 complexes can also be found in resting monocytes. There is also evidence that suggests that MRP8/14 may be released from myeloid cells, although it is not clear whether the complex is actively released as part of a response to inflammation or passively as a part of the demise of such cells during the inflammatory process.

The function(s) of MRP8/14 complexes, CP-10, and related S100 fraction Ca2+-binding proteins are not entirely clear. However, it is thought that a major functional role of such proteins is in the recruitment of certain populations of immune cells to areas of inflammation. Devery and coworkers (J. Immunol. 152, 1888–1897; 1994) have demonstrated that expression of cell surface molecules such as Mac-1, which is involved in the process of cell adhesion as well as several additional cellular processes, may be influenced by prior interaction of the cell with chemotactic factors such as CP-10. These studies have also been performed in vivo where it was observed that CP-10 protein accumulated on the endothelial lining of small blood vessels in LPS-inflamed footpads. Furthermore, increased levels of MRP8/14 have been observed in the sera of patients afflicted with several inflammatory diseases including rheumatoid arthritis. It has also been suggested that chemotactic cytokine molecules such as CP-10 or MRP8/14 may function as a type of "calcium sink" during times of elevated intracellular levels of calcium for sustained periods of time. Alternatively, it has been suggested that MRP8/14 may function as a specific inhibitor of casein kinase II activity. Although the precise functional role(s) of many of the currently defined chemotactic cytokine-like proteins containing significant regions of sequence identity to HEMFI85 are not known in any detail, a number of studies with these proteins strongly suggest one or more roles for these proteins in a variety of human disease states including rheumatoid arthritis, sarcoidosis, tuberculosis, onchocerciasis, and other chronic inflammatory disease states. As a result, the discovery of a novel chemotactic cytokine-like molecule is believed to be of value in a variety a therapeutic and diagnostic capacities.

Owing to the homology to CP-10 and other calcium binding proteins it is expected that the CCV polypeptide shares common bioactivities. The activity of CCV may be assayed by any of several biological assays known in the art, preferably calcium binding assays. The homology to CP-10 and other calcium binding proteins indicates that the CCV polypeptide is useful in the detection and treatment of chronic inflammatory diseases such as rheumatoid arthritis, sarcoidosis, tuberculosis and onchocerciasis.

FEATURES OF THE PROTEINS ENCODED BY SEQ ID NOS: 3 and 5

The full-length nucleotide sequences of two novel human cDNA clones (HTXET53 and HT3SG28) which encode splice variants of the previously reported and highly related chemokines LAG-2, NKG5, and 519 have recently been identified. See for example, Hercend and Triebel (WPI Acc. No. 90–132241/17). These two clones have been designated Chemokine from Activated T-Cells-1 (CAT-1) (HTXET53), and Chemokine from Activated T-Cells-2 (CAT-2) (HT3SG28).

The HTXET53 clone was obtained from a human activated (12 hour) T-cell cDNA library and contains a 887 nucleotide insert (SEQ ID NO:3) which encodes a 172 amino acid polypeptide (SEQ ID NO:4), shown in FIGS. 2A–B. The HT3SG28 clone was obtained from a human activated (8 hour) T-cell cDNA library and contains a 550 nucleotide insert (SEQ ID NO:5) which encodes an 88 amino acid polypeptide (SEQ ID NO:6), shown in FIGS. 3A–B. The predicted amino acid sequences of the novel full-length CAT splice variants contain several regions of nearly perfect sequence identity to the previously reported human LAG-2, NKG5, and 519 lymphokines. Alignment of the amino acid sequences shows perfect identity between the two novel molecules with LAG-2 and NKG5, with the exception of a 27 amino acid insertion near the amino terminus of HTXET53, and a 57 amino acid deletion very near the carboxy terminus of HT3SG28. The 519 amino acid sequence differs from each of the novel clones and from LAG-2 and NKG5 by an 18 amino acid deletion of the hydrophobic amino terminus.

The HTXET53 polypeptide is predicted to have a 15 amino acid secretory leader sequence. The HT3SG28 polypeptide is predicted by the computer program PSORT to have either a 15 or a 22 amino acid leader sequence. The leader sequences are underlined in FIGS. 2A–B and 3A–B. Applicants believe that both the shorter and longer form of the HT3SG28 polypeptides (i.e., beginning at either residue 16 or residue 23) are active.

Expression profiles of the two novel genes are qualitatively identical in the HGS database. Additional HGS human cDNA libraries which contain the two novel CAT clones are resting T-cells, apoptotic T-cells, activated T-cells, spleen (chronic lymphocytic leukemia), activated monocytes, pituitary, and 9 week early stage human. The mRNA expression patterns of these novel genes have not been examined by Northern blot analysis.

The original molecule cloned from this group the T-cell-specific clone 519. NKG5 was a term used to describe a group of identical clones isolated from a human natural killer (NK) cell cDNA library. These genes are highly related and are thought to be expressed only in NK and T-cells. A genomic clone of the gene which encodes both 519 and NKG5 consists of at least five exons and four introns which are likely responsible for the generation of the related, but unique gene products. The genomic clone also reveals a number of T-cell-specific and activation state-specific regulatory sequences indicating that expession of the gene is highly restricted to certain functions of a small subset of cell types.

The novel and previously described molecules discussed herein also contain approximately 33% identity with a recently reported clone designated NK-lysin. NK-lysin has been found to exhibit a potent anti-bacterial activity against such organisms as *Escherichia coli, Bacillus megaterium, Acinetobacter calcoaceticus,* and *Streptococcus pyogenes.* In addition, NK-lysin was also observed to possess a marked lytic activity against an NK-cell-sensitive mouse tumor cell line (YAC-1), but had no such activity against erythrocytes. As a result, there are a number of potential therapeutic and/or diagnostic applications for a factor such as those encoded by HTXET53 and HT3SG28. Applications may include the detection and treatment of such clinical presentations as various bacterial infections, a number of lymphomas, immunological disorders, autoimmune diseases, inflammatory diseases, various allergies, and possibly as anti-infectious agents.

FEATURES OF THE PROTEINS ENCODED BY SEQ ID NOS: 7 and 9

The novel Melanoma Inhibitory Activity Protein (MIA)-2 and -3 cDNA clones presented herein are shown in FIGS. 4 and 5A–C. The cDNA clone HBZAK03 contains a 520 nucleotide insert (SEQ ID NO:7) which encodes a 59 amino acid polypeptide (SEQ ID NO:8), as shown in FIG. 4. A BLAST analysis of the predicted amino acid sequence of HBZAK03 demonstrates that this novel clone appears to be a splice variant of another cDNA clone designated HLFBD44. The nucleotide sequence of HLFBD44 (SEQ ID NO:9) and deduced amino acid sequence (SEQ ID NO:10) are shown in FIGS. 5A–C. Both of these HGS clones exhibit significant sequence identity to a human gene termed melanoma inhibitory activity (MIA) protein. BestFit analysis demonstrates that the HBZAK03 protein exhibits approximately 20% identity and 58% similarity to the MIA protein over a region of roughly 60 amino acids. The expression profile of the HBZAK03 cDNA in the HGS database reveals that it appears in a number of HGS human cDNA libraries in addition to the prostate cDNA library from which it was cloned. Some of the cDNA libraries in which this clone appears include fetal lung, the bone marrow cell line (RS4;11), macrophage, serum-treated smooth muscle, epileptic frontal cortex, subtracted fetal brain, HSA 172 cell line, induced endothelial cells, and others.

The highest sequence identity of the novel cDNA clones presented herein suggests that they may possess a function involved in the regulation of melanoma progression. The previously described MIA protein functions as a component of a highly complex and only partially characterized system of stimulatory and inhibitory factors which together dictate the progression of a melanoma. MIA is secreted by malignant melanoma cells and has the capacity to inhibit the growth of melanoma cells in culture. Investigators have examined the expression profile of the MIA gene by Northern blot and RT-PCR analysis and have determined that it is expressed in all melanoma cell lines, a few glioma cell lines, approximately half of the benign melanomas, all malignant melanomas, and from all lymph node metastases of malignant melanomas examined (Bosserhoff et al., J. Biol Chem. 271, 490–495; 1996). In contrast, no sMA expression was detected by these methods in samples obtained from any other skin-derived cells including normal fibroblasts, HaCaT keratinocytes, COS cells, HeLa cells, HepG2 cells, DU 145 (human prostate carcinoma) cells, and J82 (human bladder carcinoma) cells.

Based on the sequence similarity between these polypeptides MIA-2 and -3 are predicted to be useful in the detection and regulation of malignant melanoma, in immune system modulation, and in the treatment of cardiac arrest and stroke. Other activities of MIA-1 as well as assays for detecting MIA-1 activity are outlined in WO 95/03328, hereby incorporated herein by reference in its entirety. MIA-2 and -3 activity can be assayed accordingly.

FEATURES OF THE PROTEINS ENCODED BY SEQ ID NOS: 11 and 13

A macrophage-specific protein, termed AIF-1, has only very recently been molecularly cloned. AIF-1 appears to function in macrophage activation in the pathogenesis of chronic cardiac rejection following transplantation. A characteristic manifestation of cardiac tissue rejection following transplantation is an immune-mediated arteriosclerosis which ultimately results in graft failure and creates the need for retransplantation during the first postoperative year. It is thought that the arteriosclerotic state results from an alloimmune response involving activated immune cells, particularly macrophages, which stimulate smooth muscle-cell migration and proliferation into the area of the transplant leading to lesions in donor vessels. AIF-1 was identified by Utans and coworkers (J. Clin. Invest. 95, 2954–2962; 1995) in ongoing studies of inducible gene expression patterns in macrophage cells in a chronic rejecting rat heart allograft model. AIF-1 was expressed in response to INF-g in the chronic cardiac rejection model referenced above. Expression of AIF-1 was seen selectively in activated macrophages, neutrophils, and the macrophage-like cell lines THP-1, U937, and HL60, but not in several other human cells and tissues examined. Furthermore, low levels of AIF-1 expression can be observed in endomyocardial biopsy samples obtained from human heart transplant patients.

The cDNA clone designated HEBGM49 or "AIF-2" contains a 632 nucleotide cDNA insert (SEQ ID NO:11) encoding a 150 amino acid polypeptide (SEQ ID NO:12), as shown in FIGS. 6A–B. The cDNA clone was isolated from a human early stage brain cDNA library. This clone also appears in several other cDNA libraries constructed from a variety of human cell and tissue types including fetal epithelium, fetal kidney, hippocampus, tongue, and osteoblastoma HOS cells. A BLAST analysis of the amino acid sequence of HEBGM49 demonstrated that this clone exhibits approximately 65% identity and 80% similarity with AIF-1 over its entire length.

The cDNA clone HNGBH45 or "AIF-3" contains a 757 nucleotide cDNA insert (SEQ ID NO:13) encoding a 193 amino acid polypeptide (SEQ ID NO:14), as shown in FIGS. 7A–B. The cDNA clone was isolated from a human neutrophil cDNA library. This clone appears in a number of additional cDNA libraries including aortic endothelium, cerebellum, corpus collosum, CD34-depleted buffy coat, activated neutrophil, colon cancer, resting T-cells, tonsils, and others. A BLAST analysis of the amino acid sequence of HNGBH45 demonstrated that this clone exhibits approximately 25% identity and 47% similarity over approximately 70 amino acids of the AIF-1 molecule.

AIF-2 and AIF-3 are believed to be valuable clinical markers for assessing 25 varying degrees of acute and chronic rejection of transplanted cardiac tissue. In addition, monitoring the level of AIF-2 and/or AIF-3 expression may also be useful in determining the level of macrophage or neutrophil infiltration into area of the transplanted tissue. In addition, AIF-2 and -3 may be used as targets in assays for the identification of antagonists such as small orgainic molecules which act to block A1F activity. Such assays are known in the art.

FEATURES OF PROTEIN ENCODED BY SEQ ID NO: 15

The full-length nucleotide sequence of a novel human cDNA clone (HSAAL25) has been isolated which is believed to encode a new member of the annexin/lipocortin supergene family. The novel polypeptide is termed herein "Annexin HSAAL25". The annexin/lipocortin supergene family is composed of at least ten calcium-binding proteins proposed to function in a variety of cellular roles including phospholipase A2 and protein kinase C inhibition, anti-coagulation, endo- and exo-cytosis, inositol phosphate metabolism, and as calcium channel proteins. Eukaryotic calcium-binding proteins are typically classified as proteins which bind calcium by a mechanism which either includes or does not include an E-F hand motif. The annexin/lipocortin superfamily is the largest group of calcium-binding proteins whose interaction with calcium is not mediated by an E-F hand motif. Structurally, all known annexins may be characterized by a common carboxy terminal region consisting of four similar amino acid sequences, of approximately seventy amino acids each, termed the "annexin repeats". Conversely, the amino termini of annexinilipocortin proteins vary widely in both length and amino acid composition between member protein sequences. Typical expression patterns of annexin/lipocortin proteins include a wide variety of cells and tissues including lung, kidney, bone marrow, spleen, thymus, brain, macrophage, placenta, ovary, uterus, skeletal muscle, and others.

Annexin/lipocortin proteins are involved in a wide variety of physiologically important cellular processes. For example, lipocortin-1 (LC-1; also known as annexin-1) appears to function as a second messenger in the anti-inflammatory glucocorticoid signal transduction cascade. Most LC-1 molecules are cell surface-associated and attached to the plasma membrane by a Ca2+-dependent interaction with unrelated plasma membrane binding molecules. The process of extravasation, in which polymorphonuclear leukocytes (PMNs) migrate into an area of inflammation, adhere to the vascular wall, and eventually pass through the vascular wall into the surrounding tissue, may be delayed by glucocorticoids, and, as a result of LC-1 function, the overall process of inflammation may be delayed. As an example of the diversity of LC-1, and other annexin/lipocortin superfamily member, function, LC-1 has also been shown to play a major regulatory role in a number of possibly unrelated cellular systems such as cell growth regulation and differentiation, response of the CNS to cytokines, neuroendocrine secretion, anti-coagulation, and neurodegeneration.

Annexin HSAAL25 contains a 1356 nucleotide cDNA insert (SEQ ID NO:15) encoding a 324 amino acid polypeptide (SEQ ID NO:16), as is shown in FIGS. 8A–C. HSAAL25 was isolated from a cDNA library made from the HSA 172 cell line. Although previously described annexin/lipocortin proteins are widely expressed, this clone also appears only once in the HSA172 cell line cDNA library and does not appear in any other tissue type assayed for. A BLAST analysis of the amino acid sequence of HSAAL25 demonstrated that this clone exhibits at least 30% identity and 55% similarity over the entire length of a molecule designated human annexin-III, a member of the annexin/lipocortin supergene family.

There is clearly a need for identifying and exploiting novel members of the annexin/lipocortin superfamily such as the cDNA clone described herein. Plasma membrane-associated molecules, such as the novel potential members of the annexin/lipocortin superfamily detailed here, should prove useful in target based screens for small molecules and other such pharmacologically valuable factors that may be useful for regulating the complex processes of inflammation. Furthermore, Annexin HSAAL25 is believed to be useful as a regulator of coagulation (anti-coagulant) by affecting Ca2+-dependent cell to cell aggregation. In addition, this annexin-like clone may prove valuable in a number of other therapeutically useful roles as an anti-inflammatory agent including regulation of ischemia, tumor metastasis, rheumatoid arthritis, other inflammatory diseases, wound healing, arteriosclerosis, and other heart diseases.

FEATURES OF PROTEIN ENCODED BY SEQ ID NO: 17

The full-length nucleotide sequence of a novel human cDNA (HUSAX55) which encodes a previously unidentified "ES/130-like I" protein has been identified. The translation product of the novel full-length ES/130-like I cDNA clone exhibits significant sequence identity to the chicken EDTA-soluble/130 kDa protein (ES/130) gene. The ES/130-like I cDNA clone contains an 3036 nucleotide insert (SEQ ID NO:17) which encodes a 977 amino acid polypeptide (SEQ ID NO:18), as shown in FIGS. 9A–K. The clone was obtained from an umbilical vein endothelial cell cDNA library. A BLAST analysis of the deduced amino acid sequence of HUSAX55 exhibits approximately 66% identity and 83% similarity to the amino acid sequence of the chicken ES/130 gene over a 573 amino acid stretch. Expression of ES/130-like I is detected in a wide collection of HGS human cDNA libraries including amygdala depression, thymus, smooth muscle, endometrial tumor, synovial sarcoma, macrophage, fetal heart, and a number of others. Northern blot analyses performed on expression of the ES/130-like I gene indicates a high level of expression in pancreas and liver and moderate to low expression elsewhere.

The in vitro process of endothelial cell transformation to mesenchymal tissue models a similar in vivo process in the developing heart where closely associated epithelial cells undergo a transformation to cardiac mesenchyme tissue. This transformation is a required event for the development of a multichambered heart from the primative, single chambered heart tube. ES/130 was originally identified as a 130 kD antigen isolated from the 100,000 ×g pellet fraction of non-cytolytic EDTA extracts of developing chicken cardiac tissue. Inclusion of this fraction in cardiac endothelial cell cultures results in formation of mesenchymal tissue. ES/130 is an extracellular, secreted protein which, in addition to endothelial cell transformation, has been proposed to function in the regulation of adhesion molecule expression and limb bud ectoderm, neural tube, and notocord development. Potential therapeutic and/or diagnostic applications for the ES 130-like I protein include such clinical presentations as atherosclerosis, restenosis, or as a general factor following a number of types of surgery.

FEATURES OF THE PROTEIN ENCODED BY SEQ ID NO: 19

The full-length nucleotide sequence of a human cDNA clone (HSXCK41) which encodes a novel brain-enriched hyaluronan-binding factor ("BEF") has been determined. The novel BEF CDNA clone presented herein was discovered in a human substantia nigra cDNA library. The clone contains a 1757 nucleotide insert (SEQ ID NO:19) which is predicted to encode a 528 amino acid polypeptide (SEQ ID NO:20). A BLAST analysis of the predicted amino acid sequence of HSXCK41 demonstrates significant sequence identity to the bovine brevican mRNA (GenBank entry X75887), a member of the aggrecan/versican family of cell surface proteoglycans. The HSXCK41 amino acid sequence exhibits approximately 92% identity and 95% similarity over an approximately 400 amino acid stretch of the brevican sequence. This clone has been identified in a number additional HGS human cDNA libraries, many of which originate from neural tissues. These include epileptic frontal cortex, early stage brain, skin tumor, hippocampus, cerebellum, hemangiopericytoma, infant brain, fetal brain, and fetal bone.

The aggrecan/versican family of cell surface proteoglycans may be characterized by the presence of chondroitin sulfate side chains, a hyaluronic acid (HA)-binding motif in the amino terminal domain, and at least one epidermal growth factor (EGF)-like repeat, a lectin-like motif, and one or more complement regulatory protein (CRP)-like motifs in the carboxy terminal domain. The aggrecan/versican family includes a number of members such as brevican, aggrecan, decorin, versican, and neurocan. Brevican is expressed predominantly in the brain and in primary cerebellar astrocytes, but not in neurons. Meanwhile, both aggrecan and versican are expressed in chondrocytes in human articular cartilage obtained from subjects of a wide range of ages. Aggrecan messenger RNAs undergo alternative splicing events which vary the inclusion or exclusion of the single EGF-like motif in the carboxy terminal domain. Alternatively, versican contains two EGF-like motifs and a single CRP-like motif, all of which are present in all expression patterns examined. Finally, the expression of two recently described members of the aggrecan/versican family isolated from the human sciatic nerve is significantly increased following lesioning of the nerve.

The functional roles of members of the aggrecan/versican family are rather varied. Aggrecan itself aggregates with HA to function as a major space-filling component of cartilage. Brevican, an aggrecan/versican family member which is a conditional chondroitan sulfate proteoglycan, appears in a secreted, soluble form as well as in a GPI-anchored form. Both brevican isoforms have been implicated as functional components of the terminally differentiating and adult nervous systems. It will likely be determined that molecules such as these and the novel BEF cDNA clone HSXCK41 may play a role in one or more of a variety of cellular processes which typically involve intercellular contact and communication mediated through cell surface and/or secreted glycoprotein factors. Such cellular processes might include cell adhesion, proliferation, tumor metastasis, and lymphocyte migration into areas of inflammation. Related polypeptides are believed to be expressed at a higher level in tumors such as gliomas. Thus, BEF polynucleotides and polypeptides are useful as diagnostic markers and reagents for detection of tumors such as gliomas.

FEATURES OF THE PROTEIN ENCODED BY SEQ ID NO:21

The full-length nucleotide sequence of a human cDNA clone (HFKFY79) which encodes a novel adipose differentiation factor ("ADF") has recently been determined. The novel ADF cDNA clone presented herein was originally isolated from a human fetal kidney cDNA library. The clone contains a 1550 nucleotide insert (SEQ ID NO:21) which encodes a 452 amino acid polypeptide (SEQ ID NO:22), as shown in FIGS. 11A–E. A BLAST analysis of the predicted amino acid sequence of HFKFY79 demonstrates that this clone exhibits its highest degree of sequence relatedness in the GenBank public database to the murine ADF protein (GenBank accession number M93275). Based on its homology to murine ADF, human ADF is believed to share common biological activities. A BestFit analysis of the predicted amino acid sequence of HFKFY79 versus the murine ADF amino acid sequence demonstrates that the two protein sequences exhibit approximately 39% identity and 79% similarity. The expression profile of the HFKFY79 clone suggests a widely distributed expression pattern. In addition to the human fetal kidney library from which this clone was obtained, it also appears in a large number of human cDNA libraries including ulcerative colitis, adult testis, hypothalamus, induced endothelial cells, Jurkat T-cell line in S-phase, serum-treated and control smooth muscle, adipocytes, adult small intestine, lymph node breast cancer, infant brain, and many others.

The murine ADF gene was cloned by Jiang & Serrero (Proc. Natl. Acad. USA 89, 7856–7860; 1992, incorporated herein by reference) in an effort to identify genes whose expression profiles change significantly during the process of 1246 adipocyte cell and primary adipocyte differentiation. The murine ADF gene product identified by Jiang & Serrero is a 50 kD, membrane-bound protein expressed abundantly in mouse fat pads. The novel cDNA presented herein also exhibits sequence identity to several additional lipid-specific proteins. The first of the putative homologues is the major substrate for cAMP-dependent protein kinase A (PKA) in adipocytes and is termed perilipin. Perilipin is expressed in two alternatively spliced forms designated perilipins A and B. Both forms of perilipins are expressed exclusively at the surface of lipid storage droplets. It is thought that perilipids may function as a barrier to deny access of lipase to lipid reservoir of unstimulated cells. This event may be regulated by PKA-dependent phosphorylation of perilipin which allows exposure of lipid molecules to lipase. In addition, ADF is also related by sequence identity to a gene cloned from a human bone marrow-derived stromal cell line (KM-102) designated adipogenesis inhibitory factor (AGIF). AGIF has been shown to inhibit the process of adipogenesis in the mouse preadipocyte cell line 3T3-L1. Thus, human ADF may be useful among other things as a therapeutic modulator of lipid metabolism in the human body.

FEATURES OF THE PROTEIN ENCODED BY SEQ ID NO:23

The novel "Bcl-like" cDNA clone (HAICH28) presented herein was originally identified in a TNF-a/IFN-induced endothelial cell cDNA library. The clone contains a 1211 nucleotide insert (SEQ ID NO:23) which encodes a 365 amino acid polypeptide (SEQ ID NO:24). A BLAST analysis of the predicted amino acid sequence of HAICH28 demonstrates that this clone exhibits strong sequence similarity to two previously reported genes termed bovine polyA binding protein II and human Bcl-w (GenBank accession numbers X89969 and U59747, respectively). The expression profile of the HAICH28 clone suggests a widely distributed expression pattern. In addition to the TNF-a/IFN-induced endothelial cell library from which this clone was obtained, it also appears in a large number of human cDNA libraries including PHA-stimulated T-cells, osteoblasts, schizophrenic hypothalamus, activated monocytes, adrenal gland tumor, primary dendritic cells, and a number of others.

The protein product of the related Bcl-w gene has been determined to function as a key player in the cellular apoptosis or cell death pathway. Apoptosis is a term which describes the process of programmed cell death in vertebrates. During the process of apoptosis, the cell membrane shrinks and blebs resulting in a loss of membrane integrity and intercellular contact. In addition, the chromatin is condensed and cleaved into a characteristic ladder-like organization and, finally, vesicular remnants of the cell are quickly engulfed and destroyed by neighboring cells. The signal for the cell to enter the apoptotic pathway likely begins with the binding of Fas ligand or tumor necrosis factor (TNF), or the recently discovered TRAIL ligand, to the Fas/CD95/APO-1 or TNF (p55), or DR4 or DR5 receptors, respectively. These ligand/receptor interactions recruit a cellular protein designated FLICE to the cell membrane to act as a physical link between the Fas/CD95/APO-1 and TNF receptor complexes, also termed death receptors, and the cysteine proteases belonging to the interleukin-1b (IL-1b) converting enzyme (ICE)/CED-3 family to carry out the process of apoptosis.

The t(14:18) chromosomal translocation is often associated with human follicular lymphoma. In this chromosomal abnormality, the immunoglobulin heavy chain locus becomes translocated adjacent to the Bcl-2 gene, resulting in a drastic overexpression of the Bcl-2 gene. Bcl-2 blocks the process of apoptosis by an unknown mechanism. It has been proposed that Bcl-2 controls the process of apoptosis by regulating endoplasmic reticulum-associated Ca2+ fluxes. Several other genes have been identified which have significant regions of sequence identity with Bcl-2, including Ced-9, BHRF1, Bax, Bcl-xS, Bcl-xL, Bcl-w, Bak, Mcl-1, and GRS. The protein product of each of these genes can affect the process of apoptosis in either a positive (for example, Bax or Bcl-xS) or negative (for example Bcl-2, BHRF1, Ced-9, or Bcl-xL) fashion.

A large number of cells fall victim to the apoptotic process throughout development and during the lifetime of the organism. Clearly, strict regulation of the functional molecules comprising such a potentially dangerous process is an extremely necessary and valuable facet of the repertoire of cellular regulatory pathways. As a result, the identification of novel molecules related to Bcl-2 or Bcl-w, such as that encoded by the novel cDNA clone described herein, represents a major step in understanding, and, in turn, exploiting the complex process of controlled cell death. Accordingly, the Bcl-like polypeptide of the present invention is thought to be useful as a therapeutic in an anti-viral or anti-tumor capacity or, alternatively, in a diagnostic capacity.

What is claimed is:

1. An isolated protein comprising a polypeptide having an amino acid sequence selected from the group consisting of:
   (a) amino acid residues 1–103 of SEQ ID NO:2;
   (b) amino acid residues 2–103 of SEQ ID NO:2;
   (c) a fragment of the polypeptide set forth as amino acid residues 1 to 103 of SEQ ID NO:2, wherein said fragment has chemotactic activity;
   (d) an amino acid sequence at least 95% identical to the amino acid sequence of (a), (b) or (c) (reference sequence SEQ ID NO:2), wherein said polypeptide has chemoactic activity; and
   (e) an amino acid sequence having at least 30 contiguous amino acid residues of SEQ ID NO:2, wherein said polypeptide specifically binds an antibody that specifically binds a polypeptide having the amino acid sequence of SEQ ID NO:2.

2. The isolated protein of claim 1, comprising a polypeptide having at least 30 contiguous amino acid residues of SEQ ID NO:2.

3. The isolated protein of claim 2 comprising a polypeptide having at least 50 contiguous amino acid residues of SEQ ID NO:2.

4. A The isolated protein of claim 3 comprising a polypeptide having amino acid residues 2–103 of SEQ ID NO:2.

5. The isolated protein of claim 4 comprising a polypeptide having amino acid residues 1–103 of SEQ ID NO:2.

6. The isolated protein of claim 1 comprising a fragment of the polypeptide set forth as amino acid residues 1 to 103 of SEQ ID) NO:2 wherein said fragment has chemotaic activity.

7. The isolated protein of claim 1 further comprising a polypeptide having a heterologous amino acid sequence.

8. An isolated protein comprising a polypeptide having an amino acid sequence selected from the group consisting of:
   (a) the amino acid sequence of the complete polypeptide encoded by the human cDNA HEMFI85;
   (b) the amino acid sequence of the complete polypeptide encoded by the human cDNA HEMFI85 excepting the N-terminal methionine residue;
   (c) the amino acid sequence of a fragment of the complete polypeptide encoded by the human CDNA HEMFI85, wherein said fragment has chemotactic activity;
   (d) the amino acid sequence of a polypeptide with at least 95% identity to the polypeptide of (a), (b) or (c) (reference sequence complete polypeptide encoded by the human cDNA HEMFI85), wherein said fragment has chemotactic activity; and
   (e) at least 30 contiguous amino acid residues of the complete polypeptide encoded by the human cDNA HEMFI85, wherein said polypeptide specifically binds an antibody that specifically binds a polypeptide having the amino acid sequence of the complete polypeptide encoded by the human cDNA HEMFI85.

9. The isolated protein of claim 8 comprising a polypeptide having at least 30 contiguous amino acid residues of the complete polypeptide encoded by the human cDNA HEMFI85.

10. The isolated protein of claim 9 comprising a polypeptide having at least 50 contiguous amino acid residues of the complete polypeptide encoded by the human cDNA HEMFI85.

11. The isolated protein of claim 10 comprising the amino acid sequence of the complete polypeptide encoded by the human cDNA HEMFI85 excepting the N-terminal methionine residue.

12. The isolated protein of claim 11 comprising the amino acid sequence of the complete polypeptide encoded by the human cDNA HEMFI85.

13. The isolated protein of claim 8 comprising the amino acid sequence of a fragment of the polypeptide encoded by the human cDNA HEMF185 wherein said fragment has chemoractic activity.

14. The isolated protein of claim 8 further comprising a heterologous amino acid sequence.

15. A composition comprising the isolated protein of claim 1.

16. A composition comprising the isolated protein of claim 2.

17. A composition comprising the isolated protein of claim 8.

18. A composition comprising the isolated protein of claim 9.

19. The isolated protein of claim 1, wherein said amino acid sequence is (d).

20. The isolated protein of claim 8, wherein said amino acid sequence is (d).

21. The isolated protein of claim 19, wherein said amino acid sequence is at least 97% identical to the amino acid sequence of (a) (reference sequence), wherein % identity is determined using the Bestfit program with parameters that calculate % identity over the full length of the reference sequence and that allows gaps of up to 3% of the total number of amino acid residues of the reference sequence.

22. The isolated protein of claim 21, wherein said amino acid sequence is at least 98% identical to the amino acid sequence of (a) (reference sequence), wherein % identity is determined using the Bestfit program with parameters that calculate % identity over the full length of the reference sequence and that allows gaps of up to 2% of the total number of amino acid residues of the reference sequence.

23. The isolated protein of claim 20, wherein said amino acid sequence is at least 97% identical to the amino acid sequence of (a) (reference sequence), wherein % identity is determined using the Bestfit program with parameters that calculate % identity over the full length of the reference sequence and that allows gaps of up to 3% of the total number of amino acid residues of the reference sequence.

24. The isolated protein of claim 23, wherein said amino acid sequence is at least 98% identical to the amino acid sequence of (a) (reference sequence), wherein % identity is determined using the Bestfit program with parameters that calculate % identity over the full length of the reference sequence and that allows gaps of up to 2% of the total number of amino acid residues of the reference sequence.

* * * * *

UNITED STATES PATENT AND TRADEMARK OFFICE

CERTIFICATE OF CORRECTION

PATENT NO. : 6,653,445 B1 Page 1 of 1
DATED : November 25, 2003
INVENTOR(S) : Ni et al.

It is certified that error appears in the above-identified patent and that said Letters Patent is hereby corrected as shown below:

Column 93,
Lines 44-47, that portion of claim 1(d) which reads "wherein said polypeptide has chemoactic activity" should read -- wherein said polypeptide has chemotactic activity --;
Lines 58-59, that portion of claim 4 which reads "A The isolated protein of claim 3 comprising" should read -- The isolated protein of claim 3 comprising --;
Lines 62-65, that portion of claim 6 which reads "of SEQ ID) NO:2 wherein said fragment has chemotaic activity" should read --of SEQ ID NO:2 wherein said fragment has chemotactic activity --.

Column 94,
Lines 43-44, that portion of claim 8(c) which reads "by the human CDNA HEMF185" should read -- by the human cDNA HEMF185 --.

Column 95,
Lines 6-8, that portion of claim 13 which reads "wherein said fragment has chemoractic activity" should read -- wherein said fragment has chemotactic activity --.

Signed and Sealed this

Sixth Day of July, 2004

JON W. DUDAS
*Acting Director of the United States Patent and Trademark Office*